US008957140B2

(12) United States Patent
Amasaki et al.

(10) Patent No.: US 8,957,140 B2
(45) Date of Patent: Feb. 17, 2015

(54) TRIAZINE DERIVATIVE, ULTRAVIOLET ABSORBER, AND RESIN COMPOSITION

(75) Inventors: Ichiro Amasaki, Kanagawa (JP); Keizo Kimura, Kanagawa (JP); Yukie Watanabe, Kanagawa (JP); Kyosuke Tsumura, Kanagawa (JP); Hiroshi Yokoyama, Kanagawa (JP); Takumi Nakamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 115 days.

(21) Appl. No.: 13/387,505

(22) PCT Filed: Jul. 28, 2010

(86) PCT No.: PCT/JP2010/062734
§ 371 (c)(1),
(2), (4) Date: Feb. 21, 2012

(87) PCT Pub. No.: WO2011/013723
PCT Pub. Date: Feb. 3, 2011

(65) Prior Publication Data
US 2012/0136098 A1    May 31, 2012

(30) Foreign Application Priority Data

Jul. 29, 2009  (JP) ................................ 2009-176897
Sep. 7, 2009  (JP) ................................ 2009-206478
Sep. 25, 2009  (JP) ................................ 2009-221661
Jan. 19, 2010  (JP) ................................ 2010-009536
Jul. 2, 2010  (JP) ................................ 2010-152490
Jul. 2, 2010  (JP) ................................ 2010-152491

(51) Int. Cl.
*C08K 5/3492*    (2006.01)
*C07D 251/00*    (2006.01)
(Continued)

(52) U.S. Cl.
CPC ............ *C07D 251/24* (2013.01); *C08K 5/3492* (2013.01); *C09K 15/30* (2013.01)
USPC .......................................... 524/100; 544/216

(58) Field of Classification Search
USPC ........................................................ 524/100
See application file for complete search history.

(56) References Cited

U.S. PATENT DOCUMENTS 1,065,425 A    6/1913 Basinski
3,113,941 A    12/1963 Johns et al.
(Continued)

FOREIGN PATENT DOCUMENTS

BE    650 932 A    1/1965
JP    5339033 A    12/1993
(Continued)

OTHER PUBLICATIONS

European Search Report dated Jan. 4, 2013 issued by the European Patent Office in counterpart European Patent Application No. 10804469.4.
International Search Report dated Oct. 19, 2010 from the International Searching Authority in counterpart application No. PCT/JP2010/062734.
Written Opinion of the International Searching Authority dated Oct. 19, 2010 from the International Searching Authority in counterpart application No. PCT/JP2010/062734.
Written Opinion dated on Oct. 19, 2010 in corresponding International Application No. PCT/JP2010/062734.
Office Action dated Jan. 14, 2014 issued by the European Patent Office in counterpart European Patent Application No. 10804469.4.
C. Hansch et al., "A Survey of Hammett Substituent Constants and Resonance and Field Parameters," Chemical Reviews, vol. 91, 1991, pp. 165-195.

(Continued)

*Primary Examiner* — Hui Chin
(74) *Attorney, Agent, or Firm* — Sughrue Mion, PLLC

(57) ABSTRACT

To provide a novel triazine-based compound exhibiting an ultraviolet blocking effect even in the long-wavelength region and being useful as an ultraviolet absorber with excellent light resistance, and to provide an ultraviolet absorber and a resin composition, which can maintain a long-wavelength ultraviolet-blocking effect for a long period of time. A compound represented by the following formula (1):

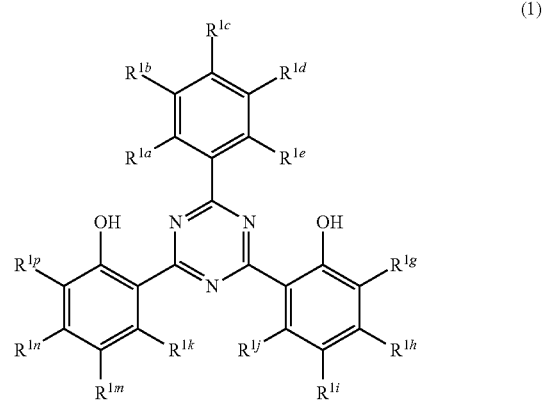

(1)

wherein each of $R^{1a}$, $R^{1b}$, $R^{1c}$, $R^{1d}$ and $R^{1e}$ independently represents a hydrogen atom or a monovalent substituent excluding OH, provided that at least one substituent represents a substituent having a Hammett's σp value of 0.3 or more and substituents may combine with each other to form a ring, and each of $R^{1g}$, $R^{1h}$, $R^{1i}$, $R^{1j}$, $R^{1k}$, $R^{1m}$, $R^{1n}$ and $R^{1p}$ independently represents a hydrogen atom or a monovalent substituent, provided that substituents may combine with each other to form a ring.

11 Claims, No Drawings

(51) Int. Cl.
*C07D 251/24* (2006.01)
*C09K 15/30* (2006.01)

(56) References Cited

U.S. PATENT DOCUMENTS

| | | | |
|---|---|---|---|
| 3,249,608 | A | 5/1966 | Biland et al. |
| 4,826,978 | A * | 5/1989 | Migdal et al. ............. 544/216 |
| 5,543,518 | A * | 8/1996 | Stevenson et al. ......... 544/215 |
| 5,545,836 | A * | 8/1996 | Reinehr et al. ............ 544/216 |
| 5,556,973 | A | 9/1996 | Stevenson et al. |
| 5,637,706 | A | 6/1997 | Stevenson et al. |
| 6,090,370 | A | 7/2000 | Luther et al. |
| 6,225,468 | B1 | 5/2001 | Gupta et al. |
| 2003/0113515 | A1 * | 6/2003 | Lawrence et al. ......... 428/195 |
| 2006/0019206 | A1 * | 1/2006 | Dickerson et al. ........ 430/619 |
| 2009/0021671 | A1 * | 1/2009 | Fukagawa et al. ......... 349/96 |
| 2011/0311786 | A1 * | 12/2011 | Cunningham et al. ..... 428/195.1 |

FOREIGN PATENT DOCUMENTS

| | | | | |
|---|---|---|---|---|
| JP | 5345639 | A | | 12/1993 |
| JP | 656466 | A | | 3/1994 |
| JP | 853427 | A | | 2/1996 |
| JP | 200588284 | A | | 3/2002 |
| JP | 2002524452 | A | | 8/2002 |
| JP | 2004-352728 | A | | 12/2004 |
| JP | 2004352728 | A | | 12/2004 |
| JP | 3965631 | B2 | | 6/2007 |
| JP | 2007-298648 | A | | 11/2007 |
| JP | 2007298648 | A | * | 11/2007 |
| JP | 2007298648 | A | | 11/2007 |
| WO | WO 9418278 | A2 | | 8/1994 |
| WO | WO 9418278 | A2 | * | 8/1994 ............... C09D 7/12 |
| WO | 2008/110487 | A1 | | 9/2008 |
| WO | WO 2008110487 | A1 | | 9/2008 |

OTHER PUBLICATIONS

Office Action dated Jan. 6, 2014, issued by the State Intellectual Property Office of P.R. China in counterpart Chinese Patent Application No. 201080042098.7.

Office Action dated Mar. 4, 2014 issued by the Japanese Patent Office in counterpart Japanese Patent Application No. 2010-152490.

Office Action dated Mar. 4, 2014 issued by the Japanese Patent Office in counterpart Japanese Patent Application No. 2010-152491.

Chapas, Richard et al., "The Nef-Type Transformation in Basic Solution," Journal of Organic Chemistry, vol. 40, No. 25, Jul. 30, 1975, pp. 3746 to 3748.

CAplus, "L15 Answer 169 of 169 CAPLUS," STN Online, AN1927:561, 2014 2 pages total.

Office Action dated Sep. 25, 2014, issued by the State Intellectual Property Office of the People's Republic of China in counterpart Chinese Application No. 201080042098.7.

* cited by examiner

TRIAZINE DERIVATIVE, ULTRAVIOLET ABSORBER, AND RESIN COMPOSITION

TECHNICAL FIELD

The present invention relates to a new triazine derivative, an ultraviolet absorber, and a resin composition.

BACKGROUND ART

Conventionally, it has been done to impart an ultraviolet absorbing property by using an ultraviolet absorber in combination with various resins or the like. An inorganic ultraviolet absorber or an organic ultraviolet absorber is used as the ultraviolet absorber. In the case of an inorganic ultraviolet absorber (see, for example, Patent Documents 1 to 3), the durability such as weather resistance and heat resistance is excellent, but since the absorption wavelength is determined by the band gap of the compound, the latitude in selection is narrow, leading to the fact that an absorber capable of absorbing light even in the long-wavelength ultraviolet (UV-A) region of around 400 nm is not known and an absorber capable of absorbing light in the long-wavelength ultraviolet region has absorption also in the visible region and therefore, involves coloring.

On the other hand, the organic ultraviolet absorber has a wide latitude in the design of absorber structure and therefore, absorbers having various absorption wavelengths can be obtained by designing the absorber structure.

Systems using various organic ultraviolet absorbers have been heretofore studied, and Patent Document 4 discloses a triazole-based ultraviolet absorber. Also, Patent Document 5 describes a trisaryl-s-triazine having an alkoxy group and a hydroxy group at specific positions. However, those having a maximum absorption wavelength in the long-wavelength ultraviolet region are poor in the light resistance, and their ultraviolet blocking effect wears off with the passage of time.

Furthermore, a material applied to a solar cell or the like recently under development must be exposed to sunlight outdoors for a long period of time, and due to exposure to ultraviolet light over long term aging, the material is unavoidably deteriorated in its property. Accordingly, a compound exhibiting a blocking effect even in the UV-A region and being usable as an ultraviolet absorber with more excellent light resistance than ever is demanded.

RELATED ART

Patent Document

Patent Document 1: JP-A-5-339033 (the term "JP-A" as used herein means an "unexamined published Japanese patent application")

Patent Document 2: JP-A-5-345639

Patent Document 3: JP-A-6-56466

Patent Document 4: JP-T-2002-524452 (the term "JP-T" as used herein means a published Japanese translation of a PCT patent application)

Patent Document 5: JP Patent 3965631

SUMMARY OF THE INVENTION

Problems that the Invention is to Solve

An object of the present invention is to provide a novel triazine-based compound exhibiting an ultraviolet blocking effect even in the long-wavelength region and being useful as an ultraviolet absorber with excellent light resistance. Another object of the present invention is to provide an ultraviolet absorber and a resin composition, which can maintain a long-wavelength ultraviolet-blocking effect for a long period of time and exhibit excellent solubility for solvent and excellent heat resistance, ensuring that not only the ultraviolet light durability of a polymer material or the like can be enhanced but also the decomposition of other unstable compounds can be suppressed by using the polymer material as an ultraviolet light filter.

Means for Solving the Problems

As a result of detailed studies on the triazine-based compound, the present inventors have found a compound having a conventionally unknown structure, which can exhibit a blocking effect even in the UV-A region and ensure unprecedented excellent light resistance, solvent solubility and heat resistance. The present invention has been accomplished based on this finding.

The above-described objects can be achieved by the following methods:

[1] A compound represented by the following formula (1):

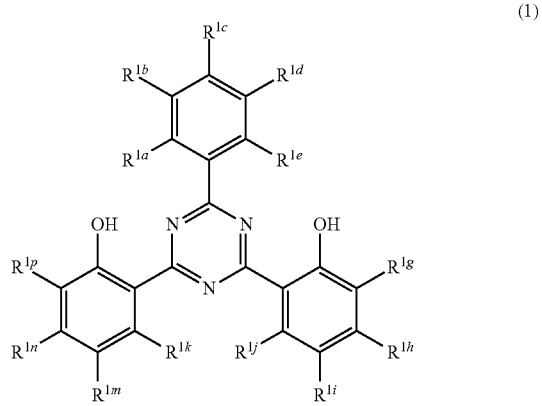

wherein each of $R^{1a}$, $R^{1b}$, $R^{1c}$, $R^{1d}$ and $R^{1e}$ independently represents a hydrogen atom or a monovalent substituent excluding OH, provided that at least one substituent represents a substituent having a Hammett's σp value of 0.3 or more and substituents may combine with each other to form a ring, and each of $R^{1g}$, $R^{1h}$, $R^{1i}$, $R^{1j}$, $R^{1k}$, $R^{1m}$, $R^{1n}$ and $R^{1p}$ independently represents a hydrogen atom or a monovalent substituent, provided that substituents may combine with each other to form a ring.

[2] The compound as described in [1], wherein each of $R^{1a}$, $R^{1c}$ and $R^{1e}$ independently represents a hydrogen atom or a monovalent substituent excluding OH, provided that at least one substituent represents a substituent having a Hammett's σp value of 0.3 or more, and each of $R^{1b}$ and $R^{1d}$ independently represents a hydrogen atom or a monovalent substituent excluding OH, provided that substituents may combine with each other to form a ring.

[3] The compound as described in [1], wherein each of $R^{1a}$, $R^{1c}$ and $R^{1e}$ represents a hydrogen atom, and each of $R^{1b}$ and $R^{1d}$ independently represents a hydrogen atom or a substituent having a Hammett's σp value of 0.3 or more, provided that at least one substituent represents a substituent having a Hammett's σp value of 0.3 or more.

[4] The compound as described in any one of [1] to [3], wherein the monovalent substituent is a halogen atom, a substituted or unsubstituted alkyl group having a carbon number of 1 to 20, a cyano group, a carboxyl group, a substituted or unsubstituted alkoxycarbonyl group, a substituted or unsubstituted carbamoyl group, a substituted or unsubstituted alkylcarbonyl group, a nitro group, a substituted or unsubstituted amino group, a hydroxy group, an alkoxy group having a carbon number of 1 to 20, a substituted or unsubstituted aryloxy group, a substituted or unsubstituted sulfamoyl group, a thiocyanate group, or a substituted or unsubstituted alkylsulfonyl group and in the case of having a substituent, the substituent is a halogen atom, an alkyl group having a carbon number of 1 to 20, a cyano group, a carboxyl group, an alkoxycarbonyl group, a carbamoyl group, an alkylcarbonyl group, a nitro group, an amino group, a hydroxy group, an alkoxy group having a carbon number of 1 to 20, an aryloxy group, a sulfamoyl group, a thiocyanate group or an alkylsulfonyl group.

[5] The compound as described in any one of [1] to [3], wherein the Hammett's σp value is from 0.3 to 1.2.

[6] The compound as described in any one of [1] to [4], wherein the substituent as the substituent having a Hammett's σp value of 0.3 or more is a group selected from COOR$^r$, CONR$^s_2$, a cyano group, CF$_3$, a nitro group and SO$_3$M, wherein each of R$^r$ and R$^s$ independently represents a hydrogen atom or a monovalent substituent and M represents a hydrogen atom or an alkali metal.

[7] The compound as described in any one of [1] to [4] and [6], wherein the substituent as the substituent having a Hammett's σp value of 0.3 or more is COOR$^r$, wherein R$^r$ represents a hydrogen atom or a monovalent substituent.

[8] The compound as described in any one of [1], [2], [4] and [5], wherein R$^{1c}$ is a cyano group.

[9] The compound as described in any one of [1] to [8], wherein R$^{1h}$ or R$^{1n}$ is a hydrogen atom.

[10] The compound as described in any one of [1] to [9], wherein R$^{1g}$, R$^{1h}$, R$^{1i}$, R$^{1j}$, R$^{1k}$ R$^{1m}$, R$^{1n}$ and R$^{1p}$ are a hydrogen atom.

[11] The compound as described in any one of [1] to [10], wherein pKa is from −5.0 to −7.0.

[12] An ultraviolet absorber comprising the compound described in any one of [1] to [11].

[13] A resin composition containing the compound described in any one of [1] to [11].

ADVANTAGE OF THE INVENTION

The compound of the present invention can be used as an ultraviolet absorber. Also, the compound exhibits high light fastness even in the long-wavelength ultraviolet region and when the compound of the present invention is incorporated into a resin composition for forming a polymer shape-formed article such as plastic and fiber, light stability of the polymer shape-formed article can be enhanced.

MODE FOR CARRYING OUT THE INVENTION

The present invention is described in detail below.

[Compound Represented by Formula (1)]

The present invention relates to a compound represented by the following formula (1):

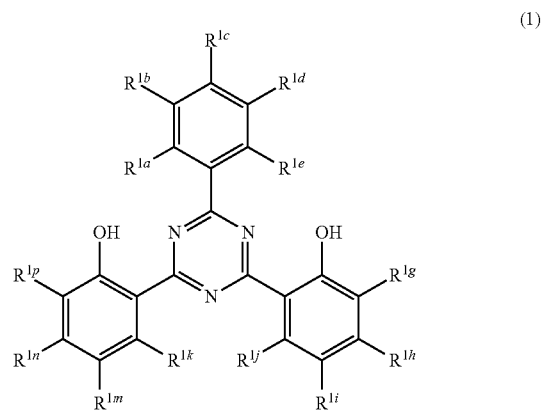

wherein each of R$^{1a}$, R$^{1b}$, R$^{1c}$, R$^{1d}$ and R$^{1e}$ independently represents a hydrogen atom or a monovalent substituent excluding OH, provided that at least one substituent represents a substituent having a Hammett's σp value of 0.3 or more and substituents may combine with each other to form a ring, and each of R$^{1g}$, R$^{1h}$, R$^{1i}$R$^{1j}$, R$^{1k}$, R$^{1m}$, R$^{1n}$ and R$^{1p}$ independently represents a hydrogen atom or a monovalent substituent, provided that substituents may combine with each other to form a ring.

Each of R$^{1a}$, R$^{1b}$, R$^{1c}$, R$^{1d}$ and R$^{1e}$ independently represents a hydrogen atom or a monovalent substituent excluding OH, provided that at least one substituent represents a substituent having a Hammett's σp value of 0.3 or more.

Out of the substituents represented by R$^{1a}$, R$^{1b}$, R$^{1c}$, R$^{1d}$ and R$^{1e}$, preferably, from 1 to 3 substituents are a substituent having a Hammett's σp value of 0.3 or more; and more preferably, 1 or 2 substituents are a substituent having a Hammett's σp value of 0.3 or more.

Also, preferably, at least one of R$^{1a}$, R$^{1c}$ and R$^{1e}$ represents a substituent having a Hammett's σp value of 0.3 or more; and more preferably, R$^{1c}$ represents a substituent having a Hammett's σp value of 0.3 or more.

It is more preferred that R$^{1c}$ is a substituent having a Hammett's σp value of 0.3 or more and each of R$^{1a}$, R$^{1b}$, R$^{1d}$ and R$^{1e}$ represents a hydrogen atom.

In the case where R$^{1c}$ represents a substituent having a Hammett's σp value of 0.3 or more, LUMO is stabilized by an electron-withdrawing group, and this advantageously yields short excitation life and enhanced light resistance.

Examples of the monovalent substituent (hereinafter referred to as the substituent A) in formula (1) include a halogen atom (e.g., fluorine atom, chlorine atom, bromine atom, iodine atom), an alkyl group having a carbon number of 1 to 20 (e.g., methyl, ethyl), an aryl group having a carbon number of 6 to 20 (e.g., phenyl, naphthyl), a cyano group, a carboxyl group, an alkoxycarbonyl group (e.g., methoxycarbonyl), an aryloxycarbonyl group (e.g., phenoxycarbonyl), a substituted or unsubstituted carbamoyl group (e.g., carbamoyl, N-phenylcarbamoyl, N,N-dimethylcarbamoyl), an alkylcarbonyl group (e.g., acetyl), an arylcarbonyl group (e.g., benzoyl), a nitro group, a substituted or unsubstituted amino group (e.g. amino, dimethylamino, anilino, substituted sulfoamino), an acylamino group (e.g., acetamide, ethoxycarbonylamino), a sulfonamido group (e.g., methanesulfonamido), an imido group (e.g., succinimido, phthalimido), an imino group (e.g., benzylideneamino), a hydroxy group, an alkoxy group having a carbon number of 1 to 20 (e.g., methoxy), an aryloxy group (e.g., phenoxy), an acyloxy group (e.g., acetoxy), an alkylsulfonyloxy group (e.g., methanesulfonyloxy), an arylsulfonyloxy group (e.g., benzenesulfonyloxy), a sulfo group, a substituted or unsubstituted sulfamoyl group (e.g., sulfamoyl, N-phenylsulfamoyl), an alkylthio group (e.g., methylthio), an arylthio group (e.g., phenylthio), a thiocyanate group, an alkylsulfonyl group (e.g., methanesulfonyl), an arylsulfonyl group (e.g., benzenesulfonyl), and a heterocyclic group having a carbon number of 6 to 20 (e.g., pyridyl, morpholino).

The substituent may be further substituted and when a plurality of substituents are present, they may be the same or different. In this case, examples of the substituent include the above-described monovalent substituent A. The substituents may combine with each other to form a ring.

Examples of the ring formed by combining the substituents with each other include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring, and a phosphole ring.

The monovalent substituent in formula (1) is preferably a halogen atom, a substituted or unsubstituted alkyl group having a carbon number of 1 to 20, a cyano group, a carboxyl group, a substituted or unsubstituted alkoxycarbonyl group, a substituted or unsubstituted carbamoyl group, a substituted or unsubstituted alkylcarbonyl group, a nitro group, a substituted or unsubstituted amino group, a hydroxy group, $OR^U$ (wherein $R^U$ represents a hydrogen atom or a monovalent substituent), a substituted or unsubstituted alkoxy group having a carbon number of 1 to 20, a substituted or unsubstituted aryloxy group, a substituted or unsubstituted sulfamoyl group, a thiocyanate group, or a substituted or unsubstituted alkylsulfonyl group, more preferably $OR^U$, an alkyl group or an amido group, still more preferably $OR^U$ or an alkyl group. In the case of having a substituent, the substituent is a halogen atom, an alkyl group having a carbon number of 1 to 20, a cyano group, a carboxyl group, an alkoxycarbonyl group, a carbamoyl group, an alkylcarbonyl group, a nitro group, an amino group, a hydroxy group, an alkoxy group having a carbon number of 1 to 20, an aryloxy group, a sulfamoyl group, a thiocyanate group or an alkylsulfonyl group.

$R^u$ represents a hydrogen atom or a monovalent substituent, and examples of the monovalent substituent include the substituent A. In particular, a linear or branched alkyl group having a carbon number of 1 to 20 is preferred, and a linear or branched alkyl group having a carbon number of 1 to 6 is more preferred. Examples of the linear or branched alkyl group having a carbon number of 1 to 6 include methyl, ethyl, n-propyl, i-propyl, n-butyl, butyl, s-butyl, tert-butyl, n-pentyl, i-pentyl, tert-pentyl, n-hexyl, i-hexyl, tert-hexyl, n-octyl, tert-octyl and i-octyl. Among these, methyl and ethyl are preferred, and methyl is more preferred.

In the present invention, the first preferred embodiment includes an embodiment where each of $R^{1a}$, $R^{1c}$ and $R^{1e}$ independently represents a hydrogen atom or a monovalent substituent excluding OH, at least one substituent represents a substituent having a Hammett's σp value of 0.3 or more, each of $R^{1b}$ and $R^{1d}$ independently represents a hydrogen atom or a monovalent substituent excluding OH, and the substituents may combine with each other to form a ring.

Each of $R^{1a}$, $R^{1c}$ and $R^{1e}$ independently represents a hydrogen atom or a monovalent substituent excluding OH, and at least one substituent represents a substituent having a Hammett's σp value of 0.3 or more.

Out of the substituents represented by $R^{1a}$, $R^{1c}$ and $R^{1e}$, preferably, 1 or 2 substituents are a substituent having a Hammett's σp value of 0.3 or more; and more preferably, 1 substituent is a substituent having a Hammett's σp value of 0.3 or more.

Also, preferably, at least one of $R^{1a}$, $R^{1c}$ and $R^{1e}$ represents a substituent having a Hammett's σp value of 0.3 or more; and more preferably, $R^{1c}$ represents a substituent having a Hammett's σp value of 0.3 or more.

It is more preferred that $R^{1c}$ is a substituent having a Hammett's σp value of 0.3 or more and each of $R^{1a}$, $R^{1b}$, $R^{1d}$ and $R^{1e}$ represents a hydrogen atom.

In the case where $R^{1c}$ represents a substituent having a Hammett's σp value of 0.3 or more, LUMO is stabilized by an electron-withdrawing group, and this advantageously yields short excitation life and enhanced light resistance.

Also, the second preferred embodiment includes an embodiment where each of $R^{1a}$, $R^{1c}$ and $R^{1e}$ represents a hydrogen atom, each of $R^{1b}$ and $R^{1d}$ independently represents a hydrogen atom or a substituent having a Hammett's σp value of 0.3 or more, and at least either one is a substituent having a Hammett's σp value of 0.3 or more.

Thanks to the configuration where at least either one of $R^{1b}$ and $R^{1d}$ is a substituent having a Hammett's σp value of 0.3 or more, the compound is not only excellent in the light resistance but also exhibits an excellent effect on the solvent solubility and heat resistance.

Thanks to the configuration where each of $R^{1a}$, $R^{1c}$ and $R^{1e}$ represents a hydrogen atom, each of $R^{1b}$ and $R^{1d}$ independently represents a hydrogen atom or a substituent having a Hammett's σp value of 0.3 or more, and at least one of $R^{1b}$ and $R^{1d}$ is a substituent having a Hammett's σp value of 0.3 or more, LUMO is stabilized by an electron-withdrawing group, and the excitation life is shortened. Also, the symmetry of the compound structure is lost, and the compound comes to have excellent light resistance and high solvent solubility.

The solvent solubility means solubility in an organic solvent such as ethyl acetate, methyl ethyl ketone and toluene, and the compound is preferably dissolved in a ratio of 10 mass % or more, more preferably 30 mass % or more, based on the solvent used.

The substituent having a Hammett's σp value of 0.3 or more in formula (1) is preferably an electron-withdrawing group having a $\sigma_p$ value of 0.3 to 1.2. Specific examples of the electron-withdrawing group having a $\sigma_p$ value of 0.3 or more include $COOR^r$ (wherein $R^r$ represents a hydrogen atom or a monovalent substituent and includes a hydrogen atom and an alkyl group, with an alkyl group being preferred), $CONR^s_2$ (wherein $R^s$ represents a hydrogen atom or a monovalent substituent and includes, for example, a hydrogen atom, an alkyl group having a carbon number of 1 to 20, an aryl group having a carbon number of 6 to 20, and a heterocyclic group having a carbon number of 6 to 20, with a hydrogen atom being preferred), a cyano group, a nitro group, $SO_3M$ (wherein M represents a hydrogen atom or an alkali metal), an acyl group, a formyl group, an acyloxy group, an acylthio group, an alkyloxycarbonyl group, an aryloxycarbonyl group, a dialkylphosphono group, a diarylphosphono group, a dialkylphosphinyl group, a diarylphosphinyl group, a phosphoryl group, an alkylsulfinyl group, an arylsulfinyl group, an alkylsulfonyl group, an arylsulfonyl group, an acylthio group, a sulfamoyl group, a thiocyanate group, a thiocarbonyl group, an imino group, an N atom-substituted imino group, a carboxy group (or a salt thereof), an alkyl group substituted with at least two or more halogen atoms (e.g., $CF_3$), an alkoxy group substituted with at least two or more halogen atoms, an aryloxy group substituted with at least two or more halogen atoms, an acylamino group, an alkylamino group substituted with at least two or more halogen atoms, an alkylthio group substituted with at least two or more halogen atoms, an aryl group substituted with another electron-withdrawing group having a $\sigma_p$ value of 0.3 or more, a heterocyclic group, an azo group, and a selenocyanate group. Details of the Hammett's σp value are described in C. Hansch, A. Leo and R. W. Taft, *Chem. Rev.*, 1991, 91, 165-195.

The substituent having a Hammett's σp value of 0.3 or more in formula (1) is more preferably $COOR^r$, $CONR^s_2$, a cyano group, $CF_3$, a nitro group or $SO_3M$ [wherein each of $R^r$ and $R^s$ independently represents a hydrogen atom or a monovalent substituent, and M represents a hydrogen atom or an alkali metal]. The monovalent substituent includes the substituent A.

The substituent having a Hammett's σp value of 0.3 or more in formula (1) is still more preferably $COOR^r$ or a cyano group, yet still more preferably $COOR^r$, because when the substituent having a Hammett's σp value of 0.3 or more is a cyano group, the compound exhibits excellent light resistance and solubility and when the substituent having a Hammett's σp value of 0.3 or more is $COOR^r$, the compound exhibits excellent solubility.

$R^r$ preferably represents a hydrogen atom or an alkyl group, more preferably a linear or branched alkyl group having a carbon number of 1 to 20, still more preferably a liner or branched alkyl group having a carbon number of 1 to 15.

In view of solubility for a solvent, $R^r$ is preferably a branched alkyl group having a carbon number of 5 to 15.

The branched alkyl group has a secondary or tertiary carbon atom and preferably contains from 1 to 5, from 1 to 3, or 1 or 2, secondary or tertiary carbon atoms, more preferably 1 or 2 secondary and tertiary carbon atoms. Also, it is preferred to contain from 1 to 3 asymmetric carbons.

In view of solubility for a solvent, $R^r$ is more preferably a branched alkyl group having a carbon number of 5 to 15 and containing 1 or 2 secondary and tertiary carbon atoms and 1 or 2 asymmetric carbons. This is because the symmetry of the compound structure is lost and the solubility is enhanced.

On the other hand, in view of ultraviolet absorbing ability, a linear or branched alkyl group having a carbon number of 1 to 6 is more preferred.

The linear or branched alkyl group having a carbon number of 1 to 6 includes a methyl group, an ethyl group, an n-propyl group, an i-propyl group, an n-butyl group, an i-butyl group, an s-butyl group, a tert-butyl group, an n-pentyl group, an i-pentyl group, a tert-pentyl group, an n-hexyl group, an i-hexyl group, a tert-hexyl group, an n-octyl group, a tert-octyl group, an i-octyl group, a 2-ethylhexyl group, a [2-(3-methylhexyl)-7-methyl]decyl group, and a 3,5,5-trimethyl-1-hexyl group. Among these group, a methyl group, an ethyl group, an n-butyl or 2-ethylhexyl group, a [2-(3-methylhexyl)-7-methyl]decyl, and 3,5,5-trimethyl-1-hexyl group are preferred group, and a methyl group is more preferred.

In the first preferred embodiment of the present invention, $R^{1c}$ is preferably any one of $COOR^r$, $CONR^s_2$, a cyano group, $CF_3$, a nitro group and $SO_3M$ (wherein M represents a hydrogen atom or an alkali metal), more preferably $COOR^r$ or a cyano group, still more preferably a cyano group.

In the first preferred embodiment of the present invention, when each of $R^{1g}$, $R^{1h}$, $R^{1i}$, $R^{1j}$, $R^{1k}$, $R^{1m}$, $R^{1n}$ and $R^{1p}$ represents a monovalent substituent, preferably, at least one of $R^{1g}$, $R^{1h}$, $R^{1i}$, $R^{1k}$, $R^{1m}$, $R^{1n}$ and $R^{1p}$ represents the substituent having a Hammett's σp value of 0.3 or more; more preferably, at least one of $R^{1g}$, $R^{1h}$, $R^{1i}$ and $R^{1j}$ represents the substituent having a Hammett's σp value of 0.3 or more (preferably from 0.3 to 1.2); and still more preferably, $R^{1h}$ represents the substituent having a Hammett's σp value of 0.3 or more. In particular, it is preferred that $R^{1c}$ and $R^{1h}$ represent the substituent having a Hammett's σp value or 0.3 or more (preferably from 0.3 to 1.2). This is because the compound has excellent light resistance.

In the first preferred embodiment of the present invention, preferably, each of $R^{1h}$ and $R^{1n}$ is independently any one of a hydrogen atom, $COOR^r$, $CONR^s_2$, a cyano group, $CF_3$, a nitro group and $SO_3M$ (wherein M represents a hydrogen atom or an alkali metal); more preferably, $R^{1h}$ or $R^{1n}$ is a hydrogen atom; still more preferably, $R^{1h}$ and $R^{1n}$ are a hydrogen atom; and yet still more preferably, each of $R^{1g}$, $R^{1h}$, $R^{1i}$, $R^{1j}$, $R^{1k}$, $R^{1m}$, $R^{1n}$ and $R^{1p}$ represents a hydrogen atom. This is because the compound exhibits excellent light resistance.

In the first preferred embodiment of the present invention, in the compound represented by formula (1), preferably, $R^{1c}$ is a substituent having a Hammett's σp value of 0.3 or more (preferably from 0.3 to 1.2) and each of $R^{1g}$, $R^{1h}$, $R^{1i}$, $R^{1j}$, $R^{1k}$, $R^{1m}$, $R^{1n}$ and $R^{1p}$ is a hydrogen atom; and more preferably, $R^{1c}$ is any one of $COOR^r$, $CONR^s_2$, a cyano group, $CF_3$, a nitro group and $SO_3M$ (wherein M represents a hydrogen atom or an alkali metal) and each of $R^{1g}$, $R^{1h}$, $R^{1i}$, $R^{1j}$, $R^{1k}$, $R^{1m}$, $R^{1n}$ and $R^{1p}$ is a hydrogen atom. This is because the compound exhibits excellent light resistance. The Hammett's σp value is preferably from 0.3 to 1.2, more preferably from 0.35 to 1.0, still more preferably from 0.4 to 0.8.

In the second preferred embodiment of the present invention, when each of $R^{1g}$, $R^{1h}$, $R^{1i}$, $R^{1j}$, $R^{1k}$, $R^{1m}$, $R^{1n}$ and $R^{1p}$ represents a monovalent substituent, preferably, at least one of $R^{1g}$, $R^{1h}$, $R^{1i}$, $R^{1j}$, $R^{1k}$, $R^{1m}$, $R^{1n}$ and $R^{1p}$ represents the substituent having a Hammett's σp value of 0.3 or more; more preferably, at least one of $R^{1g}$, $R^{1h}$, $R^{1i}$ and $R^{1j}$ represents the substituent having a Hammett's σp value of 0.3 or more (preferably from 0.3 to 1.2); and still more preferably, $R^{1h}$ represents the substituent having a Hammett's σp value of 0.3 or more. In particular, it is preferred that $R^{1b}$ or $R^{1d}$ and $R^{1h}$ represent the substituent having a Hammett's σp value or 0.3 or more (preferably from 0.3 to 1.2). This is because the compound has excellent light resistance.

In the second preferred embodiment of the present invention, preferably, each of $R^{1h}$ and $R^{1n}$ is independently any one of a hydrogen atom, $COOR^r$, $CONR^s_2$, a cyano group, $CF_3$, a nitro group and $SO_3M$ (wherein M represents a hydrogen atom or an alkali metal); more preferably, $R^{1h}$ or $R^{1n}$ is a hydrogen atom; still more preferably, $R^{1h}$ and $R^{1n}$ are a hydrogen atom; and yet still more preferably, each of $R^{1g}$, $R^{1h}$, $R^{1i}$, $R^{1j}$, $R^{1k}$, $R^{1m}$, $R^{1n}$ and $R^{1p}$ represents a hydrogen atom. This is because the compound exhibits excellent light resistance.

In the second preferred embodiment of the present invention, in the compound represented by formula (1), preferably, $R^{1b}$ or $R^{1d}$ represents a substituent having a Hammett's σp value of 0.3 or more (preferably from 0.3 to 1.2) and each of $R^{1g}$, $R^{1h}$, $R^{1i}$, $R^{1j}$, $R^{1k}$, $R^{1m}$, $R^{1n}$ and $R^{1p}$ represents a hydrogen atom; and more preferably, $R^{1b}$ or $R^{1d}$ is any one of $COOR^r$, $CONR^s_2$, a cyano group, $CF_3$, a nitro group and $SO_3M$ (wherein M represents a hydrogen atom or an alkali metal) and each of $R^{1g}$, $R^{1h}$, $R^{1i}$, $R^{1j}$, $R^{1k}$, $R^{1m}$, $R^{1n}$ and $R^{1p}$ is a hydrogen atom. This is because the compound exhibits excellent light resistance. The Hammett's σp value is preferably from 0.3 to 1.2, more preferably from 0.35 to 1.0, still more preferably from 0.4 to 0.8.

The compound represented by formula (1) preferably has a pKa of −5.0 to −7.0, more preferably −5.2 to −6.5, still more preferably −5.4 to −6.0.

Specific examples of the compound represented by formula (1) are illustrated below, but the present invention is not limited thereto.

In specific examples, Me indicates a methyl group, Ph indicates a phenyl group, and $-C_6H_{13}$ indicates an n-hexyl.

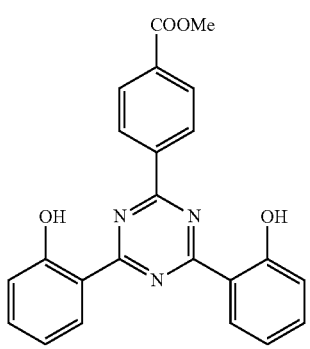
(1)
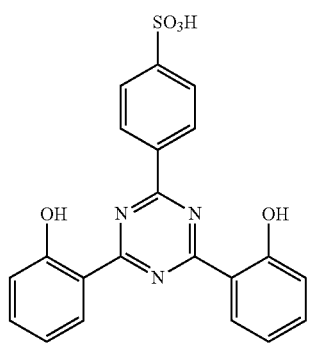
(7)
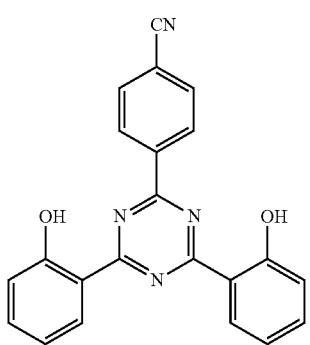
(2)
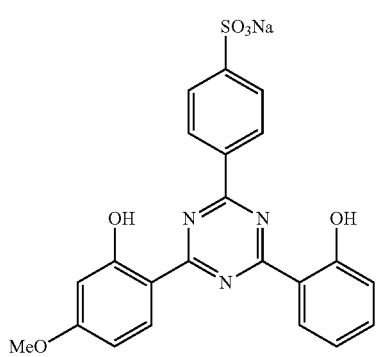
(8)
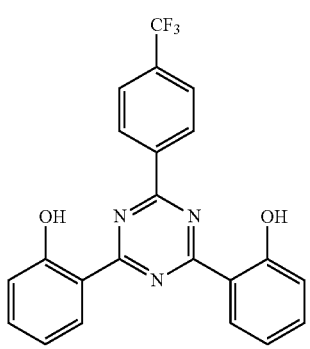
(3)
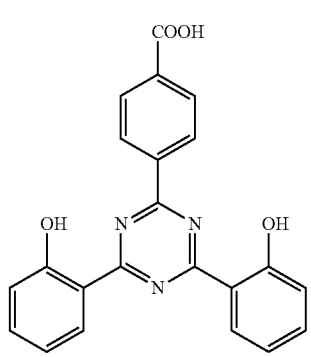
(9)
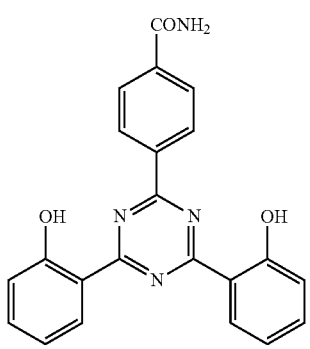
(5)
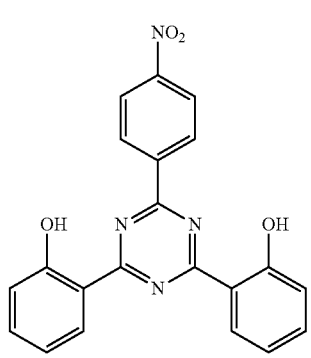
(10)

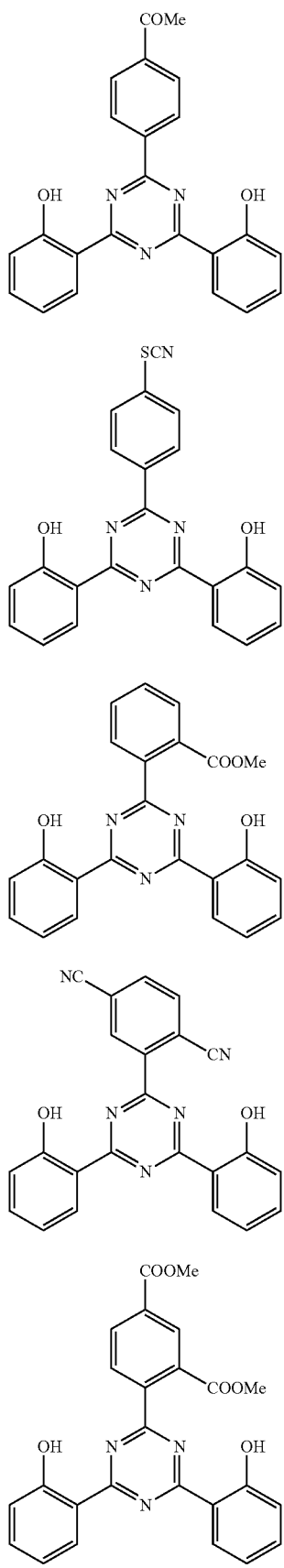
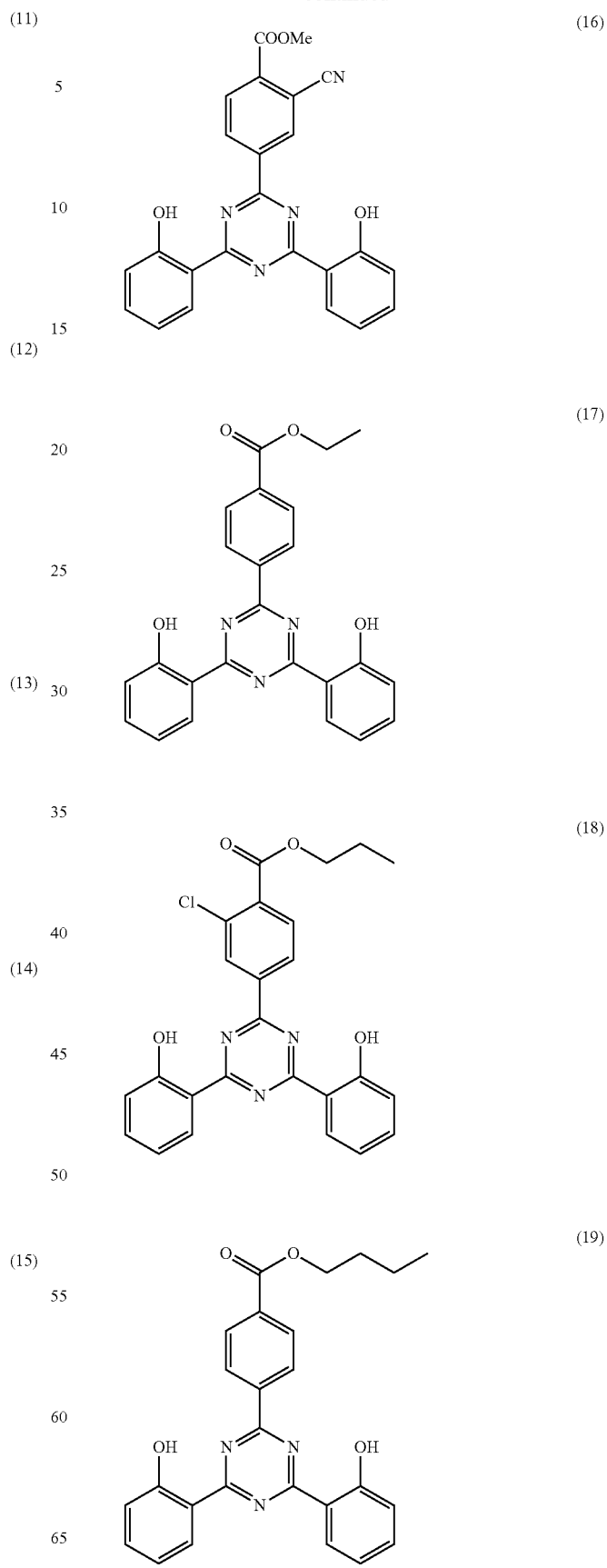

(20) 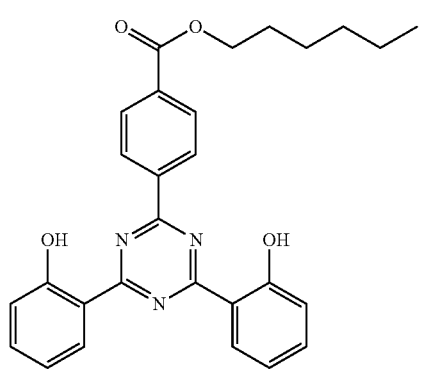
(21) 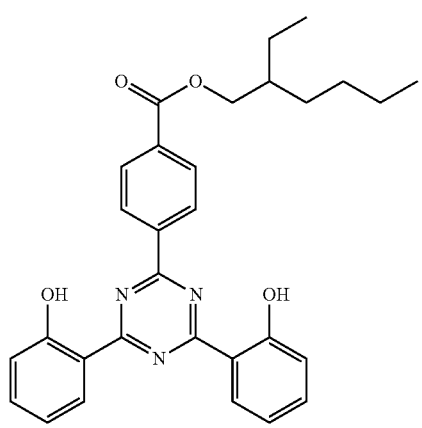
(22) 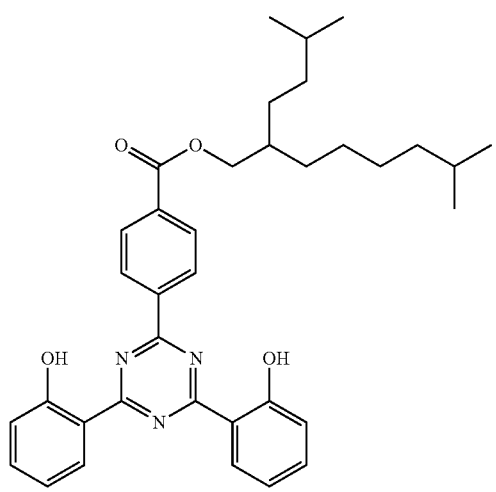
(23) 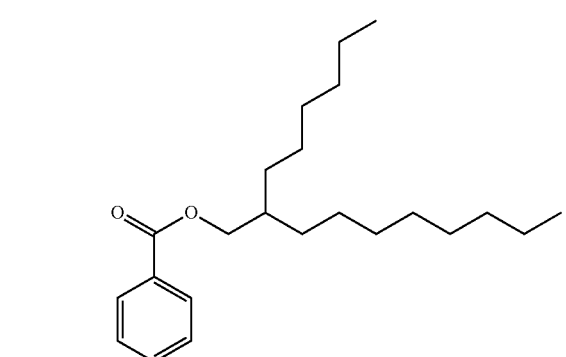
(24) 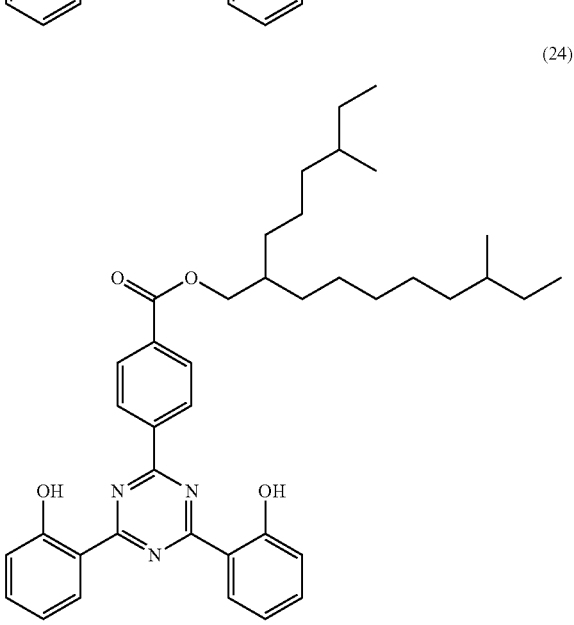
(25) 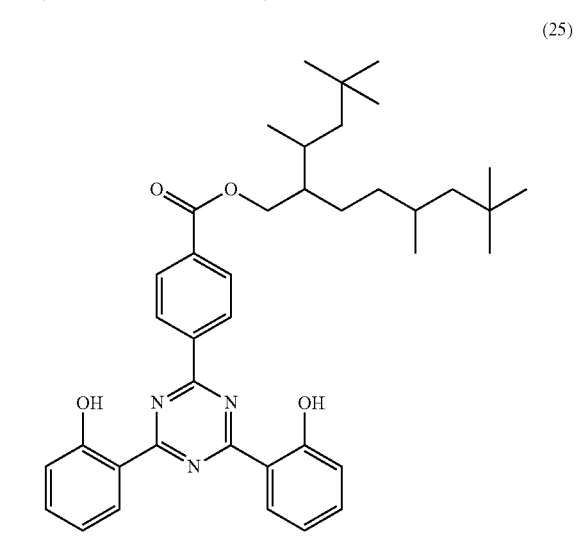

(26)
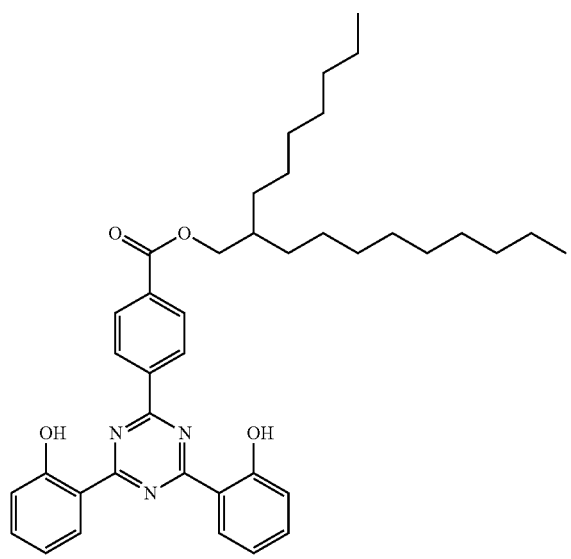
(27)
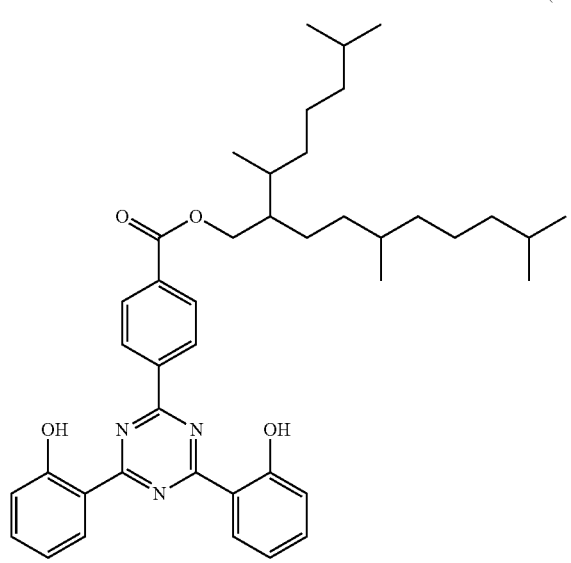
(28)
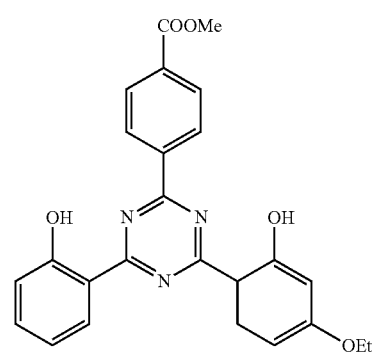
(29)
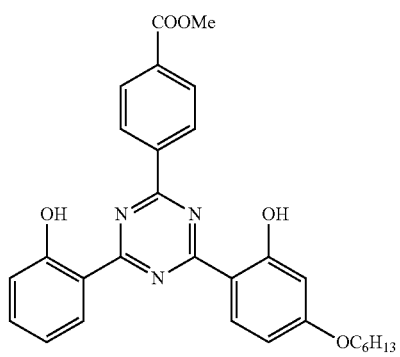
(30)
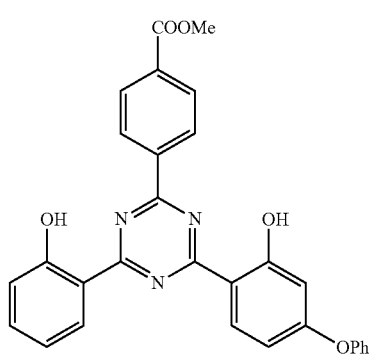
(31)
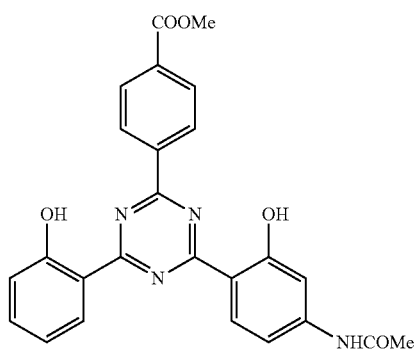
(32)
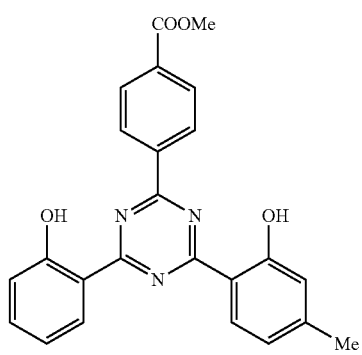

-continued
(33)
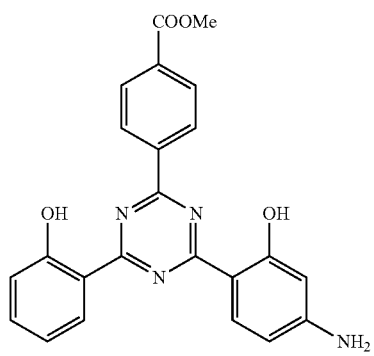
(34)
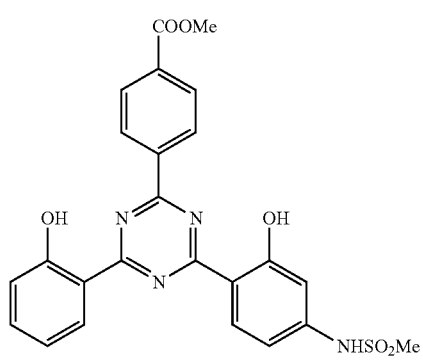
(35)
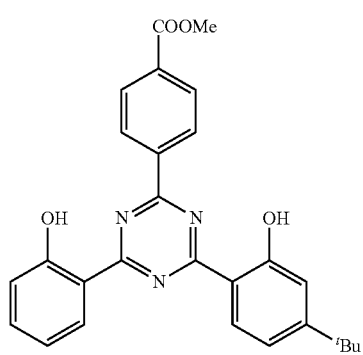
(36)
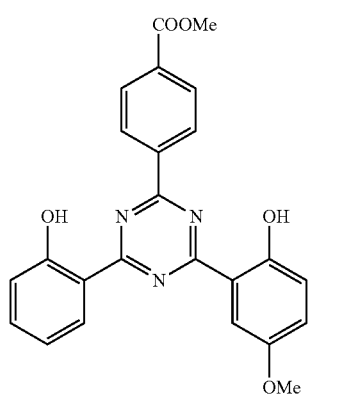
-continued
(37)
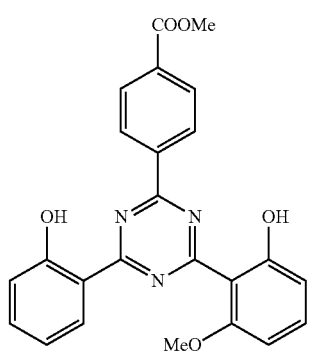
(38)
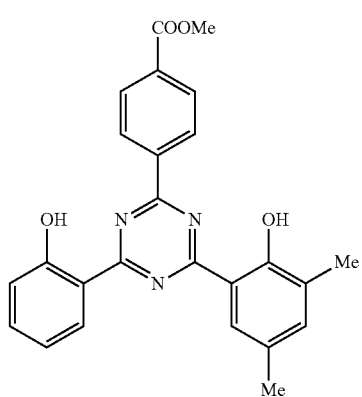
(39)
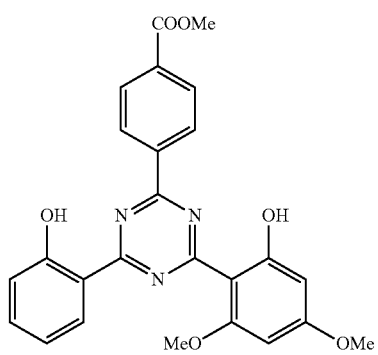
(40)
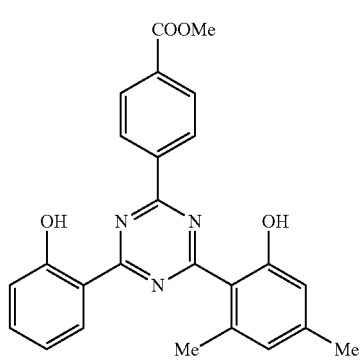

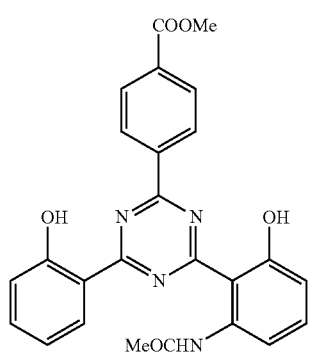
(41)
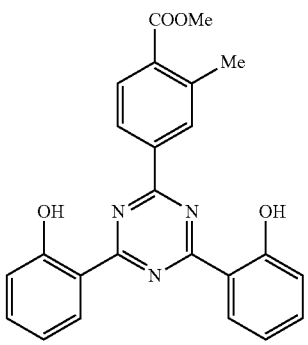
(45)
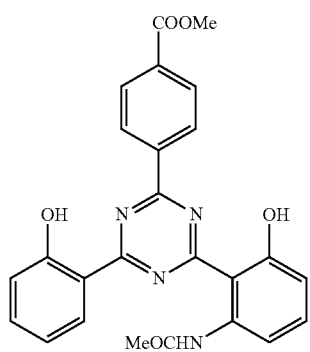
(42)
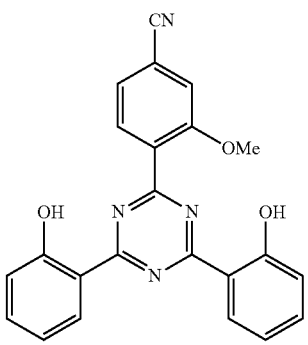
(46)
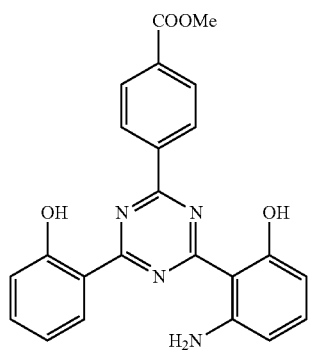
(43)
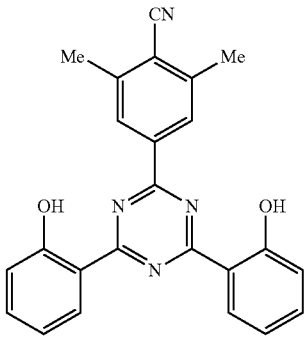
(47)
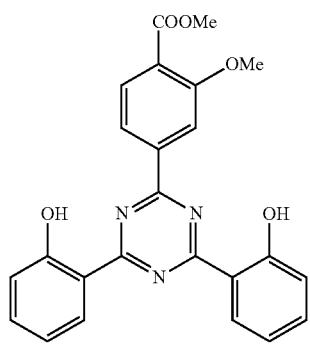
(44)
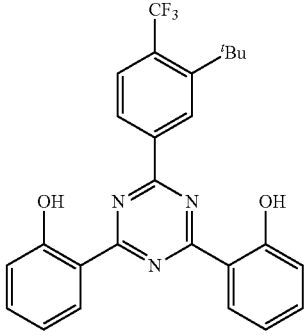
(48)

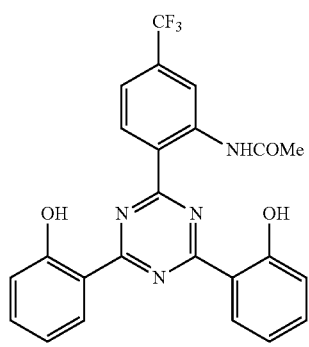
(49)
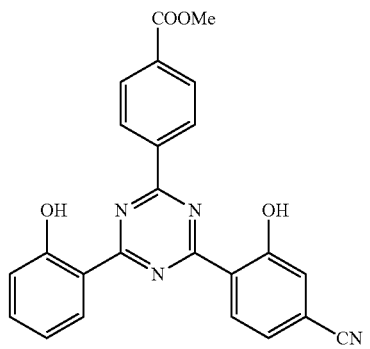
(56)
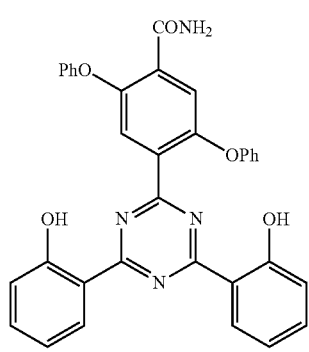
(50)
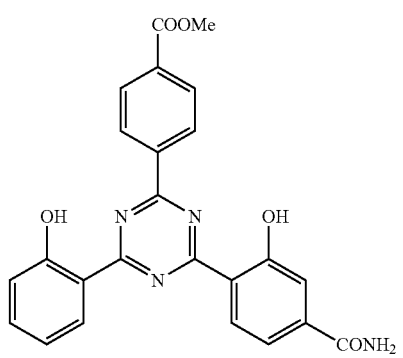
(57)
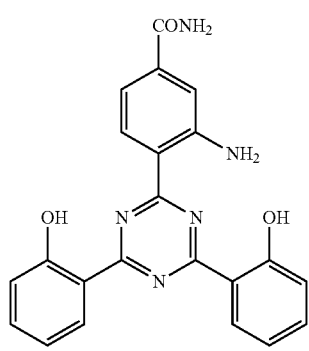
(51)
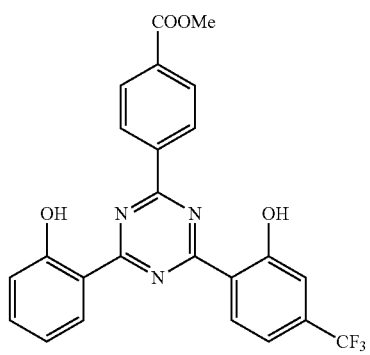
(58)
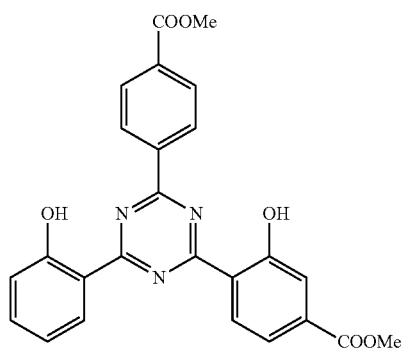
(55)
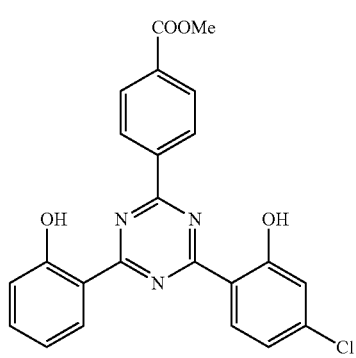
(59)

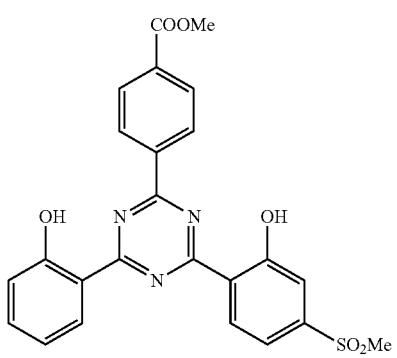
(60)
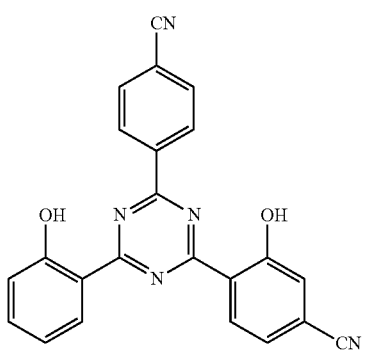
(61)
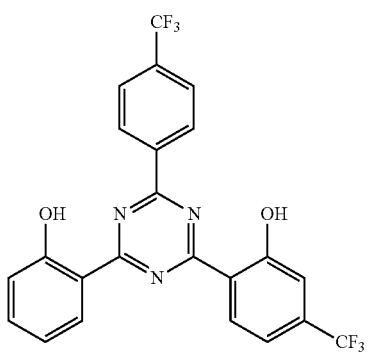
(62)
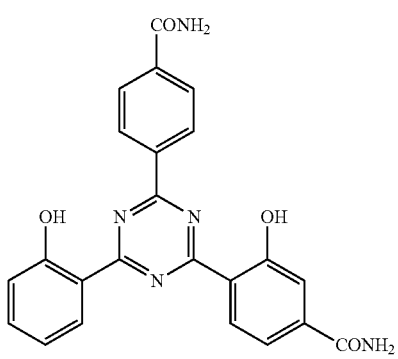
(63)
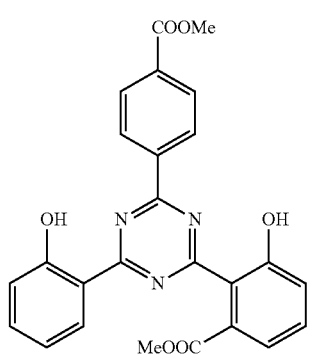
(64)
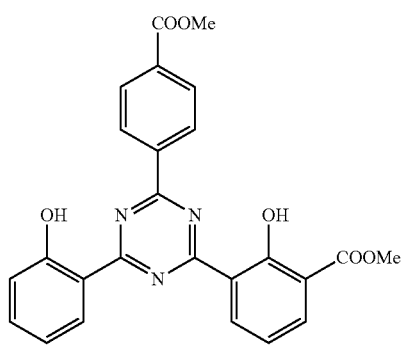
(65)
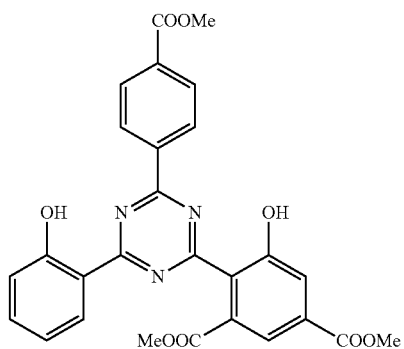
(66)
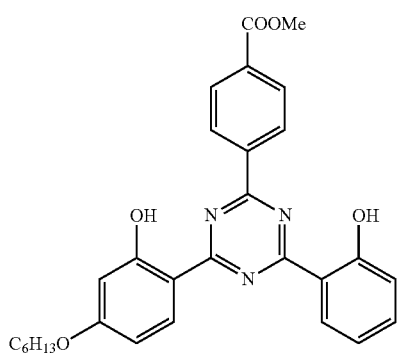
(67)

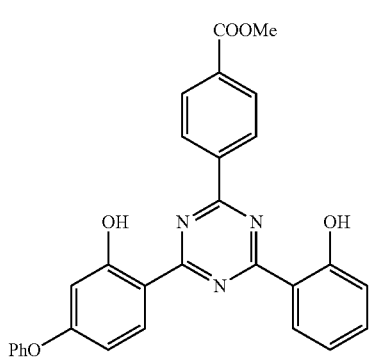
(68)
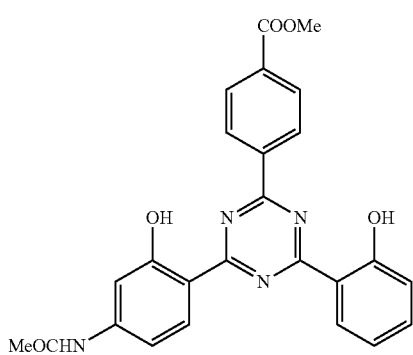
(69)
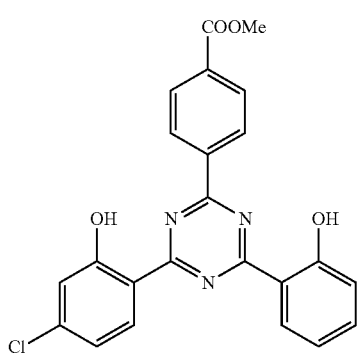
(70)
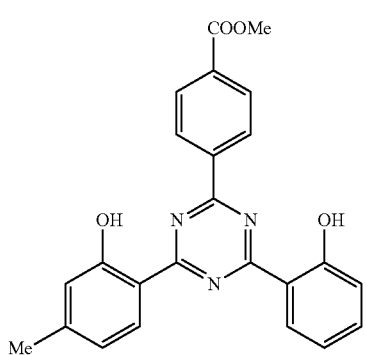
(71)
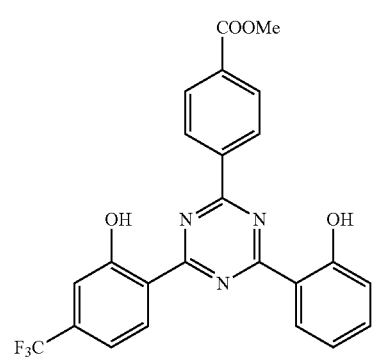
(72)
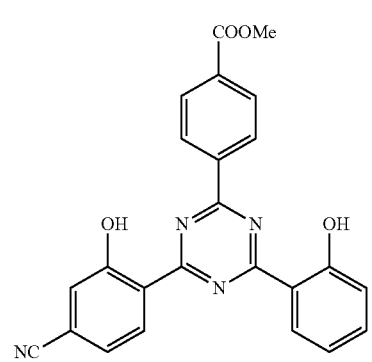
(73)
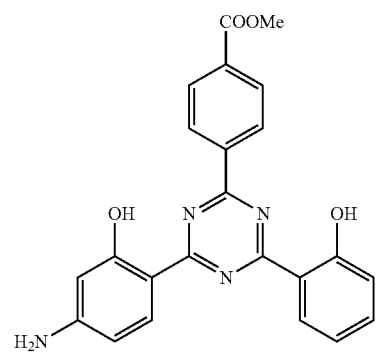
(74)
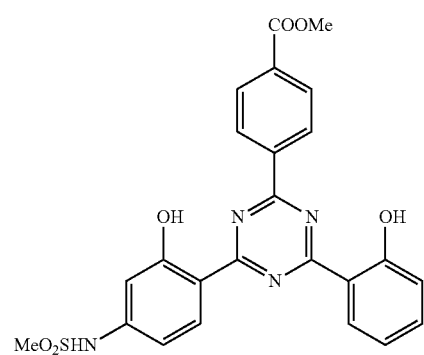
(75)

(76) 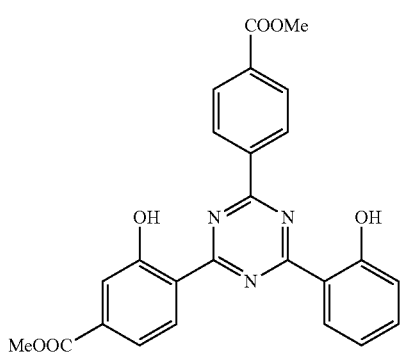
(77) 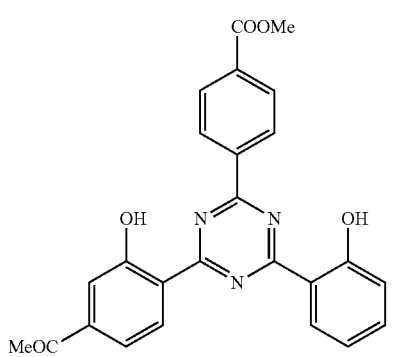
(78) 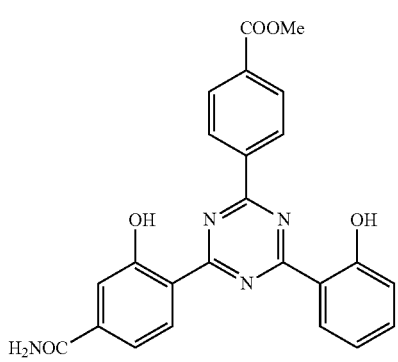
(79) 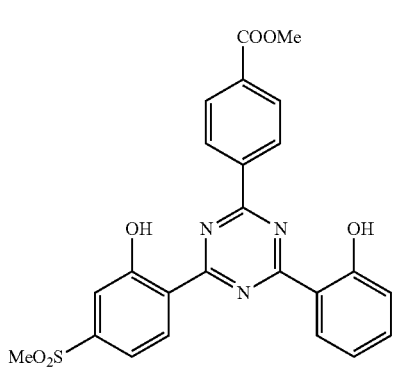
(80) 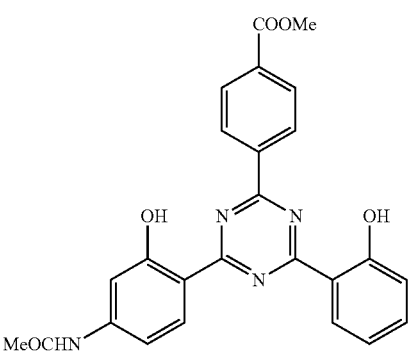
(81) 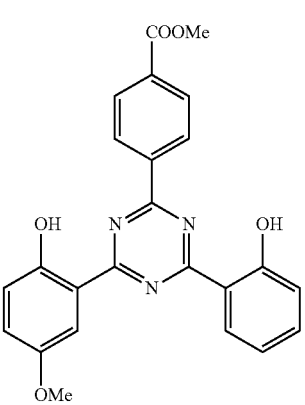
(82) 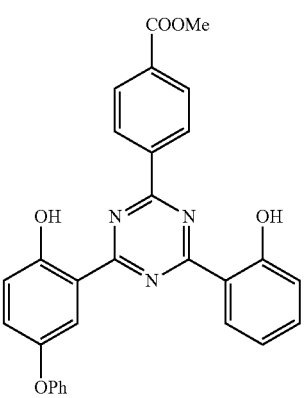
(83) 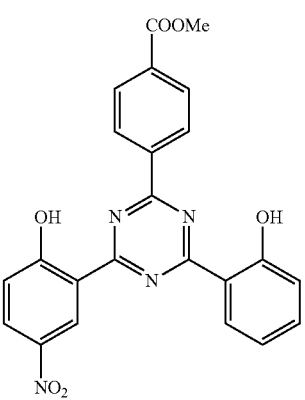

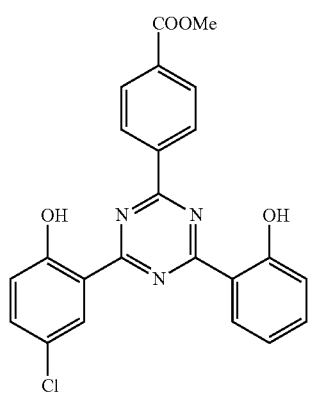
(84)
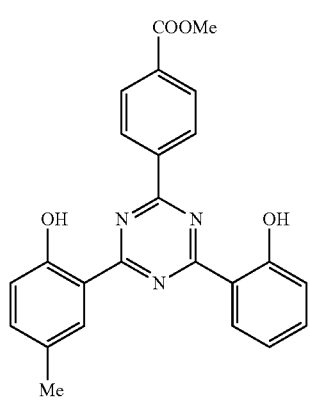
(85)
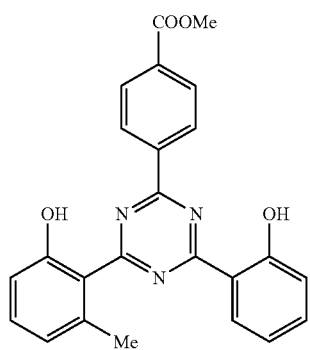
(86)
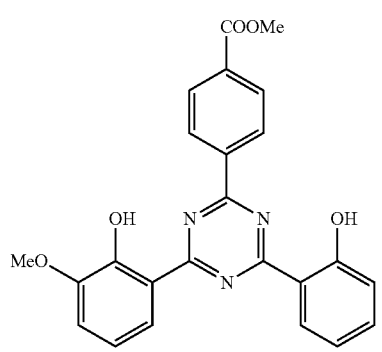
(87)
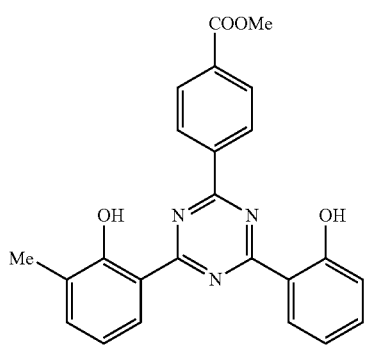
(88)
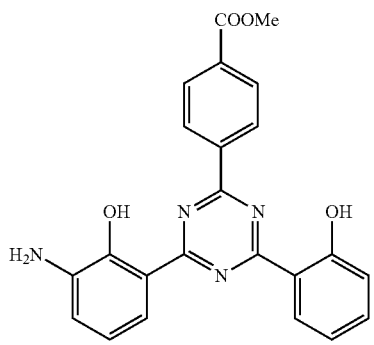
(89)
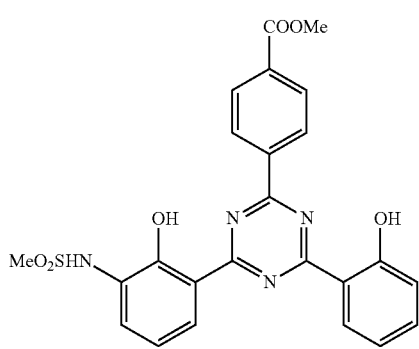
(90)
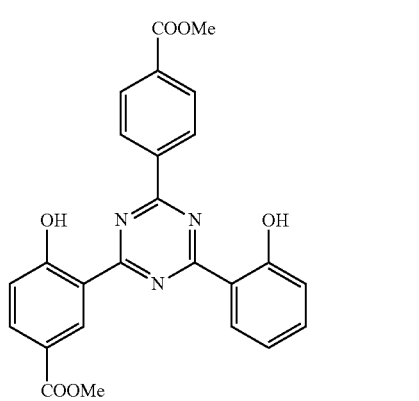
(91)

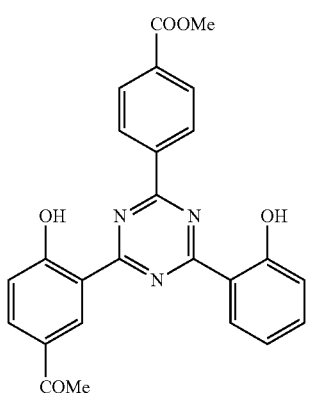 (92)
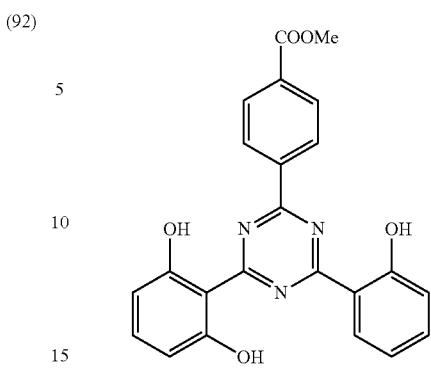 (96)
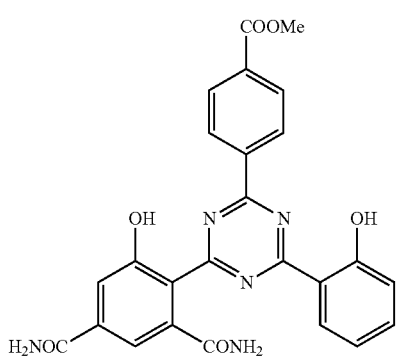 (93)
(97)
(94)
(98)
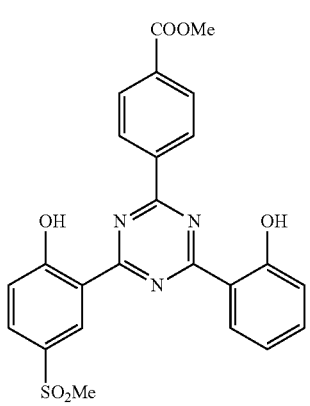 (95)
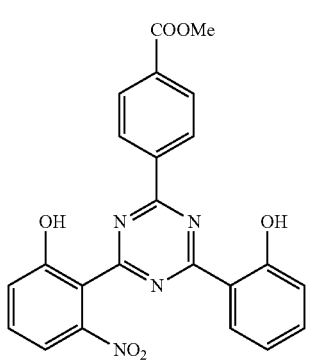
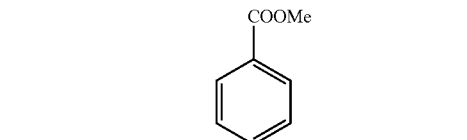 (99)

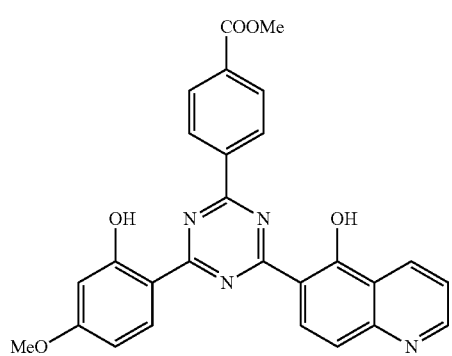
(100)
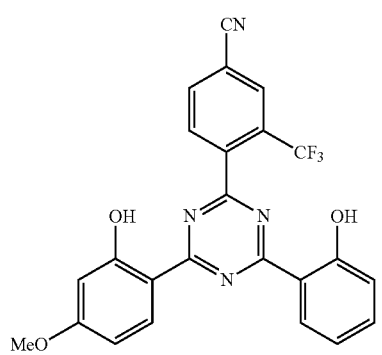
(101)
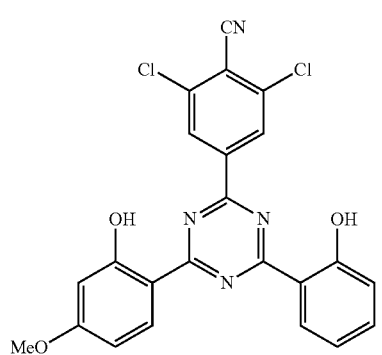
(102)
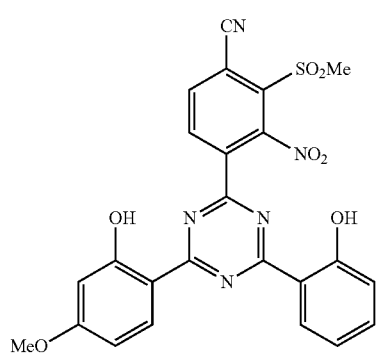
(103)
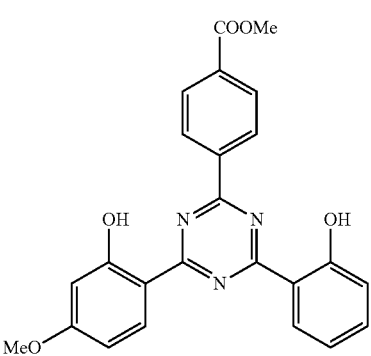
(104)
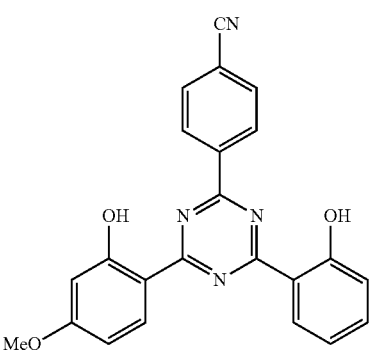
(105)
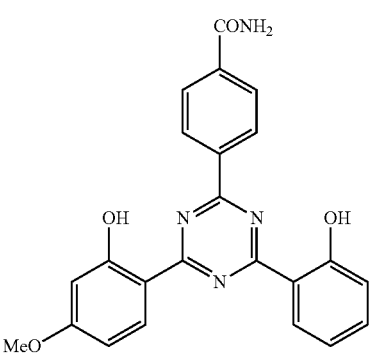
(107)
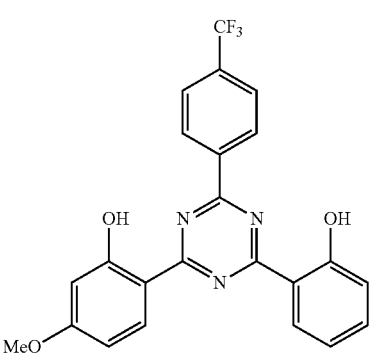
(108)

(109) 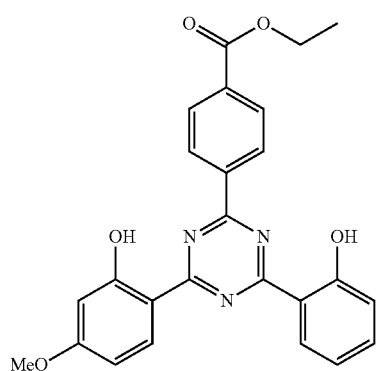
(110) 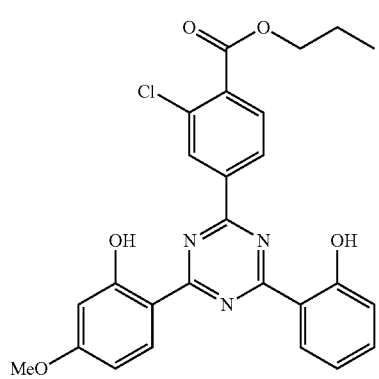
(111) 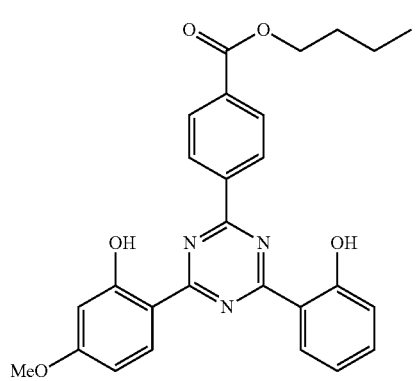
(112) 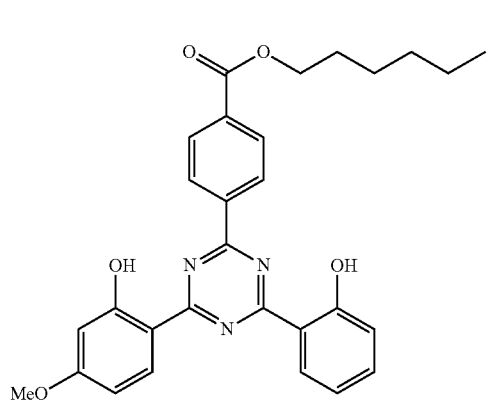
(113) 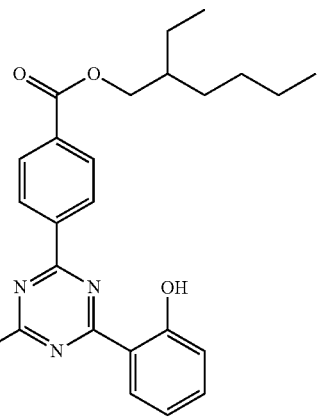
(114) 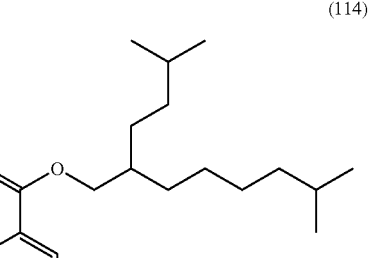
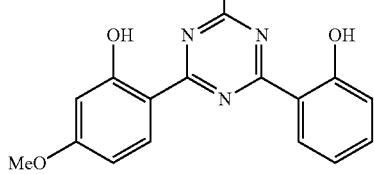
(115) 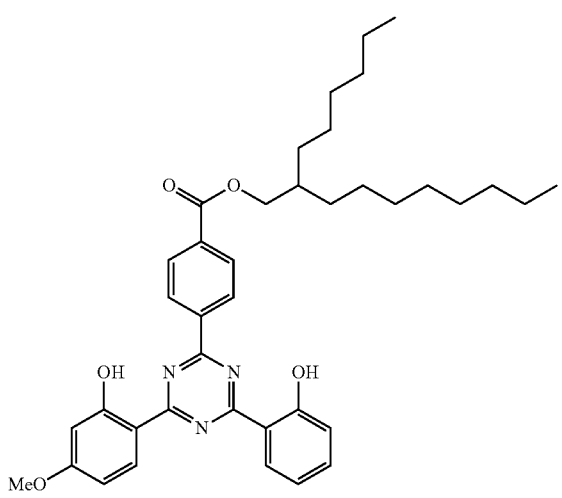

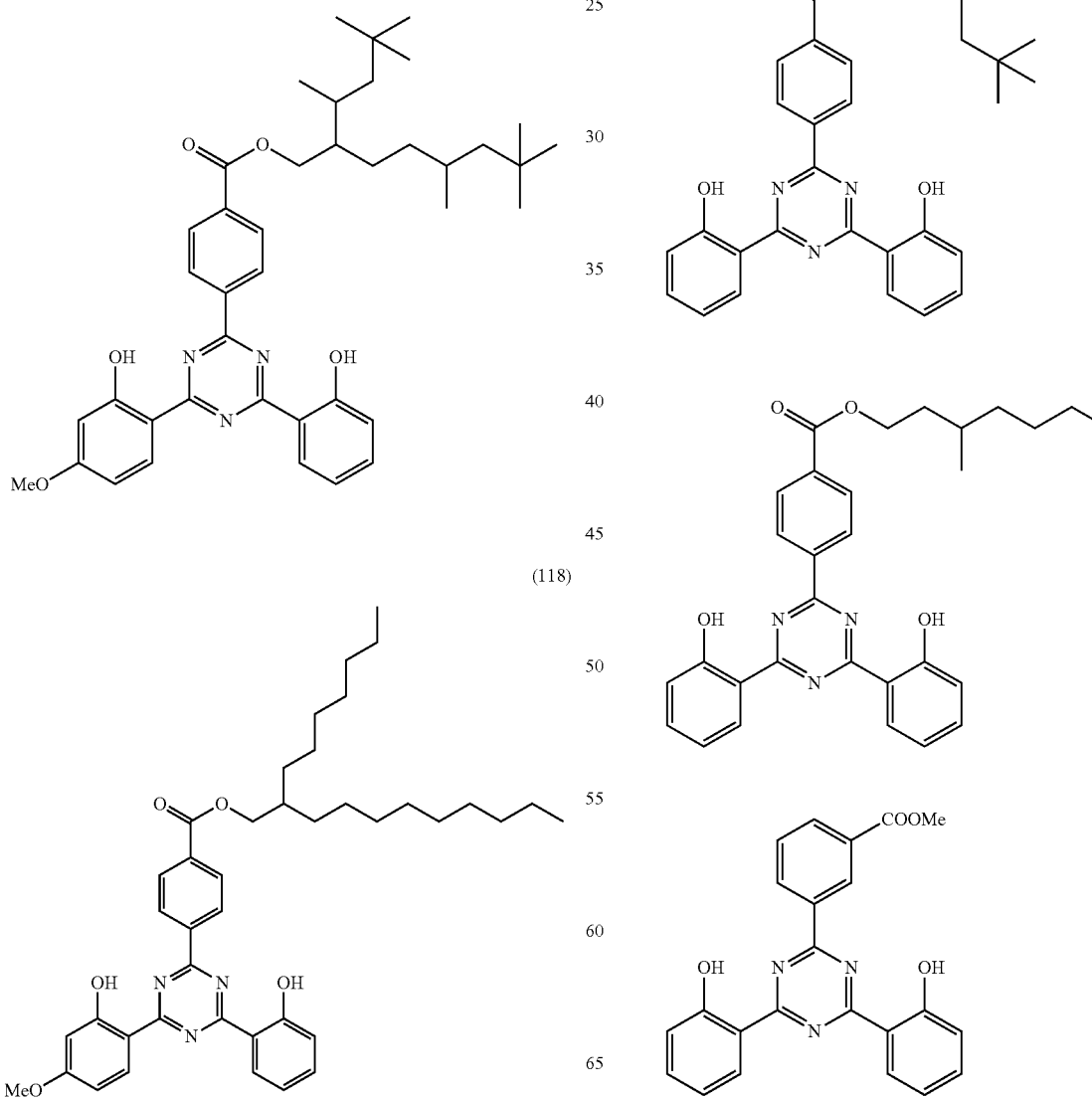

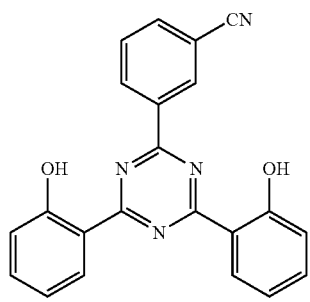 (m-2)
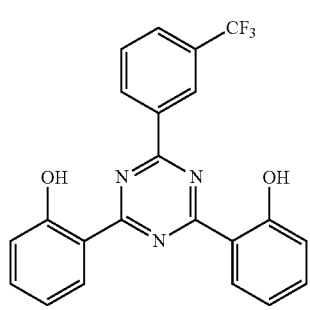 (m-3)
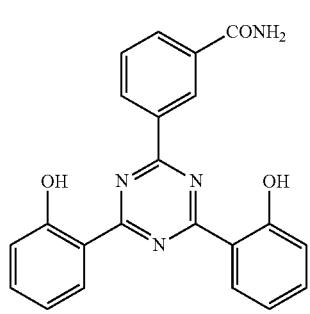 (m-5)
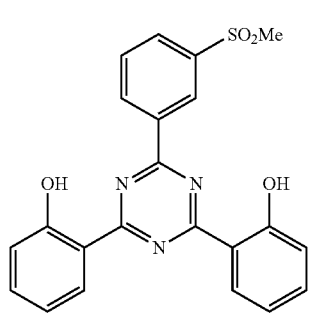 (m-7)
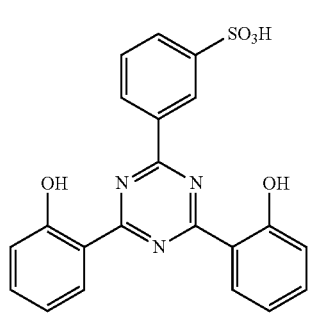 (m-8)
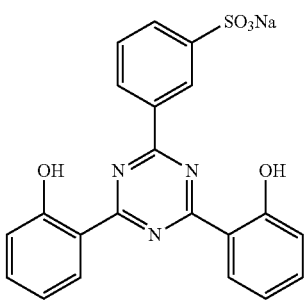 (m-9)
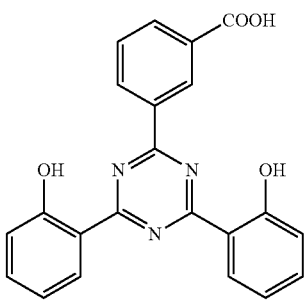 (m-10)
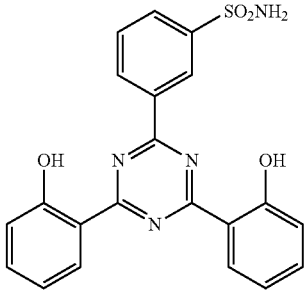 (m-11)
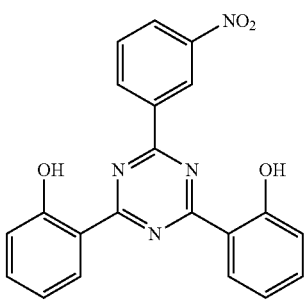 (m-12)
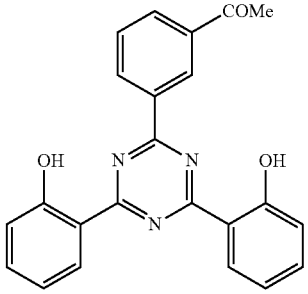 (m-13)

(m-14)
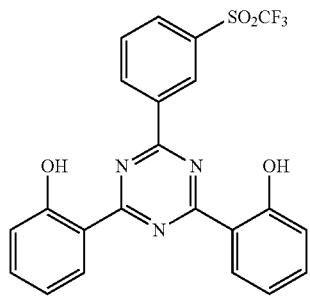
(m-15)
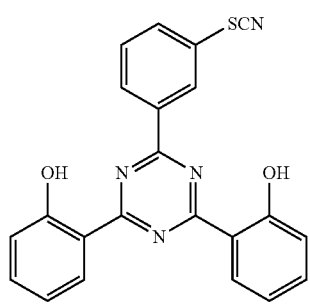
(m-16)
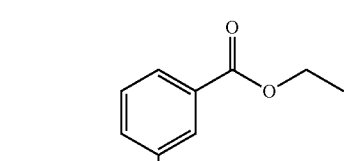
(m-17)
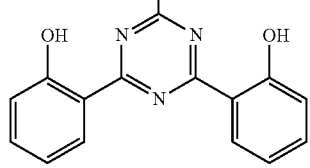
(m-18)
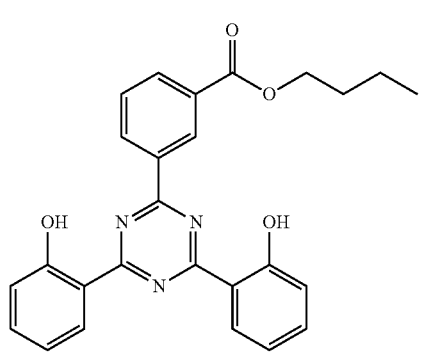
(m-19)
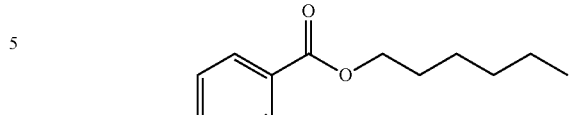
(m-20)
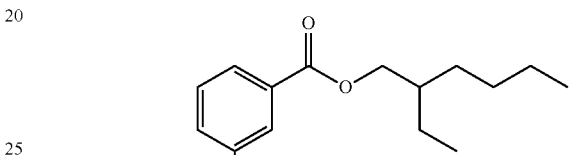
(m-21)
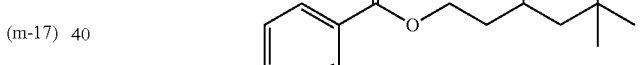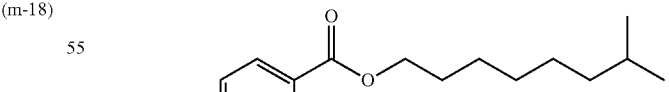
(m-22)
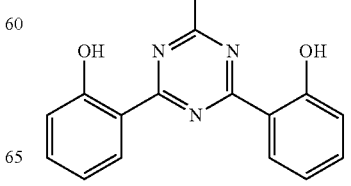

(m-23)
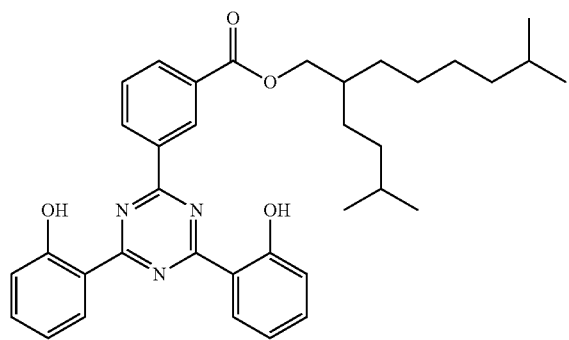
(m-24)
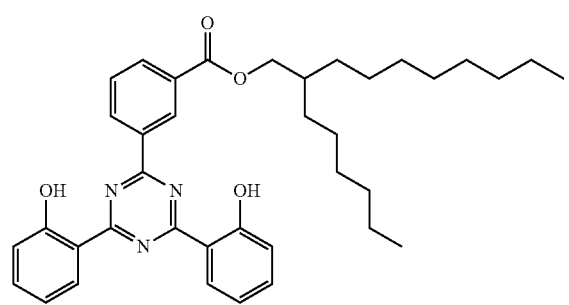
(m-25)
(m-26)
(m-27)
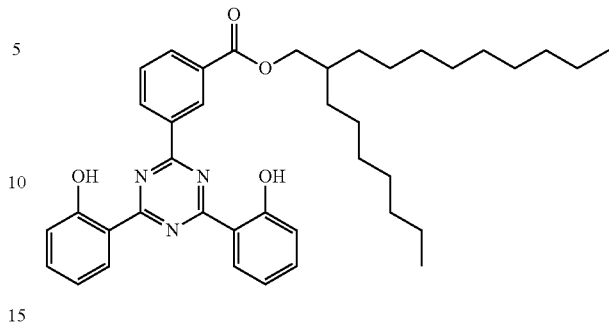
(m-28)
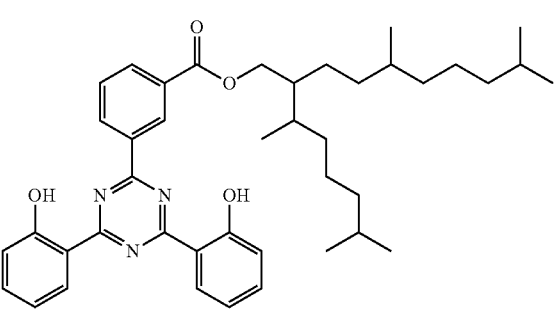
(m-29)
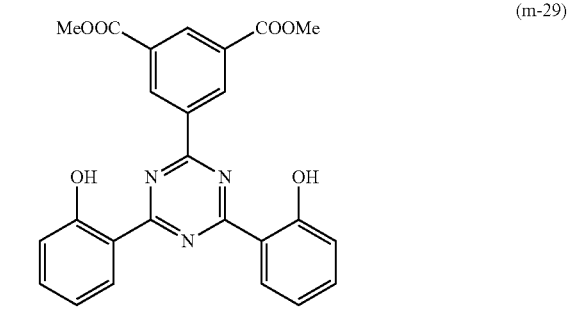
(m-30)
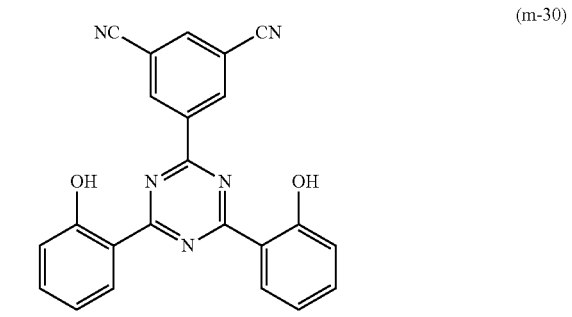
(m-31)
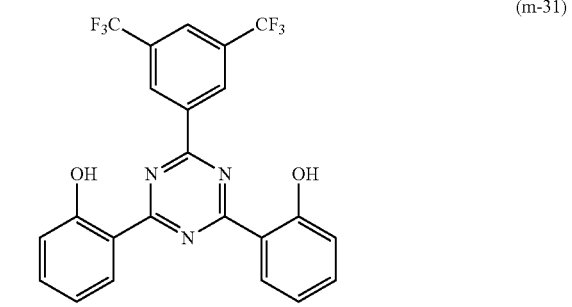

(m-33) 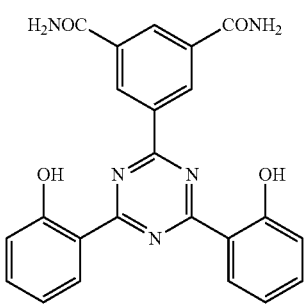
(m-35) 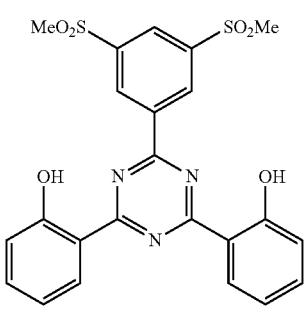
(m-36) 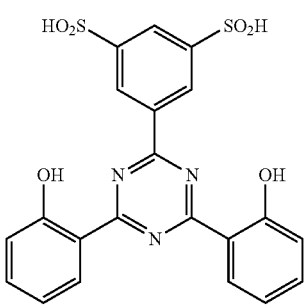
(m-37) 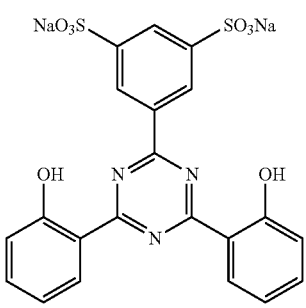
(m-38) 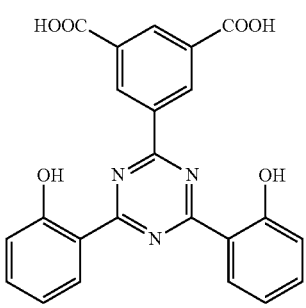
(m-39) 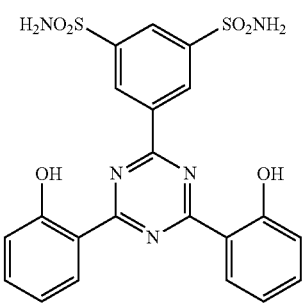
(m-40) 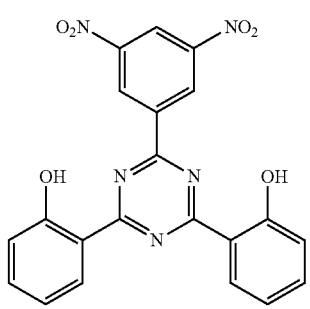
(m-41) 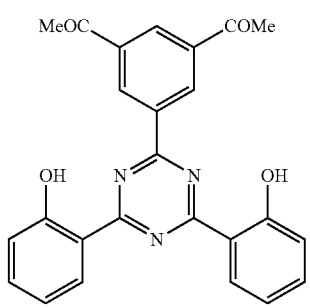
(m-42) 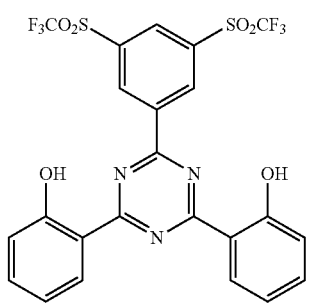
(m-43) 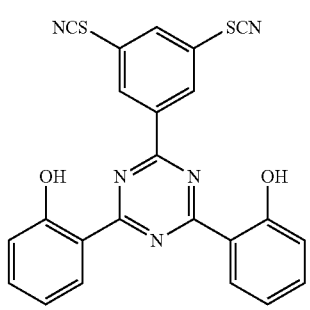

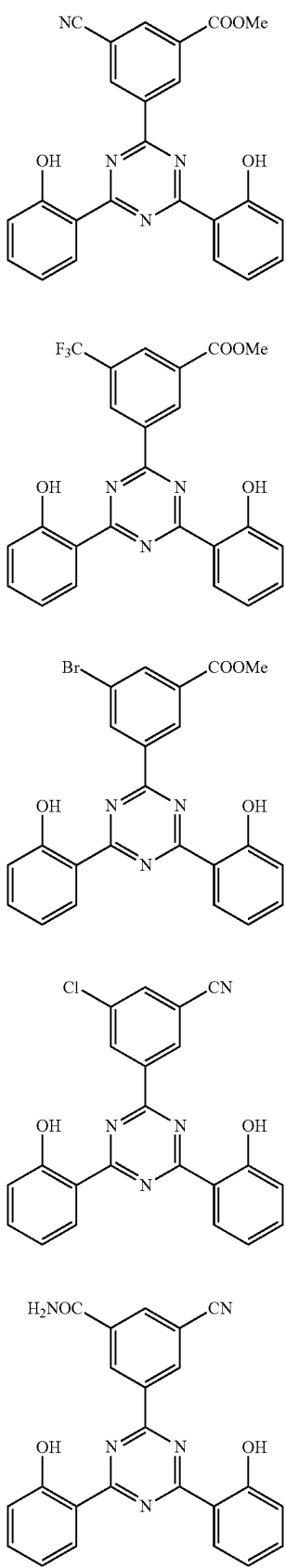
(m-44)
(m-45)
(m-46)
(m-47)
(m-48)
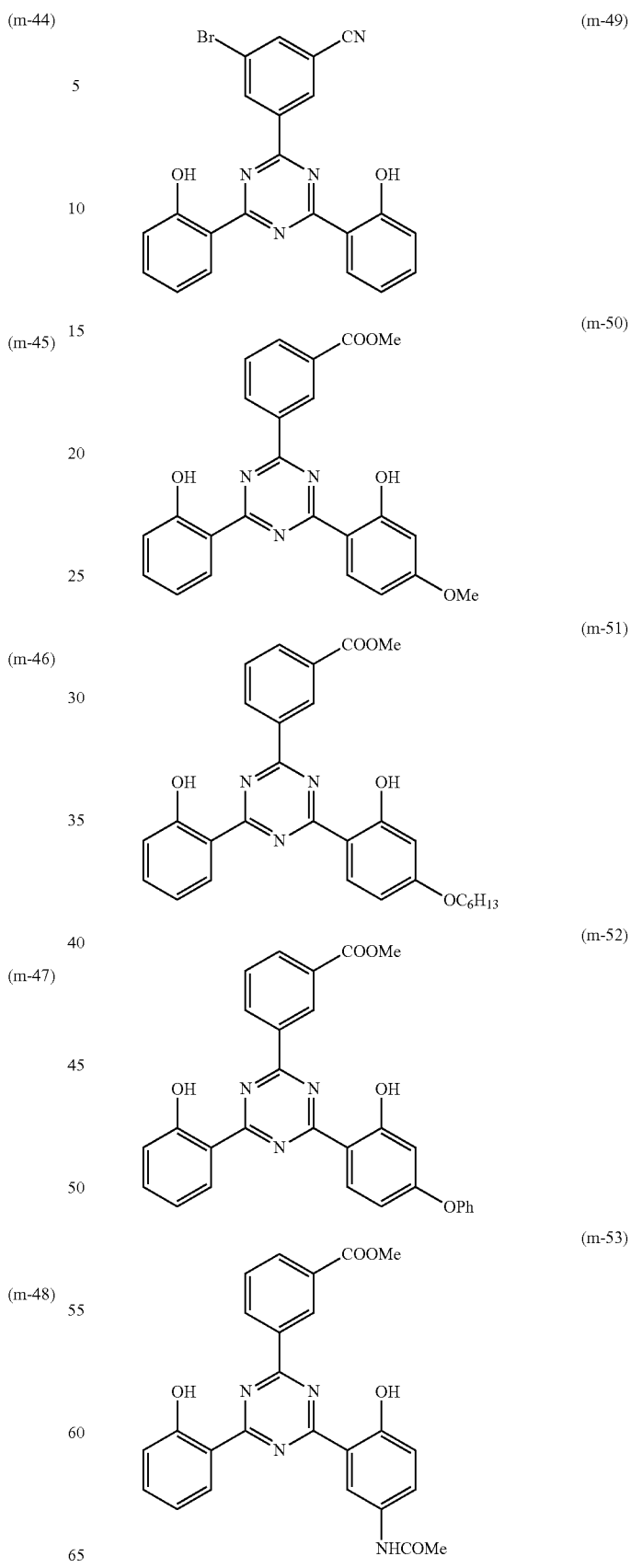
(m-49)
(m-50)
(m-51)
(m-52)
(m-53)

(m-54) 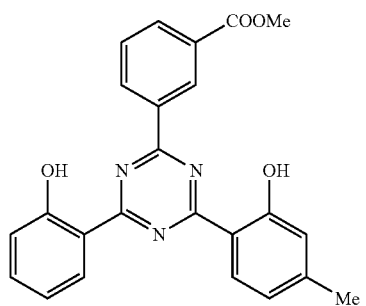
(m-55) 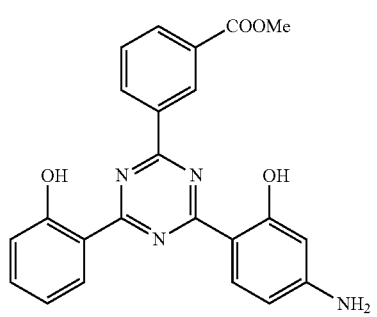
(m-56) 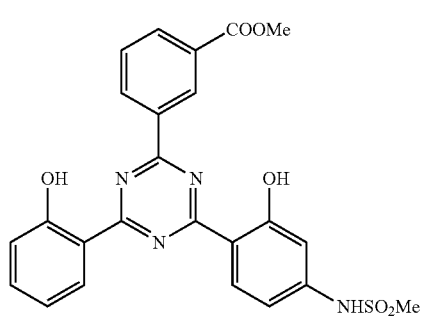
(m-57) 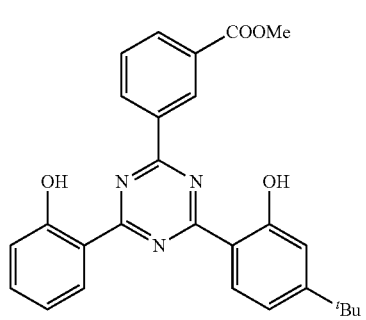
(m-58) 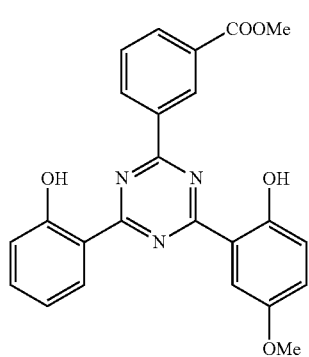
(m-59) 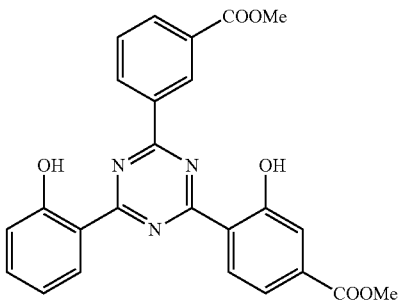
(m-60) 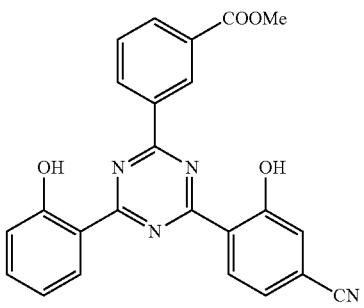
(m-61) 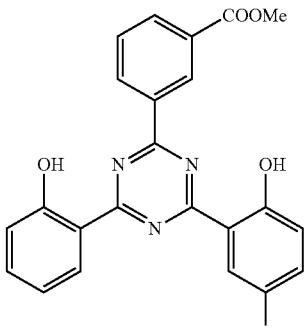
(m-62) 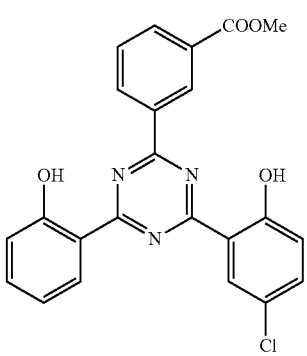
(m-63) 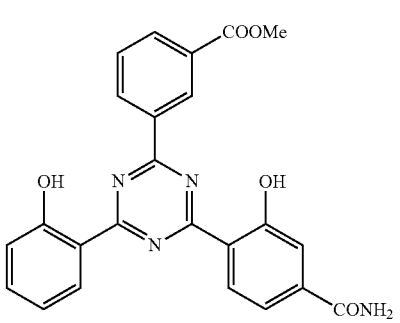

(m-64) 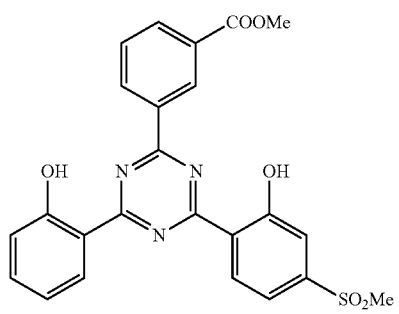
(m-65) 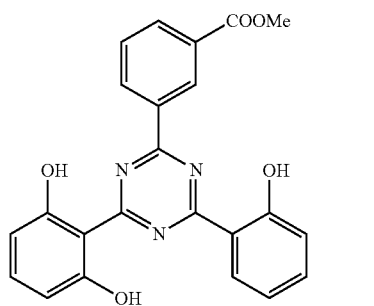
(m-66) 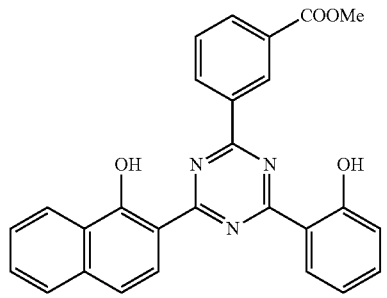
(m-67) 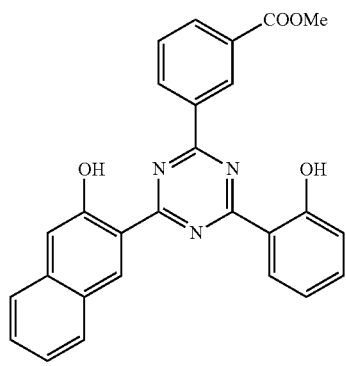
(m-68) 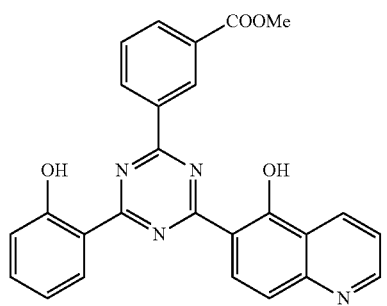
(m-69) 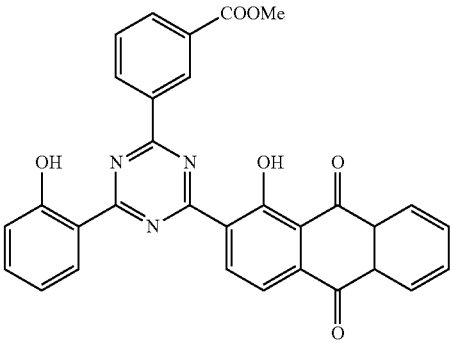
(m-70) 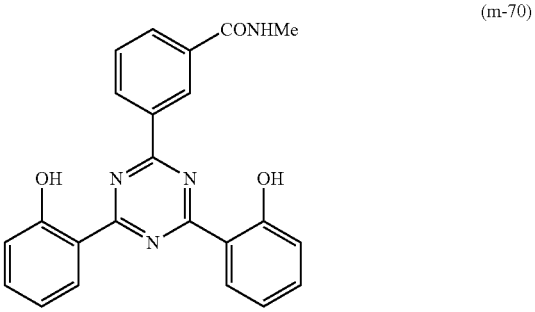
(m-71) 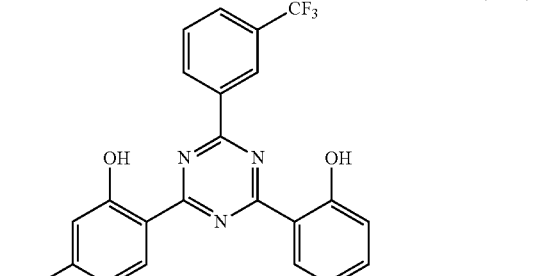
(m-72) 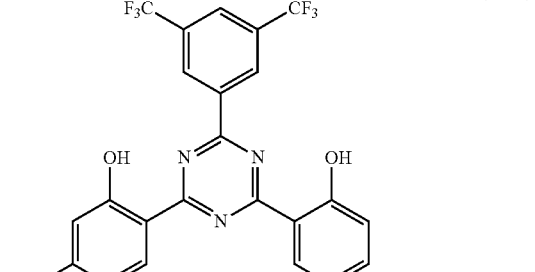
(m-73) 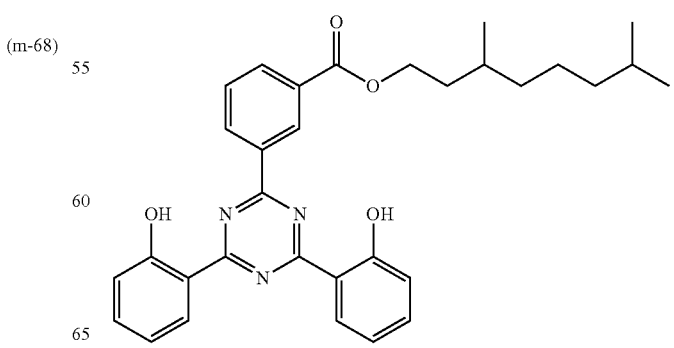

The compound represented by formula (1) may take a tautomer form depending on the structure and the environment. In the present invention, the compound is described by referring to one representative form, but a tautomer different from the compound described in the present invention is also included in the compound of the present invention.

The compound represented by formula (1) may contain an isotope (e.g., $^2H$, $^3H$, $^{13}C$, $^{15}N$, $^{17}O$, or $^{18}O$).

The compound represented by formula (1) can be synthesized by an arbitrary method.

For example, the compound can be synthesized by referring to known patent documents or non-patent documents such as JP-A-7-188190, JP-A-11-315072, JP-A-2001-220385, and *Senryo to Yakuhin* (*Dyes and Chemicals*), Vol. 40, No. 12, pp. 325-339 (1995). Specifically, Compound (16) can be synthesized by reacting salicylamide with 3,5-bis(trifluoromethyl)benzoyl chloride and 2-hydroxybenzamidine hydrochloride or by reacting salicylamide with salicylic acid and 3,5-bis(trifluoromethyl)benzamidine hydrochloride.

The compound of the present invention is particularly suited for stabilizing an organic material against damage by light, oxygen or heat. Above all, the compound represented by formula (1) of the present invention can be suitably used as a light stabilizer, particularly, an ultraviolet absorber.

[Ultraviolet Absorber]

The compound represented by formula (1) of the present invention is useful as an ultraviolet absorber.

The ultraviolet absorber represented by formula (1) is described below:

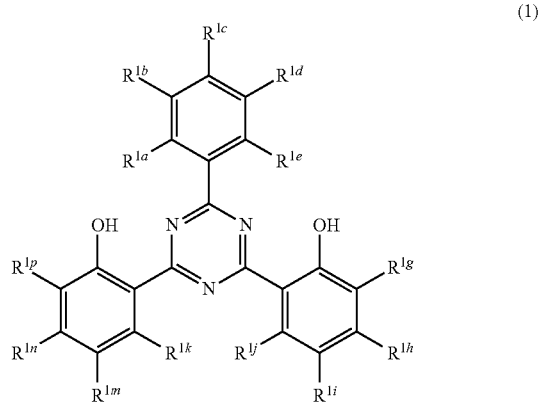

(1)

wherein each of $R^{1a}$, $R^{1b}$, $R^{1c}$, $R^{1d}$ and $R^{1e}$ independently represents a hydrogen atom or a monovalent substituent excluding OH, provided that at least one substituent represents a substituent having a Hammett's σp value of 0.3 or more and substituents may combine with each other to form a ring, and each of $R^{1g}$, $R^{1h}$, $R^{1i}$, $R^{1j}$, $R^{1k}$, $R^{1m}$, $R^{1n}$ and $R^{1p}$ independently represents a hydrogen atom or a monovalent substituent, provided that substituents may combine with each other to form a ring.

Preferred examples and specific examples of the ultraviolet absorber represented by formula (1) of the present invention are the same as preferred examples and specific examples of the compound represented by formula (1) of the present invention.

The ultraviolet absorber of the present invention is represented by formula (1). The ultraviolet absorber represented by formula (1) of the present invention has a substituent having a Hammett's σp value of 0.3 or more at a specific position and therefore, LUMO is stabilized by an electron-withdrawing group, so that the ultraviolet absorber can be characterized by short excitation life and excellent light resistance. With respect to use as an ultraviolet absorber, when a known triazine-based compound is used, the compound may be decreased in the ultraviolet-blocking effect during use for a long time or decomposed to cause an adverse effect such as yellowing.

In contrast, the ultraviolet absorber represented by formula (1) of the present invention has excellent light resistance and therefore, can produce an effect that even when used for a long time, the ultraviolet absorber is not reduced in the ultraviolet-blocking effect or is kept from decomposition and yellowing.

Furthermore, in the ultraviolet absorber represented by formula (1), each of $R^{1a}$, $R^{1c}$ and $R^{1e}$ represents a hydrogen atom, each of $R^{1b}$ and $R^{1d}$ independently represents a hydrogen atom or a substituent having a Hammett's σp value of 0.3 or more, and at least one of $R^{1b}$ and $R^{1d}$ is a substituent having a Hammett's σp value of 0.3 or more, so that LUMO can be stabilized by an electron-withdrawing group and the excitation life can be shortened. Also, the symmetry of the compound structure is lost, and the ultraviolet absorber comes to have excellent light resistance and solvent solubility.

One ultraviolet absorber represented by formula (1) may be used, or two or more thereof may be used in combination.

The ultraviolet absorber of the present invention may be used in any form. Examples thereof include a liquid dispersion, a solution, and a resin composition.

The maximum absorption wavelength of the ultraviolet absorber of the present invention is not particularly limited but is preferably from 250 to 400 nm, more preferably from 280 to 380 nm, and the half-value width is preferably from 20 to 100 nm, more preferably from 40 to 80 nm.

The maximum absorption wavelength and half-value width specified in the present invention can be easily measured by one skilled in the art. The measuring method is described, for example, in *Dai 4-han Jikken Kagaku Koza 7, Bunko II* (*4th ed., Experimental Chemistry Course 7, Spectroscopy II*), pp. 180-186, edited by Chemical Society of Japan, Maruzen (1992). Specifically, the sample is dissolved in an appropriate solvent and the spectrum is measured in a spectrophotometer by using two quartz-made or glass-made cells, that is, one cell for the sample and another cell for control, whereby the maximum absorption wavelength and half-value width are determined. The properties required of the solvent used here are, for example, to dissolve the sample, have no absorption in the measurement wavelength region, cause little interaction with the solute molecule, and be not excessively volatile. An arbitrary solvent may be used as long as the requirements above are satisfied. In the present invention, the measurement is performed using ethyl acetate (EtOAc) as the solvent.

The maximum absorption wavelength and half-value width of the compound in the present invention are a value determined using a quartz cell having an optical path length of 10 mm after preparing a solution in a concentration of about $5 \times 10^{-5}$ mol·dm$^{-3}$ by using ethyl acetate as the solvent.

The spectral half-value width is described, for example, in *Dai 4-han Jikken Kagaku Koza 3, Kihon Sosa III* (*4th ed., Experimental Chemistry Course 3, Basic Operation III*), page 154, edited by Chemical Society of Japan, Maruzen (1991). Incidentally, the half-value width is described in the literature above by labeling the abscissa with a wavenumber scale, but the half-value width used in the present invention is a value when the axis is marked with a wavelength scale, and the unit of the half-value width is nm. Specifically, the half-value width indicates the width of the absorption band of ½ of the absorbance at the maximum absorption wavelength and is used as an indicator of the absorption spectral shape. A spectrum with a small half-value width is a sharp spectrum, and a spectrum with a large half-value width is a broad spectrum. The ultraviolet absorbing compound giving a broad spectrum has absorption also in a broad region on the longer wavelength side than the maximum absorption wavelength and therefore, in order to effectively block light in the long-wavelength ultraviolet range with no yellow tinting, an ultraviolet absorbing compound giving a spectrum with a small half-value width is preferred.

As described in Sumio Tokita, *Kagaku Seminar 9, Color Chemistry* (*Chemistry Seminar 9, Color Chemistry*), pp. 154-155, Maruzen (1982), the absorption intensity of light, namely, the oscillator intensity, is proportional to the integral of the molar extinction coefficient and when the absorption spectrum has good symmetry, the oscillator intensity is proportional to the product of the absorbance at the maximum absorption wavelength and the half-value width (here, the half-value width is a value when the axis is marked with a wavelength scale). This indicates that as long as the value of transition moment is the same, a compound having a spectrum with a small half-value width exhibits large absorbance at the maximum absorption wavelength. Use of such an ultraviolet absorbing compound is advantageous in that light in the region around the maximum absorption wavelength can be effectively blocked only by its use in a small amount, but absorbance at the wavelength a little distance away from the maximum absorption wavelength rapidly decreases, and this makes it impossible to block light over a wide region.

The molar extinction coefficient at the maximum absorption wavelength of the ultraviolet absorber is preferably 20,000 or more, more preferably 30,000 or more, still more preferably 50,000 or more. With a molecular extinction coefficient of 20,000 or more, the absorption efficiency per mass of the ultraviolet absorber is sufficiently high and the amount of the ultraviolet absorber used for completely absorbing light in the ultraviolet region can be reduced. This is preferred also from the standpoint of preventing irritation to skin or accumulation in vivo and hardly causing bleed-out. Incidentally, the molar extinction coefficient used here is based on the definition described, for example, in *Shin-han Jikken Kagaku Koza 9, Bunseki Kagaku [II]* (*New Edition, Experimental Chemistry Course 9, Analytical Chemistry [II]*), page 244, edited by Chemical Society of Japan, Maruzen (1977) and can be determined together at the time of determining the above-described maximum absorption wavelength and half-value width.

The ultraviolet absorber of the present invention (hereinafter, sometimes simply referred to as "the ultraviolet absorber") can be used also in the state of a dispersion obtained by dispersing the ultraviolet absorber in a dispersion medium. The ultraviolet absorber dispersion containing the ultraviolet absorber of the present invention is described below.

The medium in which the ultraviolet absorber of the present invention is dispersed may be any medium. Examples thereof include water, an organic solvent, a resin, and a resin solution. These may be used individually or in combination.

Examples of the organic solvent as the dispersion medium for use in the present invention include a hydrocarbon-based solvent such as pentane, hexane and octane; an aromatic solvent such as benzene, toluene and xylene; an ether-based solvent such as diethyl ether and methyl-tert-butyl ether; an alcohol-based solvent such as methanol, ethanol and isopropanol; an ester-based solvent such as acetone, ethyl acetate and butyl acetate; a ketone-based solvent such as methyl ethyl ketone; a nitrile-based solvent such as acetonitrile and propionitrile; an amide-based solvent such as N,N-dimethylformamide, N,N-dimethylacetamide and N-methylpyrrolidone; a sulfoxide-based solvent such as dimethylsulfoxide; an amine-based solvent such as triethylamine and tributylamine; a carboxylic acid-based solvent such as acetic acid and propionic acid; a halogen-based solvent such as methylene chloride and chloroform; and a heterocyclic solvent such as tetrahydrofuran and pyridine. These solvents may be also used by combining them in an arbitrary ratio.

The resin as the dispersion medium for use in the present invention includes a thermoplastic resin and a thermosetting resin, which have been heretofore used for the production of various conventionally known shape-formed articles, sheets, films and the like. Examples of the thermoplastic resin include a polyethylene-based resin, a polypropylene-based resin, a poly(meth)acrylate-based resin, a polystyrene-based resin, a styrene-acrylonitrile-based resin, an acrylonitrile-butadiene-styrene-based resin, a polyvinyl chloride-based resin, a polyvinylidene chloride-based resin, a polyvinyl acetate-based resin, a polyvinyl butyral-based resin, an ethylene-vinyl acetate-based copolymer, an ethylene-vinyl alcohol-based resin, a polyethylene terephthalate resin (PET), a polybutylene terephthalate resin (PBT), a liquid-crystal polyester resin (LCP), a polyacetal resin (POM), a polyamide resin (PA), a polycarbonate resin, a polyurethane resin, and a polyphenylene sulfide resin (PPS). These are used either as a single polymer or as a polymer blend or polymer alloy of two or more thereof. These resins are also used as a thermoplastic shape-forming material obtained by incorporating a filler such as glass fiber, carbon fiber, semi-carbonized fiber, cellulose fiber and glass bead, or a flame retardant, into a natural resin. If desired, conventionally used additives for resin, such as polyolefin-based resin fine powder, polyolefin-based wax, ethylenebisamide-based wax and metal soap, may be used individually or in combination.

Examples of the thermosetting resin include an epoxy resin, a melamine resin, and an unsaturated polyester resin. These may be used also as a thermosetting shape-forming material obtained by incorporating a filler such as glass fiber, carbon fiber, semi-carbonized fiber, cellulose fiber and glass beads, or a flame retardant, in addition to a natural resin.

In the dispersion containing the ultraviolet absorber, for example, a dispersant, an antifoaming agent, a preservative, an anti-freezing agent and a surfactant may be used in combination. In addition, the dispersion may contain an optional compound in combination. Examples thereof include a dye, a pigment, an infrared absorber, a perfume, a polymerizable compound, a polymer, an inorganic material, and a metal.

As the apparatus for obtaining a dispersion containing the ultraviolet absorber of the present invention, a high-speed stirring disperser with a high shear force, a disperser giving a high-strength ultrasonic energy, and the like can be used. Specific examples thereof include a colloid mill, a homogenizer, a capillary emulsifying machine, a liquid siren, an electromagnetic distortion ultrasonic wave generator, and an emulsifying apparatus with a Pohlmann whistle. The high-speed stirring disperser preferably used in the present invention is a disperser of a type where the main part executing the dispersing action rotates at a high speed (from 500 to 15,000 rpm, preferably 2,000 to 4,000 rpm) in a liquid, such as dissolver, polytron, homomixer, homoblender, Keddy mill and jet agitator. The high-speed stirring dispersing machine used in the present invention is sometimes called a dissolver or a high-speed impeller disperser, and a machine where, as described in JP-A-55-129136, a high-speed turning shaft is equipped with an impeller obtained by alternately folding a saw-teeth shaped plate in a vertical direction, is also a preferred example.

Preparation of an emulsified dispersion containing a hydrophobic compound may follow various processes. For example, in the case of dissolving a hydrophobic compound in an organic solvent, the hydrophobic compound is dissolved in one member or a plural-component mixture of arbitrary two or more members, selected freely from a high-boiling-point organic material, a water-immiscible low-boiling-point organic solvent and a water-miscible organic solvent, and the resulting solution is dispersed in water or an aqueous hydrophilic colloid solution in the presence of a surface active compound. The method for mixing a water-insoluble phase containing the hydrophobic compound and an aqueous phase may be performed by either a so-called forward mixing method of adding the water-insoluble phase to the aqueous phase under stirring or a reverse mixing method reversal thereto.

The ultraviolet absorber of the present invention may be also used in the solution state of being dissolved in a liquid medium. The ultraviolet absorber solution containing the ultraviolet absorber of the present invention is described below.

The liquid in which the ultraviolet absorber of the present invention is dissolved may be any liquid. Examples thereof include water, an organic solvent, a resin, and a resin solution. Examples of the organic solvent, the resin and the resin solution are the same as those described above as the dispersion medium. These may be used individually or in combination.

The solution containing the ultraviolet absorber of the present invention may additionally contain an optional component in combination. Examples include a dye, a pigment, an infrared absorber, a perfume, a polymerizable compound, a polymer, an inorganic material, and a metal. Compounds other the ultraviolet absorber of the present invention may not be necessarily dissolved.

The content of the ultraviolet absorber in the solution containing the ultraviolet absorber of the present invention varies depending on the intended purpose and usage form and cannot be indiscriminately determined but may be an arbitrary concentration according to the intended purpose. The content is preferably from 0.001 to 30 mass %, more preferably from 0.01 to 10 mass %, based on the entire amount of the solution. The solution may be previously prepared in a high concentration and used by diluting it at the desired time. The diluting solvent may be arbitrarily selected from the above-described solvents.

Examples of the material that is stabilized by the ultraviolet absorber of the present invention include a dye, a pigment, food, beverage, a body care product, a vitamin preparation, a pharmaceutical, ink, oil, fat, wax, a surface coating, cosmetics, a photographic material, a fabric and a dye therefor, a plastic material, rubber, a coating material, a resin composition, and a polymer additive.

In the case of using the ultraviolet absorber of the present invention, the form thereof may be any method. The ultraviolet absorber of the present invention may be used alone or may be used as a composition and is preferably used as a composition. Above all, a resin composition containing the ultraviolet absorber of the present invention is preferred. The resin composition containing the ultraviolet absorber of the present invention will is described below.

[Resin Composition]

The resin composition of the present invention contains the compound represented by formula (1). The resin composition containing the ultraviolet absorber represented by formula (1) contains a resin. The resin composition containing the ultraviolet absorber of the present invention may be also formed by dissolving a resin in an arbitrary solvent.

The ultraviolet absorber of the present invention can be incorporated into the resin composition by various methods. In the case where the ultraviolet absorber of the present invention has compatibility with the resin composition, the ultraviolet absorber of the present invention can be added directly to the resin composition. After dissolving the ultraviolet absorber of the present invention in an auxiliary solvent having compatibility with the resin composition, the resulting solution may be added to the resin composition. Alternatively, the ultraviolet absorber of the present invention may be dispersed in a high-boiling-point organic solvent or a polymer and the resulting dispersion may be added to the resin composition.

(High-Boiling-Point Organic Solvent)

The boiling point of the high-boiling-point organic solvent is preferably 180° C. or more, more preferably 200° C. or more. The melting point of the high-boiling-point organic solvent is preferably 150° C. or less, more preferably 100° C. or less. Examples of the high-boiling-point organic solvent include a phosphoric acid ester, a phosphonic acid ester, a benzoic acid ester, a phthalic acid ester, a fatty acid ester, a carbonic acid ester, an amide, an ether, a halogenated hydrocarbon, an alcohol and paraffin. Among these, a phosphoric acid ester, a phosphonic acid ester, a phthalic acid ester, a benzoic acid ester and a fatty acid ester are preferred.

As for the method to add the ultraviolet absorber of the present invention, the descriptions of JP-A-58-209735, JP-A-63-264748, JP-A-4-191851, JP-A-8-272058 and British Patent 2016017A may be referred to.

(Resin)

The resin for use in the resin composition is described below. The resin may be either a natural polymer or a synthetic polymer. Examples thereof include a polyolefin (e.g., polyethylene, polypropylene, polyisobutylene, poly(1-butene), poly-4-methylpentene, polyvinylcyclohexane, polystyrene, poly(p-methylstyrene), poly($\alpha$-methylstyrene), polyisoprene, polybutadiene, polycyclopentene, polynorbornene), a copolymer of vinyl monomer (for example, an ethylene/propylene copolymer, an ethylene/methylpentene copolymer, an ethylene/heptene copolymer, an ethylene/vinylcyclohexane copolymer, an ethylene/cycloolefin copolymer (such as cycloolefin copolymer (COC: Cyclo-Olefin Copolymer), e.g., ethylene/norbornene copolymer), a propylene/butadiene copolymer, an isobutylene/isoprene copolymer, an ethylene/vinylcyclohexene copolymer, an ethylene/alkyl acrylate copolymer, and an ethylene/alkyl methacrylate copolymer), an acrylic polymer (e.g., polymethacrylate, polyacrylate, polyacrylamide, polyacrylonitrile), polyvinyl chloride, polyvinylidene chloride, polyvinyl fluoride, polyvinylidene fluoride, a vinyl chloride/vinyl acetate copolymer, a polyether (e.g., polyalkylene glycol, polyethylene oxide, polypropylene oxide), a polyacetal (e.g., polyoxyethylene), polyamide, polyimide, polyurethane, polyurea, a polyester (e.g., polyethylene terephthalate, polyethylene naphthalate), polycarbonate, polyketone, polysulfone polyether ketone, a phenol resin, a melamine resin, a cellulose ester (e.g., diacetyl cellulose, triacetyl cellulose (TAC), propionyl cellulose, butyryl cellulose, acetylpropionyl cellulose, nitrocellulose), polysiloxane, and a natural polymer (e.g., cellulose, rubber, gelatin).

The resin for use in the present invention is preferably a synthetic polymer, more preferably polyolefin, acrylic polymer, polyester, polycarbonate, or cellulose ester. Above all, polyethylene, polypropylene, poly(4-methylpentene), polymethyl methacrylate, polycarbonate, polyethylene terephthalate, polyethylene naphthalate, polybutylene terephthalate, and triacetyl cellulose are preferred.

The resin for use in the present invention is preferably a thermoplastic resin.

In the present invention, two or more kinds of compounds represented by formula (1) differing in the structure may be used in combination as the ultraviolet absorber. A compound represented by formula (1) and one or more kinds of ultraviolet absorbers having a different structure may be used in combination. When two kinds (preferably three kinds) of ultraviolet absorbers differing in the fundamental skeleton structure are used in combination, ultraviolet light in a wide wavelength region can be absorbed. Also, when two or more kinds of ultraviolet absorbers are used in combination, this produces an action of stabilizing the dispersion state of the ultraviolet absorber. As the ultraviolet absorber having a structure other than formula (1), any compound may be used, and this ultraviolet absorber includes a compound such as triazine-based, benzotriazole-based, benzophenone-based, merocyanine-based, cyanine-based, dibenzoylmethane-based, cinnamic acid-based, cyanoacrylate-based, and benzoic acid ester-based compounds. Examples thereof include ultraviolet absorbers described in *Fine Chemical*, pp. 28-38 (May, 2004), *Kobunshi Yo Kinousei Tenkazai no Shin-Tenkai (New Development of Functional Additives for Polymers)*, pp. 96-140, Toray Research Center (1999), and Yasukazu Ohkatsu (supervisor), *Kobunshi Tenkazai no Kaihatsu to Kankyo Taisaku (Development of Polymer Additives and Environmental Measures)*, pp. 54-64, CMC (2003).

The ultraviolet absorber having a structure other than formula (1) is preferably a benzotriazole-based compound, a benzophenone-based compound, a salicylic acid-based compound, a benzoxazinone-based compound, a cyanoacrylate-based compound, a benzoxazole-based compound, a merocyanine-based compound, or a triazine-based compound, more preferably a benzoxazinone-based compound, a benzotriazole-based compound, a benzophenone-based compound, or a triazine-based compound, still more preferably a benzoxazinone-based compound. The ultraviolet absorber having a structure other than formula (1) is described in detail in paragraphs [0117] to [0121] of JP-A-2008-273950, and the materials described therein can be applied also in the invention.

As described above, in the present invention, a compound represented by formula (1) and a benzoxazinone-based compound are preferably used in combination. The compound represented by formula (1) has excellent light resistance even in the long wavelength region and therefore, produces an effect of preventing deterioration of benzoxazinone capable of blocking light even in the longer wavelength region and when used in combination with the benzoxazinone-based compound, the blocking effect even in the longer wavelength region can be advantageously maintained for a long time.

In the present invention, a practically sufficient ultraviolet-blocking effect is obtained only by the ultraviolet absorber of the present invention, but in the case of more strictly requiring the effect, a white pigment having a strong opacifying power, such as titanium oxide, may be used in combination. Also, when an appearance or color tone becomes a problem, or if desired, a trace amount (0.05 mass % or less) of a colorant can be used in combination. A fluorescent brightener may be used in combination for applications in which transparency or white color is important. Examples of the fluorescent brightener include commercially available products and the compound of formula (1) as well as Compounds 1 to 35 described in JP-A-2002-53824.

The ultraviolet absorber of the invention may be contained in an arbitrary amount necessary to impart the desired performance. The content varies depending on the compound or resin used but can be appropriately determined. The content in the resin composition is preferably from more than 0 mass % to 20 mass %, more preferably from more than 0 mass % to 10 mass %, still more preferably from 0.05 to 5 mass %. The content in the range above is preferred because a sufficient ultraviolet-blocking effect is obtained and bleed-out can be suppressed.

The resin composition of the present invention may appropriately contain, in addition to the above-described polymer substance and ultraviolet absorber, an arbitrary additive such as antioxidant, light stabilizer, processing stabilizer, anti-aging agent and compatibilizer, if desired.

The resin composition containing the ultraviolet absorber of the invention is applicable to all applications using a synthetic resin but can be suitably used particularly for applications having a possibility of being exposed to light including sunlight or ultraviolet light. Specific examples thereof include a glass alternative and a surface-coating material therefor; a coating material for window glass, lighting glass and light-protecting glass of house, facility, transport equipment and the like; a window film of house, facility, transport equipment and the like; an interior or exterior material and an interior or exterior coating material of house, facility, transport equipment and the like, and a coating film formed by the coating material; an alkyd resin lacquer paint and a coating film formed by the paint; an acryl lacquer paint and a coating film formed by the paint; a member for ultraviolet-emitting light source such as fluorescent lamp and mercury lamp; a member for precision machine and electric or electronic device; a material for shielding electromagnetic wave or the like emitted from various displays; a container or packaging material for food, chemical, medicine and the like; a special package such as bottle, box, blister and cup; a discoloration inhibitor for compact disk coating, agricultural or industrial sheet or film, print, dyed product, dye/pigment and the like; a protective film for polymer support (for example, plastic parts such as mechanical or automotive parts); a print overcoat; an inkjet medium film; a laminate delustering; an optical light film; a safety glass/front glass intermediate layer; an electrochromic/photochromic application; an over lamination film; a solar heat-controlling film; cosmetics such as sun-block cream, shampoo, rinse and hair-dressing product; a clothing fiber product and a fiber, such as sport wear, stocking and cap; a home interior product such as curtain, carpet and wallpaper; a medical device such as plastic lens, spectacle lens, contact lens and artificial eye; an optical product such as optical filter, backlight display film, prism, mirror and photographic material; a mold film; a transfer-type sticker; a graffiti-proof film; a stationery product such as tape and ink; and a signboard, an indicator or the like and a surface-coating material therefor.

The shape of the polymer shape-formed article formed of the resin composition of the present invention may be any shape such as flat film, powder, spherical particle, crushed particle, bulky continuous body, fiber, tube, hollow yarn, granule, plate and porous.

The resin composition of the present invention contains the ultraviolet absorber of the present invention and therefore, has excellent light resistance (ultraviolet light fastness), where the ultraviolet absorber is kept from precipitation or bleed-out in the long-term use. Also, the resin composition of the present invention has excellent long-wavelength ultraviolet absorbing ability and therefore, not only can be used as an ultraviolet-absorbing filter or container but also can protect a compound susceptible to ultraviolet light. For example, when the polymer substance above is shape-formed by an arbitrary method such as extrusion molding or injection molding, a shape-formed article (e.g., container) composed of the resin composition of the present invention can be obtained. Also, when a solution of the polymer substance is coated/dried on a separately produced shape-formed article, a shape-formed article coated with an ultraviolet absorbing film composed of the resin composition of the present invention can be obtained.

In the case of using the resin composition of the present invention as an ultraviolet absorbing filter or an ultraviolet absorbing film, the polymer substance is preferably transparent. Examples of the transparent resin include a cellulose ester (e.g., diacetyl cellulose, triacetyl cellulose (TAC), propionyl cellulose, butyryl cellulose, acetyl propionyl cellulose, nitrocellulose), a polyamide, a polycarbonate, a polyester (e.g., polyethylene terephthalate, polyethylene naphthalate, polybutylene terephthalate, poly-1,4-cyclohexane dimethylene terephthalate, polyethylene-1,2-diphenoxyethane-4,4'-dicarboxylate, polybutylene terephthalate), a polystyrene (e.g., syndiotactic polystyrene), a polyolefin (e.g., polyethylene, polypropylene, polymethylpentene), a polymethyl methacrylate, a syndiotactic polystyrene, a polysulfone, a polyether sulfone, a polyether ketone, a polyether imide, and a polyoxyethylene. Among these, a cellulose ester, a polycarbonate, a polyester, a polyolefin and an acrylic resin are preferred, a polycarbonate and a polyester are more preferred, a polyester is still more preferred, and a polyethylene terephthalate is yet still more preferred. The polymer shape-formed article obtained from the resin composition of the present invention can be also used as a transparent support, and the transmittance of the transparent support is preferably 80% or more, more preferably 86% or more.

In the present invention, the matters described in paragraphs [0192] to [0230] of JP-A-2009-209343 can be applied.

The packaging material containing the ultraviolet absorber of the present invention is described below. The packaging material containing the ultraviolet absorber of the present invention may be a packaging material composed of any kind of a polymer as long as the polymer contains the compound represented by formula (1). Examples thereof include a thermoplastic resin, a polyvinyl alcohol, a polyvinyl chloride, a polyester, a heat-shrinkable polyester, a styrene-based resin, a polyolefin and ROMP. For example, the packaging material may be a resin having a thin film layer formed by deposition of an inorganic material. For example, the packing material may be paper coated with a resin containing the ultraviolet absorber.

The packaging material containing the ultraviolet absorber of the present invention may package any of food, a beverage, medicine, cosmetics, an individual care product and the like. Examples thereof include food packaging, colored liquid packaging, liquid preparation packaging, medicine container packaging, medical sterilization packaging, photographic light-sensitive material packaging, photographic film packaging, ultraviolet curable ink packaging, and shrink label.

The packaging material containing the ultraviolet absorber of the present invention may be a transparent package or a light-blocking package.

The packaging material containing the ultraviolet absorber of the present invention may have not only an ultraviolet-blocking property but also other performances. Examples thereof include those having also a gas barrier property, those containing an oxygen indicator, and those using the ultraviolet absorber and a fluorescent brightener in combination.

The packaging material containing the ultraviolet absorber of the present invention may be produced by any method. Examples of the method include a method of forming an ink layer, a method of melt-extruding and stacking a resin containing the ultraviolet absorber, a method of coating the ultraviolet absorber on a base material film, and a method of dispersing the ultraviolet absorber in an adhesive.

The container containing the ultraviolet absorber of the present invention is described below. The container containing the ultraviolet absorber of the present invention may be a container composed of any kind of a polymer as long as the polymer contains the compound represented by formula (1). Examples thereof include a thermoplastic resin container, a polyester-made container, a polyethylene naphthalate-made container, a polyethylene-made container, a cyclic olefin-based resin composition-made container, a plastic container, and a transparent polyamide container. For example, the container may be a paper container containing the resin or may be a glass container having an ultraviolet absorbing layer.

The container containing the ultraviolet absorber of the present invention may be used to package any of food, a beverage, medicine, cosmetics, a individual care product, a shampoo and the like. Examples thereof include a liquid fuel-storing container, a golf ball container, a food container, a liquor container, a medicine-filling container, a beverage container, an oily food container, an analytical reagent solution container, an instant noodle container, a light-resistant cosmetic material container, a medical product container, a high-purity chemical solution container, a liquid medicine container, an ultraviolet curable ink container, and a W plastic ampoule.

The container containing the ultraviolet absorber of the present invention may have not only an ultraviolet-blocking property but also other performances. Examples thereof include an antimicrobial container, a flexible container, a dispenser container, and a biodegradable container.

The container containing the ultraviolet absorber of the present invention may be produced by any method. Examples thereof include a two-layer stretching blow-molding method, a multilayer co-extrusion blow-molding method, a method of forming an ultraviolet absorbing layer on the external side of a container, a method using a shrinkable film, and a method using a supercritical fluid.

The coating material and the coating film each containing the ultraviolet absorber of the present invention are described below. The coating material containing the ultraviolet absorber of the present invention may be a coating material composed of any component as long as the coating material contains the compound represented by formula (1). Examples thereof include acrylic resin-based, urethane resin-based, aminoalkyd resin-based, epoxy resin-based, silicone resin-based and fluororesin-based coating materials. In such a resin, a base resin, a curing agent, a diluent, a leveling agent, an anti-repelling agent and the like can be arbitrarily blended.

For example, in the case where an acrylic urethane resin or a silicon acrylic resin is selected as the transparent resin component, a polyisocyanate and the like can be used as the curing agent, and a hydrocarbon-based solvent such as toluene and xylene, an ester-based solvent such as isobutyl acetate, butyl acetate and amyl acetate, or an alcohol-based solvent such as isopropyl alcohol and butyl alcohol, can be used as the diluent. The acrylic urethane resin as used herein indicates an acrylic urethane resin obtained by reacting a methacrylic acid ester (typically, methyl/hydroxyethyl methacrylate copolymer with a polyisocyanate. In this case, examples of the polyisocyanate include tolylene diisocyanate, diphenylmethane diisocyanate, polymethylene polyphenylene polyisocyanate, tolidine diisocyanate, naphthalene diisocyanate, hexamethylene diisocyanate, isophorone diisocyanate, xylylene diisocyanate, dicyclohexylmethane diisocyanate, and hexamethylene diisocyanate. Other examples of the transparent resin component include polymethyl methacrylate, polymethyl methacrylate/styrene copolymer, polyvinyl chloride, and polyvinyl acetate. In addition to these components, for example, a leveling agent such as acrylic resin and silicone resin, and an anti-repelling agent such as silicone type and acrylic type may be blended, if desired.

The purpose of using the coating material containing the ultraviolet absorber of the present invention may be any application. Examples thereof include an ultraviolet-blocking paint, an ultraviolet/near infrared-blocking paint, an electromagnetic wave-blocking paint, a clear paint, a metallic paint composition, a cationic electrodeposition paint, an antimicrobial and lead-free cationic electrodeposition paint, a powder paint, an aqueous middle coat paint, an aqueous metallic paint, an aqueous clear paint, a topcoat paint for automobile, architecture or civil work, a curable paint, a coat-forming composition used for a plastic material such as automobile bumper, a paint for metal plates, a cured gradient coating, a paint material for electric wire, a vehicle refinishing paint, an anionic electrodeposition paint, an automotive paint, a paint for coated steel plate, a paint for stainless steel, an insecticidal paint for lamp, an ultraviolet curable paint, an antimicrobial paint, an eyestrain protection paint, an antifogging paint, an ultra-weather-resistant paint, a gradient paint, a photocatalyst paint, a strippable paint, a concrete separation paint, an anti-corrosion paint, a protective paint, a water-repellent protective paint, a paint for preventing sheet glass scattering, an alkali-soluble protective paint, an aqueous temporary protective paint composition, a floor paint, an emulsion paint, a two-component aqueous paint, a one-component paint, a UV-curable paint, an electron beam-curable paint composition, a thermosetting paint composition, an aqueous paint for baking lacquer, a powder paint, a slurry paint, a repair paint, a water dispersion of powder paint, a paint for plastics, and an electron beam-curable paint.

The coating material containing the ultraviolet absorber of the present invention is generally composed of a coating material (containing a transparent resin component as the main component) and the ultraviolet absorber and is preferably a composition containing the ultraviolet absorber in an amount of 0 to 20 mass % based on the resin. In applying the coating material, the thickness is preferably from 2 to 1,000 µm, more preferably from 5 to 200 µm. The coating material may be applied by an arbitrary method, but examples of the method include a spray method, a dipping method, a roller coating method, a flow coater method and a flow coating method. The drying after coating is preferably performed at a temperature of generally from room temperature to 120° C. for approximately from 10 to 90 minutes, though these may vary depending on the components of the coating material.

The coating film containing the ultraviolet absorber of the present invention is a coating film containing the ultraviolet absorber composed of a compound represented by formula (1), and this is a coating film formed using a coating material containing the ultraviolet absorber of the present invention.

The ink containing the ultraviolet absorber of the present invention is described below. The ink containing the ultraviolet absorber of the present invention may be an ink in any form as long as the ink contains the compound represented by formula (1). Examples thereof include a dye ink, a pigment ink, an aqueous ink, and an oil-based ink. Also, the ink may be used for any application. Examples thereof include a screen printing ink, a flexographic printing ink, a gravure printing ink, a lithographic offset printing ink, a letterpress ink, a UV ink, and an EB ink. Other examples include an inkjet ink, a photochromic ink, a thermal transfer ink, a masking ink, a security ink, and a DNA ink.

Also, all embodiments obtained using the ink containing the ultraviolet absorber of the present invention are included in the present invention. Examples thereof include a printed matter, a laminate obtained by laminating the printed matter, a packaging material or container using the laminate, and an ink receiving layer.

The fiber containing the ultraviolet absorber of the present invention is described below. The fiber containing the ultraviolet absorber of the present invention may be a fiber composed of any kind of a polymer as long as the polymer contains the compound represented by formula (1). Examples thereof include a polyester fiber, a polyphenylene sulfide fiber, a polyamide fiber, an aramid fiber, a polyurethane fiber, and a cellulose fiber.

The fiber containing the ultraviolet absorber of the present invention may be produced by any method. For example, a polymer previously containing the compound represented by formula (1) may be processed into a fiber shape, or the fiber obtained by processing may be treated with a solution containing the compound represented by formula (1). The treatment may be also performed using a supercritical fluid.

The fiber containing the ultraviolet absorber of the present invention can be used for various applications. Examples thereof include clothing, backing cloth, underwear, blanket, hosiery, artificial leather, moth-repellent mesh sheet, mesh sheet for construction, carpet, moisture-permeable water-repellent sheet, nonwoven fabric, ultrafine fiber, fiber-made sheet material, refreshing clothing moisture-permeable water-repellent sheet, flame-retardant synthetic suede cloth structure, resin tarpaulin, filming agent, external wall material, agricultural greenhouse, net or mesh for building material, filter backing, stain-proof filming agent, mesh fabric, land net, underwater net, ultrafine fiber, textile fiber, air-bag base cloth, and ultraviolet-absorbing fiber product.

The architectural material containing the ultraviolet absorber of the present invention is described below. The architectural material containing the ultraviolet absorber of the present invention may be an architectural material composed of any kind of a polymer as long as the polymer contains the compound represented by formula (1). Examples thereof include vinyl chloride-based, olefin-based, polyester-based, polyphenylene ether-based and polycarbonate-based materials.

The architectural material containing the ultraviolet absorber of the present invention may be produced by any method, for example, by forming a material containing the compound represented by formula (1) into a desired shape, by stacking a material containing the compound represented by formula (1), by forming a coat layer using the compound represented by formula (1), or by applying a coating material containing the compound represented by formula (1).

The architectural material containing the ultraviolet absorber of the present invention can be used for various applications. Examples thereof include an exterior architectural material, an architectural wood structure, an architectural roofing material, an antimicrobial architectural material, an architectural base material, a stain-proof architectural material, a flame-retardant material, a ceramic architectural material, a decorative architectural material, an architectural painted article, a cosmetic material, an architectural material net, an architectural moisture-permeable water-repellent sheet, an architectural mesh sheet, an architectural film, a decorative film, an architectural coating material, an architectural adhesive composition, a civil engineering construction structure, a walking path coating material, a sheet-like photocurable resin, a wood-protecting paint, a push-switch cover, a bond-sheeting agent, an architectural backing, a wall paper, a decorative polyester film, a decorative polyester film for shape-formed member, and a floor material.

The recording medium containing the ultraviolet absorber of the present invention is described below. The recording medium containing the ultraviolet absorber of the present invention may be any recording medium as long as it contains the compound represented by formula (1). Examples thereof include an inkjet recording medium, a sublimation transfer image-receiving sheet, an image-recording medium, a heat-sensitive recording medium, a reversible heat-sensitive recording medium, and an optical information recording medium.

The image display device containing the ultraviolet absorber of the present invention is described below. The image display device containing the ultraviolet absorber of the present invention may be any image display device as long as it contains the compound represented by formula (1). Examples thereof include an image display device using an electrochromic element, a so-called electronic paper image display device, a plasma display, and an image display device using an organic EL element. The ultraviolet absorber of the present invention may be used, for example, by forming an ultraviolet absorbing layer in a laminate structure or by incorporating the ultraviolet absorber into a necessary member such as circularly polarizing plate.

The solar cell cover containing the ultraviolet absorber of the present invention is described below. The solar cell applied in the present invention may be a solar cell composed of an element in any form, such as crystalline silicon solar cell, amorphous silicon solar cell and dye-sensitized solar cell. In a crystalline silicon solar cell or amorphous silicon solar cell, a cover material is used as a protective member for imparting stain-proofing property, impact resistance and durability. Also, in a dye-sensitized solar cell, a metal oxide-based semiconductor capable of being excited by light (particularly, ultraviolet light) and becoming active is used as the electrode material, and this has a problem that the dye adsorbed as a photosensitizer is deteriorated and the solar power efficiency is gradually reduced. To solve this problem, it has been proposed to provide an ultraviolet-absorbing layer.

The solar cell cover containing the ultraviolet absorber of the present invention may be a cover containing any kind of a polymer. Examples of the polymer include a polyester, a thermosetting transparent resin, an α-olefin polymer, a polypropylene, a polyether sulfone, an acrylic resin, and a transparent fluororesin, which are described in JP-A-2006-310461.

The solar cell cover containing the ultraviolet absorber of the present invention may be produced by any method. For example, an ultraviolet absorbing layer may be formed; layers each containing the ultraviolet absorber may be stacked; the ultraviolet absorber may be contained in a filler layer resin; or a film may be formed from a polymer containing the ultraviolet absorber.

The solar cell cover containing the ultraviolet absorber of the present invention may be in any form. Examples thereof include a film, a sheet, a laminate film, and a cover glass structure. The solar cell cover includes, for example, a front sheet and a back sheet. The solar cell cover may contain the ultraviolet absorber in a sealer.

The glass or glass coat containing the ultraviolet absorber of the present invention is described below. The glass or glass coat containing the ultraviolet absorber of the present invention may be in any form as long as it contains the compound represented by formula (1). Also, the glass or glass coat may be used for any application. Examples thereof include a heat ray-blocking glass, a window glass, a colored glass, an ultraviolet sharp-cut glass for high-intensity light sources such as mercury lamp and metal halide lamp, a frit glass, an ultraviolet-blocking glass for vehicles, a colored heat ray-absorbing glass, a fluorescent brightening agent-containing ultraviolet-absorbing insulated glass, an ultraviolet/heat ray-blocking glass for automobiles, an exterior stained glass, a water-repellent ultraviolet/infrared ray-absorbing glass, a glass for head-up display device of vehicles, a dimming heat barrier multilayer window, an ultraviolet/infrared cut glass, an ultraviolet cut glass, an ultraviolet/infrared-absorbing window glass, an ultraviolet-blocking stain-proof window film, a translucent panel for cultivation house, an ultraviolet/infrared-absorbing low-transmission glass, a low-reflectance low-transmittance glass, an edge light apparatus, a rough surface-forming sheet glass, a laminated display glass, an electrically conductive film-attached glass, an antiglare glass, an ultraviolet/infrared-absorbing middle-transmission glass, a privacy-protection window glass for vehicles, an antifogging glass for vehicles, a glass for paving materials, a water droplet adhesion-preventing and heat ray-blocking glass plate, an ultraviolet/infrared-absorbing bronze glass, a laminated glass, a glass with ID identification function, a PDP optical filter, and a skylight window. The glass containing the ultraviolet absorber of the present invention may be produced by any method.

Other use examples include an illuminating device light source cover, an artificial leather, a sport goggle, a deflection lens, a hardcoat for various plastic products, a hardcoat for lamination to the exterior surface of window, a window film, a high-definition antiglare hardcoat film, an antistatic hardcoat film, a permeable hardcoat film, the anti-forgery paper described in JP-A-2002-113937, a purple blotch-preventing agent for lawn grass, a sealant for resin film sheet bonding, a light guiding element, a rubber coating agent, an agricultural covering material, a color candle, a cloth-rinsing agent composition, a prism sheet, a protective layer transfer sheet, a photocurable resin product, a floor sheet, a light-blocking printed label, a fuel cup, a hardcoat film-coated article, an intermediate transfer recording medium, an artificial hair, a low-temperature heat-shrinkable film for label, a fishing article, a microbead, a pre-coated metal plate, a thin-wall film, a heat-shrinkable film, an in-mold shape-forming label, a projection screen, a decorative sheet, a hot-melt adhesive, an adhesive, an electrodeposited coat, a basecoat, a wood surface protection, a dimming material, a dimming film, a dimming glass, a moth-repellent lamp, a touch panel, a sealant for resin film sheet bonding, a polycarbonate film coating, an optical fiber tape, and a solid wax.

The method for evaluating the light resistance of the polymer material is described below. The method for evaluating the light resistance of the polymer material can be referred to, for example, *Kobunshi no Hikari Anteika Gijutsu* (*Technique for Photostabilizing Polymers*), pp. 85-107, CMC Publishing (2000), *Koseino Toryo no Kiso to Bussei* (*Basis and Physical Properties of High Functional Coating Materials*), pp. 314-359, CMC Publishing (2003), *Kobunshi Zairyo to Fukugouzai Seihin no Taikyusei* (*Durability of Polymer Materials and Composite Material Products*), CMC Publishing (2005), *Kobunshi Zairyo no Chojumyo-ka to Kankyo Taisaku* (*Elongation of Lifetime of Polymer Materials and Environmental Measures*), CMC Publishing (2000), H. Zweifel (compiler), *Plastics Additives Handbook 5th Edition*, pp. 238-244, Hanser Publishers, and Tadahiko Kutsura, *Kiso Koza 2, Plastic Housou Yoki no Kagaku* (*Basic Seminar 2, Science of*

*Plastic Packaging Container*), Chapter 8, Society of Packaging Science & Technology, Japan (2003).

Also, the evaluations in each application can be achieved by the following known evaluation methods. The degradation of the polymer material due to light can be evaluated by the methods of JIS-K7105: 1981, JIS-K7101: 1981, JIS-K7102: 1981, JIS-K7219: 1998, JIS-K7350-1: 1995, JIS-K7350-2: 1995, JIS-K7350-3 :1996 and JIS-K7350-4: 1996, or a method based thereon.

The light resistance in use for packaging/container can be determined by the method of JIS-K7105 or a method based thereon. Specific examples of the method include an evaluation of light transmittance or transparency of a bottle body, a sensory test evaluation of the bottle content after exposure to ultraviolet light from a xenon light source, a haze value evaluation after xenon lamp irradiation, a haze value evaluation using a halogen lamp as the light source, a yellowness index evaluation by a blue wool scale after exposure to a mercury lamp, a haze value evaluation using a sunshine weather meter, a visual evaluation of colorability, an ultraviolet transmittance evaluation, an ultraviolet blocking rate evaluation, a light transmittance evaluation, evaluations of viscosity and light transmittance of ink in an ink container, an evaluation with an eye or based on the color difference $\Delta E$ of the sample in a container after exposure to sunlight, evaluations of ultraviolet transmittance, light transmittance, color difference, light transmittance, haze value, color tone, yellowness index and light-blocking property after white fluorescent lamp irradiation, a whiteness evaluation using the color difference formula of the $L^*a^*b^*$ color system, a yellowing evaluation based on the color difference $\Delta Ea^*b^*$ of the exposed sample for each wavelength after dispersion of xenon light, an ultraviolet absorbance evaluation after exposure to ultraviolet light, a tensile elongation evaluation of the film after exposure using a sunshine weather meter, an antimicrobial evaluation after exposure using a xenon weather meter, a discoloration evaluation of the package content after fluorescent lamp irradiation, evaluations of peroxide and color tone of oil after exposing a salad oil-filled bottle to a fluorescent lamp, an absorbance difference evaluation after chemical lamp irradiation, evaluations of surface gloss retention and appearance after exposure using a sunshine weather meter, evaluations of color difference and flexural strength after exposure using a sunshine weatherometer, a light blocking ratio evaluation, and an evaluation of peroxide production in kerosene.

The long-term durability in use for coating material/coating film can be evaluated by the methods of JIS-K5400, JIS-K5600-7-5:1999, JIS-K5600-7-6:2002, JIS-K5600-7-7: 1999, JIS-K5600-7-8:1999 and JIS-K8741, or a method based thereon. Specific examples thereof include an evaluation based on the color density, the color difference $\Delta Ea^*b^*$ in the CIE $L^*a^*b^*$ color coordinates or the residual gloss after exposure using a xenon light resistance tester and an UVCON apparatus, an absorbance evaluation after exposure of a film on a quartz slide by using a xenon arc light resistance tester, an evaluation based on the color density or the color difference $\Delta Ea^*b^*$ in the CIE $L^*a^*b^*$ color coordinates after exposing the wax to a fluorescent lamp or an UV lamp, a color hue evaluation after exposure using a Metalweather weather resistance tester, an evaluation of gloss retention or an evaluation based on the color difference $\Delta Ea^*b^*$ after an exposure test using a metal halide lamp, an evaluation of glossiness after exposure using a sunshine carbon arc light source, an evaluation based on the color difference $\Delta Ea^*b^*$ or an evaluation of the gloss retention or appearance after exposure using a Metalweather weather resistance tester, an evaluation of gloss retention after exposure using a sunshine weatherometer, an evaluation based on the color difference $\Delta Ea^*b^*$ or an evaluation of gloss retention after exposure using a QUV weather resistance tester, an evaluation of gloss retention after exposure using a sunshine weatherometer, an appearance evaluation of the coated plate after exposure using a sunshine weatherometer, an evaluation of gloss retention or change in brightness after exposure using a sunshine weatherometer, an appearance evaluation of the coating film in a deteriorated state after exposure of the coating film to dew cycle WOM, an evaluation of ultraviolet transmittance of the coating film, an evaluation of ultraviolet blocking rate of the coating film, a comparative evaluation of the time until the gloss retention rate of the coating film is reduced to 80% by using a sunshine weatherometer, an evaluation of rusting after exposure using a Dewpanel light control weather meter, an evaluation of strength of the concrete against the coated formwork after outdoor exposure, an evaluation based on the color difference $\Delta Ea^*b^*$ after outdoor exposure, a grid adhesion evaluation, a surface appearance evaluation, a gloss retention evaluation after outdoor exposure, and an evaluation of yellowing degree ($\Delta YI$) after exposure using a carbon arc light source.

The light resistance in use for ink can be evaluated by the methods of JIS-K5701-1:2000, JIS-K7360-2 and ISO105-B02, or a method based thereon. Specific examples thereof include an evaluation based on the color density or the measurement of the CIE $L^*a^*b^*$ color coordinates after exposure using an office fluorescent lamp or a discoloration tester, an electrophoretic evaluation after exposure to ultraviolet light from a xenon arc light source, a density evaluation of the printed matter by using a xenon fade meter, a deinking evaluation using a 100 W chemical lamp, an evaluation of dye residual ratio in the image formed region by using a weather meter, evaluations of chalking and discoloration of the printed matter by using an Eye Super UV tester, an evaluation based on the color difference $\Delta Ea^*b^*$ of the CIE $L^*a^*b^*$ color coordinates for a printed matter after exposure using a xenon fade meter, and a reflectance evaluation after exposure using a carbon arc light source.

The light resistance of the solar cell module can be evaluated by the methods of JIS-C8917:1998 and JIS-C8938:1995, or a method based thereon. Specific examples thereof include an I-V measurement photovoltaic efficiency evaluation after exposure using a xenon lamp light source equipped with a sunlight-simulating compensation filter, an evaluation of discoloration gray scale degree after exposure using a sunshine weather meter or a fade mater, and an evaluation of color, appearance and adherence.

The light resistance of the fiber and fiber product can be evaluated by the methods of JIS-L1096:1999, JIS-A5905: 2003, JIS-L0842, JIS-K6730, JIS-K7107, DIN75.202, SAEJ1885, SN-ISO-105-B02 and AS/NZS4399, or a method based thereon. Examples thereof include an ultraviolet transmittance evaluation, a blue scale discoloration evaluation after exposure using a xenon light source or a carbon arc light source, a UV protection evaluation, an ultraviolet-blocking effect evaluation, a blue scale discoloration evaluation after dry cleaning and exposure using a carbon arc light source, an evaluation of the color difference $\Delta E^*$ based on lightness index and chromaticness index after exposure using a fadeometer, a tensile strength evaluation after exposure using a UV tester or a sunshine weather meter, a total transmission evaluation, a strength retention evaluation, an ultraviolet protection factor (UPF) evaluation, a discoloration gray scale evaluation after exposure using a high-temperature fade meter, an appearance evaluation after outdoor exposure, evaluations of yellowness index (YI) and yellowing degree (ΔYI) after exposure to ultraviolet light, and a conventional reflectance evaluation.

The light resistance of the architectural material can be evaluated by the method of JIS-A1415:1999 or a method based thereon. Specific examples thereof include a surface color tone evaluation after exposure using a sunshine weatherometer, an appearance evaluation after exposure using a carbon arc light source, an appearance evaluation after exposure using an Eye Super UV tester, an absorbance evaluation after exposure, an evaluation of chromaticity and color difference after exposure, an evaluation based on the color difference ΔEa*b* of the CIE L*a*b* color coordinates after exposure using a metal halide lamp light source, a gloss retention evaluation, the evaluation of change in the haze value after exposure using a sunshine weather meter described in JP-A-10-44352 and JP-A-2003-211538, an elongation retention evaluation using a tensile tester after exposure, an ultraviolet transmittance evaluation after dipping in a solvent, a visual appearance evaluation after exposure using an Eye Super UV tester, an evaluation of change in the glossiness after a QUV test, a gloss retention evaluation after exposure using a sunshine weatherometer, an evaluation based on the color difference ΔEa*b* after exposure to ultraviolet light using a black light blue fluorescent lamp, an adherence retention evaluation after exposure using a UVCON acceleration tester, an ultraviolet-blocking effect evaluation, an appearance evaluation after outdoor exposure (JIS-A1410), a total light transmittance evaluation, a haze change evaluation, a tensile shear adhesive strength evaluation, a total light transmittance evaluation after exposure using a xenon weather meter, a haze evaluation, a yellowness index evaluation, and evaluations of yellowing degree (ΔYI) and ultraviolet absorber residual ratio after exposure using a sunshine weatherometer.

The light resistance in use for recording medium can be evaluated by the method of JIS-K7350 or a method based thereon. Specific examples thereof include an evaluation of change in the base color difference in the printing region after fluorescent lamp irradiation, an image density residual ratio evaluation after exposure using a xenon weather meter, an evaluation of change in the optical reflection density due to exposure using a xenon weather meter, a yellowing degree evaluation based on the L*a*b* evaluation system after exposure using a Suntest CPS photofading tester, a discoloration evaluation after exposure using a fade meter, a visual discoloration evaluation after exposure using a xenon fade meter, a color density retention evaluation after exposure to indoor sunlight, a color density retention evaluation after exposure using a xenon weather meter, a C/N evaluation after exposure using a fade meter, a fog density evaluation after exposure to a fluorescent lamp, an optical reflection density evaluation after exposure using a fluorescent lamp, an erasure evaluation, a color difference ΔE* evaluation after exposure using an Atlas fade meter, a visual evaluation of discoloration after exposure using a carbon arc fade meter, an evaluation of color conversion retention of an organic EL device, and a measurement/evaluation of organic EL display luminance after exposure by a xenon discoloration tester.

As for other evaluation methods, the evaluation can be performed by the methods of JIS-K7103 and ISO/DIS9050, or a method based thereon. Specific examples thereof include an appearance evaluation of a polycarbonate coat film after exposure by a UV tester, a blue scale evaluation of artificial hair after exposure to ultraviolet light, an evaluation of water contact angle on a processed cloth for evaluation after exposure using an accelerated weather resistance tester, the visual evaluation of the image projected on a projection screen after exposure using a weather resistance tester described in JP-A-2005-55615, a visual evaluation of the sample surface deterioration and change in the design property after exposure using a sunshine weather meter or a metal weather meter, a visual appearance evaluation after exposure to lighting using a metal lamp reflector, a light transmittance evaluation of bottle label, a polypropylene deterioration evaluation after exposure using a xenon weather meter under humid condition, a deterioration evaluation of hardcoat film by using a sunshine weatherometer, evaluations of deterioration, hydrophilicity and scratch resistance of base material, a gray scale evaluation of color difference of artificial leather after exposure using a xenon lamp light source, an evaluation of liquid crystal device characteristics after exposure using a mercury lamp, an adherence evaluation after exposure using a sunshine weatherometer, a purple blotch degree evaluation of lawn grass, an ultraviolet transmittance evaluation after exposure using a xenon arc light source, a tensile strength evaluation, a concrete adhesion velocity evaluation, evaluations of appearance and coating film adherence after exposure using a sunshine weatherometer, an evaluation of yellowing degree and adherence after exposure using a carbon arc light source, an adhesive performance evaluation using an ultraviolet fade meter, an evaluation of flying prevention of insects during lighting, an evaluation of yellowing degree (ΔYI) of the laminated glass by using an Eye Super UV tester, evaluations of surface appearance and gloss retention after QUV irradiation and humidity-resistance test, an evaluation of color difference with aging using a Dewpanel light control weather meter, evaluations of glossiness (DI) and yellowness index (YI) of the wood base material in a coated state after exposure using a xenon weatherometer, an ultraviolet absorbance evaluation after repeating ultraviolet irradiation and darkness, and an evaluation of dye discoloration based on color difference ΔE after exposure to ultraviolet light.

EXAMPLES

The present invention is described in greater detail below by referring to Examples, but the present invention is not limited thereto.

Example p1

Preparation of Exemplified Compound (1)

Acetonitrile (600 mL) and 356.2 g of DBU (diazabicycloundecene (1,8-diazabicyclo[5,4.0]undec-7-ene)) were added to 160.0 g of salicylamide and dissolved. To this solution, 231.7 g of methyl 4-(chloroformyl)benzoate was added, and the mixture was stirred at room temperature for 24 hours. To the resulting reaction solution, 1,800 mL of water and 170 mL of 35% hydrochloric acid were added, and the obtained solid was filtered and washed with water to obtain 343.0 g of Synthetic Intermediate pA (yield: 98%).

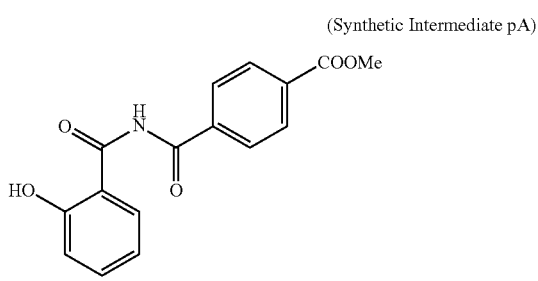 [SMILES: COC(=O)c1ccc(C(=O)NC(=O)c2ccccc2O)cc1]

(Synthetic Intermediate pA)

Acetonitrile (1,200 mL) and 98.1 g of sulfuric acid were added to 200.0 g of Synthetic Intermediate pA, and the mixture was stirred at 90° C. for 4 hours. To the resulting reaction solution, 600 mL of triethylamine was added, and the mixture was cooled to room temperature. The obtained solid was filtered and washed with water to obtain 182.3 g of Synthetic Intermediate pB (yield: 97%).

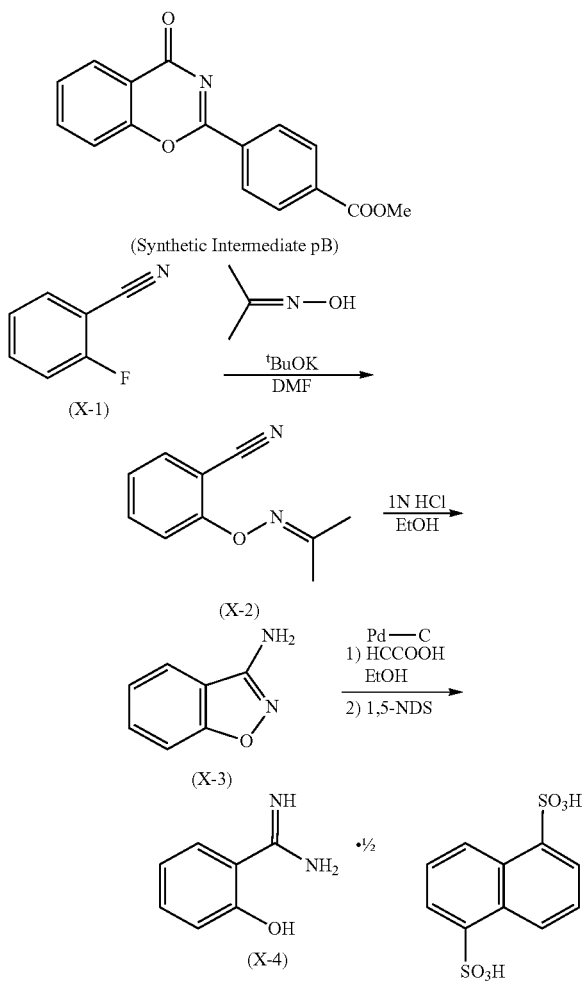

(Synthesis of X-2)

A three-neck flask was charged with 39.5 g (1.1 molar equivalents) of acetoxime, 600 mL of DMF (N,N-dimethylformamide) and 60.6 g (1.1 molar equivalents) of potassium tert-butoxide, and the mixture was stirred at room temperature for 30 minutes. The inner temperature was then set to 0° C. and thereto, 60 g (1.0 molar equivalent) of Compound (X-1) was slowly added dropwise. After the dropwise addition, the inner temperature was raised to 25° C., and the mixture was stirred at this temperature for 1 hour.

The resulting reaction mixture was subjected to an extraction and separation operation with an aqueous ammonium chloride solution and ethyl acetate, and the obtained organic phase was washed by adding saturated brine and then separated. The thus-obtained organic phase was concentrated in a rotary evaporator to yield a residue as a crude product of Compound (X-2).

(Synthesis of X-3)

A three-neck flack was charged with the entire amount of the crude product of Compound (X-2) obtained above and after adding 700 mL of ethanol and 500 mL of aqueous 1 mol/L hydrochloric acid, the reaction mixture was heated to an inner temperature of 80° C. and stirred at this temperature for 3 hours.

The reaction mixture was cooled to an inner temperature of 25° C. and then subjected to an extraction and separation operation with an aqueous saturated sodium hydrogencarbonate solution and ethyl acetate, and the obtained organic phase was washed by adding saturated brine and separated. The thus-obtained organic phase was concentrated in a rotary evaporator to yield a residue as a crude product of Compound (X-3).

(Synthesis of X-4)

In a three-neck flask, after filling the inside of flask with nitrogen gas, 6.5 g of 10% Pd-C (produced by Wako Pure Chemical Industries, Ltd.) was added, and 2,000 mL of ethanol and the entire amount of the crude product of Compound (X-3) obtained above were further added. The resulting mixture was heated/refluxed, and 55 mL (3 molar equivalents) of formic acid was slowly added dropwise thereto, followed by stirring at this temperature for 5 hours. The resulting reaction mixture was cooled to an inner temperature of 25° C. and then subjected to Celite filtration and to the mother solution separated by filtration, 105 g of 1,5-naphthalenedisulfonic acid was added. After raising the inner temperature to 70° C., the mixture was stirred for 30 minutes and then gradually cooled to room temperature, and the crystal was separated by filtration to obtain 100 g of Compound (X-4). The yield was 72% based on Compound (X-1) as the starting material. The obtained crystal was pale brown.

$^1$H NMR (deuterated DMSO): δ6.95-6.98 (1H), δ7.02-7.04 (1H), δ7.40-7.51 (3H), δ7.90-7.95 (1H), δ8.75 (1H), δ8.85-8.88 (2H), δ9.03 (2H), δ10.89 (1H).

Methanol (50 mL) and 3.8 g of a 28% sodium methoxide methanol solution were added to 5.5 g of Compound (X-4). To this solution, 5.0 g of Synthetic Intermediate pB was added, and the mixture was stirred at 60° C. for 3 hours. The resulting reaction solution was cooled to room temperature, and 0.2 mL of hydrochloric acid was added thereto. The obtained solid was filtered and washed with water and methanol to obtain 6.8 g of Exemplified Compound (1) (yield: 95%). MS: m/z 400 (M+).

$^1$H NMR (CDCl$_3$): δ7.04-7.12 (4H), δ7.53-7.57 (2H), δ8.24-8.27 (2H), δ8.51-8.53 (4H), δ12.91 (2H). λmax=353 nm (EtOAc).

Synthesis Example p2

Preparation of Exemplified Compound (2)

Acetonitrile (600 mL) and 355.2 g of DBU were added to 160.0 g of salicylamide and dissolved. To this solution, 193.2 g of 4-cyanobenzoyl chloride was added, and the mixture was stirred at room temperature for 24 hours. To the resulting reaction solution, 1,200 mL of water and 150 mL of hydrochloric acid were added, and the obtained solid was filtered and washed with water to obtain 292.8 g of Synthetic Intermediate pC (yield: 94%).

(Synthetic Intermediate pC)

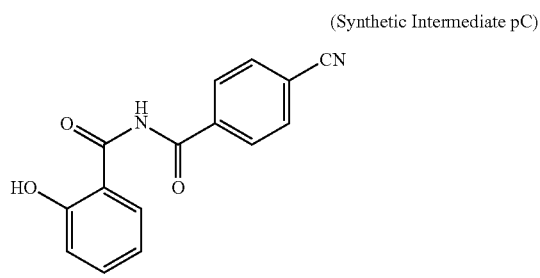 [SMILES: N#Cc1ccc(C(=O)NC(=O)c2ccccc2O)cc1]

Acetonitrile (1,200 mL) and 110.5 g of sulfuric acid were added to 200.0 g of Synthetic Intermediate pC, and the mixture was stirred at 90° C. for 4 hours. To the resulting reaction solution, 600 mL of triethylamine was added, and the mixture was cooled to room temperature. The obtained solid was filtered and washed with water to obtain 177.2 g of Synthetic Intermediate pD (yield: 95%).

(Synthetic Intermediate pD)

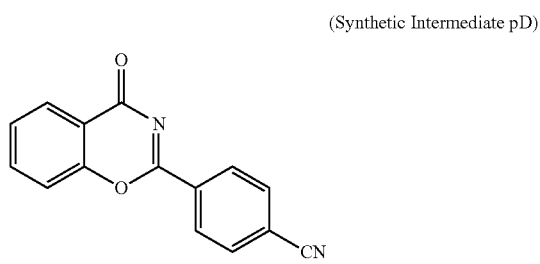 [SMILES: N#Cc1ccc(-c2nc(=O)c3ccccc3o2)cc1]

Methanol (50 mL) and 4.3 g of a 28% sodium methoxide methanol solution were added to 6.2 g of Compound (X-4). To this solution, 5.0 g of Synthetic Intermediate pD was added, and the mixture was stirred at 60° C. for 3 hours. The resulting reaction solution was cooled to room temperature, and 0.2 mL of hydrochloric acid was added thereto. The obtained solid was filtered and washed with water and methanol to obtain 7.1 g of Exemplified Compound (2) (yield: 96%). MS: m/z 367 (M+).

$^1$H NMR (CDCl$_3$): δ7.01-7.13 (4H), δ7.56-7.59 (2H), δ7.91-7.93 (2H), δ8.52-8.54 (2H), δ8.58-8.60 (2H), δ12.77 (2H). λmax=355 nm (EtOAc).

Synthesis Example p3

Preparation of Exemplified Compound (104)

Acetonitrile (80 mL) and 36.4 g of DBU were added to 20.0 g of 4-methoxysalicylamide and dissolved. To this solution, 23.8 g of methyl 4-(chloroformyl)benzoate was added, and the mixture was stirred at room temperature for 24 hours. To the resulting reaction solution, 100 mL of water and 20 mL of hydrochloric acid were added, and the obtained solid was filtered and washed with water to obtain 36.0 g of Synthetic Intermediate pG (yield: 91%).

(Synthetic Intermediate pG)

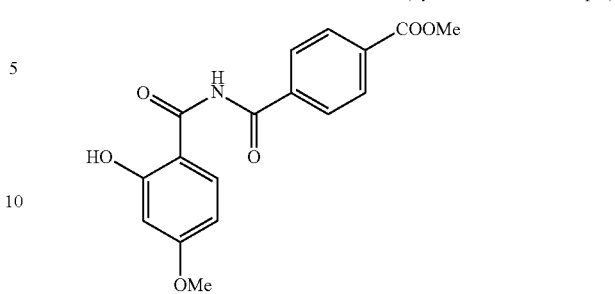

Acetonitrile (200 mL) and 8.9 g of sulfuric acid were added to 20.0 g of Synthetic Intermediate pG, and the mixture was stirred at 90° C. for 4 hours. To the resulting reaction solution, 80 mL of triethylamine was added, and the mixture was cooled to room temperature. The obtained solid was filtered and washed with water to obtain 17.1 g of Synthetic Intermediate pH (yield: 90%).

(Synthetic Intermediate pH)

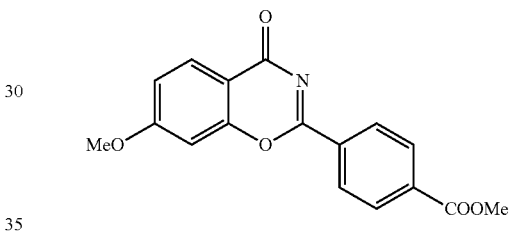

Methanol (50 mL) and 3.4 g of a 28% sodium methoxide methanol solution were added to 5.5 g of Compound (X-4). To this solution, 5.0 g of Synthetic Intermediate pH was added, and the mixture was stirred at 60° C. for 3 hours. The resulting reaction solution was cooled to room temperature, and 0.2 mL of hydrochloric acid was added thereto. The obtained solid was filtered and washed with water and methanol to obtain 6.3 g of Exemplified Compound (104) (yield: 91%). MS: m/z 430 (M+).

$^1$H NMR (CDCl$_3$): δ6.54-6.55 (1H), δ6.63-6.64 (1H), δ7.02-7.10 (2H), δ7.51-7.55 (1H), δ8.23-8.25 (2H), δ8.48-8.50 (3H), δ13.02 (1H), δ13.17 (1H). λmax=352 nm (EtOAc).

Synthesis Example p4

Preparation of Exemplified Compound (3)

Acetonitrile (800 mL) and 444.0 g of DBU were added to 200.0 g of salicylamide and dissolved. To this solution, 303.9 g of 4-(trifluoromethyl)benzoyl chloride was added, and the mixture was stirred at room temperature for 24 hours. To the resulting reaction solution, 2,000 mL of water and 200 mL of hydrochloric acid were added, and the obtained solid was filtered and washed with water to obtain 428.3 g of Synthetic Intermediate pI (yield: 95%).

(Synthetic Intermediate pI)

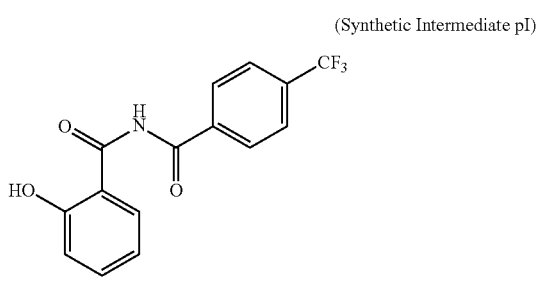 [SMILES: O=C(NC(=O)c1ccccc1O)c1ccc(C(F)(F)F)cc1]

Acetonitrile (240 mL) and 20.2 g of sulfuric acid were added to 34.0 g of Synthetic Intermediate pI, and the mixture was stirred at 90° C. for 4 hours. To the resulting reaction solution, 150 mL of triethylamine was added, and the mixture was cooled to room temperature. The obtained solid was filtered and washed with water to obtain 34.8 g of Synthetic Intermediate pJ (yield: 94%).

(Synthetic Intermediate pJ)

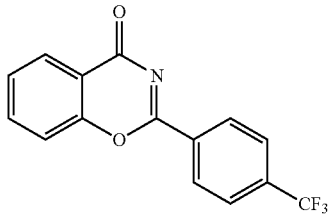

Methanol (50 mL) and 4.6 g of a 28% sodium methoxide methanol solution were added to 6.8 g of Compound (X-4). To this solution, 5.0 g of Synthetic Intermediate pJ was added, and the mixture was stirred at 60° C. for 3 hours. The resulting reaction solution was cooled to room temperature, and 0.2 mL of hydrochloric acid was added thereto. The obtained solid was filtered and washed with water and methanol to obtain 6.7 g of Exemplified Compound (3) (yield: 95%). MS: m/z 409 (M+). $^1$H NMR (CDCl$_3$): δ7.04-7.12 (4H), δ7.53-7.58 (2H), δ7.85-7.89 (2H), δ8.53-8.58 (4H), δ12.84 (2H). λmax=355 nm (EtOAc).

Synthesis Example p5

Preparation of Exemplified Compound (21)

2-Ethylhexanol (31.6 g), 0.13 g of NaOMe and 100 mL of xylene were added to 10 g of Exemplified Compound (1), and the mixture was stirred at 90° C. for 6 hours under reduced pressure. To the resulting reaction solution, water and ethyl acetate were added, followed by stirring. The organic phase separated was concentrated, and the obtained residue was crystallized from hexane/isopropyl alcohol (1:10 by volume) to obtain 11.7 g of Compound (21) (yield: 95%).
MS: m/z 498 (M+).

Synthesis Example p6

Preparation of Exemplified Compound (24)

FINEOXOCOL 180N (produced by Nissan Chemicals Industries, Ltd.) (9.8 g), 0.13 g of NaOMe and 100 mL of xylene were added to 10 g of Exemplified Compound (1), and the mixture was stirred at 90° C. for 6 hours under reduced pressure. To the resulting reaction solution, water and ethyl acetate were added, followed by stirring. The organic phase separated was concentrated, and the obtained residue was crystallized from hexane/isopropyl alcohol (1:10 by volume) to obtain 14.5 g of Exemplified Compound (24) (yield: 92%). MS: m/z 638 (M+). $^1$H NMR (CDCl$_3$): δ0.75-1.90 (35H), δ4.30-4.32 (2H), δ7.05-7.12 (4H), δ7.52-7.58 (2H), δ8.25-8.27 (2H), δ8.53-8.56 (4H), δ12.92 (2H). λmax=354 nm (EtOAc).

Synthesis Example p7

Preparation of Exemplified Compound (72)

Acetonitrile (80 mL) and 29.7 g of DBU were added to 20.0 g of 2-hydroxy-4-(trifluoromethyl)benzamide and dissolved. To this solution, 19.4 g of methyl 4-(chloroformyl)benzoate was added, and the mixture was stirred at room temperature for 24 hours. To the resulting reaction solution, 100 mL of water and 20 mL of 35% hydrochloric acid were added, and the obtained solid was filtered and washed with water to obtain 34.1 g of Synthetic Intermediate pO (yield: 95%).

(Synthetic Intermediate pO)

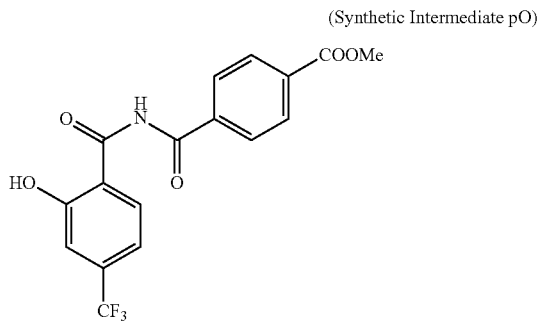 [SMILES: COC(=O)c1ccc(C(=O)NC(=O)c2ccc(C(F)(F)F)cc2O)cc1]

Acetonitrile (200 mL) and 6.9 g of sulfuric acid were added to 20.0 g of Synthetic Intermediate pO, and the mixture was stirred at 90° C. for 4 hours. To the resulting reaction solution, 80 mL of triethylamine was added, and the mixture was cooled to room temperature. The obtained solid was filtered and washed with water to obtain 18.4 g of Synthetic Intermediate pP (yield: 97%).

(Synthetic Intermediate pP)

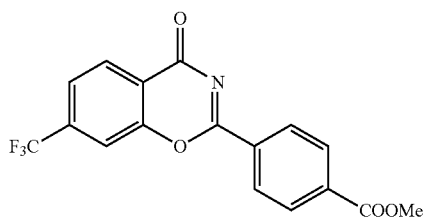

Methanol (100 mL) and 3.4 g of a 28% sodium methoxide methanol solution were added to 5.5 g of Compound (X-4). To this solution, 5.0 g of Synthetic Intermediate pP was added, and the mixture was stirred at 60° C. for 3 hours. The resulting reaction solution was cooled to room temperature, and 0.2 mL of 35% hydrochloric acid was added thereto. The obtained solid was filtered and washed with water and methanol to obtain 5.9 g of Exemplified Compound (72) (yield: 91%).
MS: m/z 467 (M+).

Synthesis Example p8

Preparation of Exemplified Compound (81)

Acetonitrile (80 mL) and 36.4 g of DBU were added to 20.0 g of 2-hydroxy-5-methoxybenzamide and dissolved. To this solution, 23.8 g of methyl 4-(chloroformyl)benzoate was added, and the mixture was stirred at room temperature for 24 hours. To the resulting reaction solution, 100 mL of water and 20 mL of 35% hydrochloric acid were added, and the obtained solid was filtered and washed with water to obtain 38.0 g of Synthetic Intermediate pQ (yield: 96%).

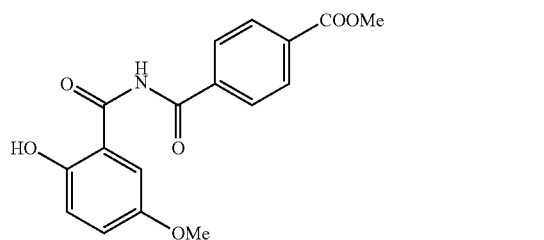

(Synthetic Intermediate pQ)

Acetonitrile (200 mL) and 8.9 g of sulfuric acid were added to 20.0 g of Synthetic Intermediate pQ, and the mixture was stirred at 90° C. for 4 hours. To the resulting reaction solution, 80 mL of triethylamine was added, and the mixture was cooled to room temperature. The obtained solid was filtered and washed with water to obtain 18.1 g of Synthetic Intermediate pR (yield: 96%).

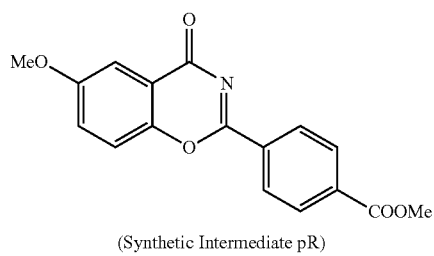 [SMILES: COC(=O)c1ccc(-c2nc(=O)c3cc(OC)ccc3o2)cc1]

(Synthetic Intermediate pR)

Methanol (50 mL) and 3.4 g of a 28% sodium methoxide methanol solution were added to 5.5 g of Compound (X-4). To this solution, 5.0 g of Synthetic Intermediate pR was added, and the mixture was stirred at 60° C. for 3 hours. The resulting reaction solution was cooled to room temperature, and 0.2 mL of hydrochloric acid was added thereto. The obtained solid was filtered and washed with water and methanol to obtain 6.3 g of Exemplified Compound (81) (yield: 91%). MS: m/z 430 (M+).

Synthesis Example p9

Preparation of Exemplified Compound (84)

Acetonitrile (80 mL) and 35.4 g of DBU were added to 20.0 g of 2-hydroxy-5-chlorobenzamide and dissolved. To this solution, 23.1 g of methyl 4-(chloroformyl)benzoate was added, and the mixture was stirred at room temperature for 24 hours. To the resulting reaction solution, 100 mL of water and 20 mL of 35% hydrochloric acid were added, and the obtained solid was filtered and washed with water to obtain 38.1 g of Synthetic Intermediate pS (yield: 98%).

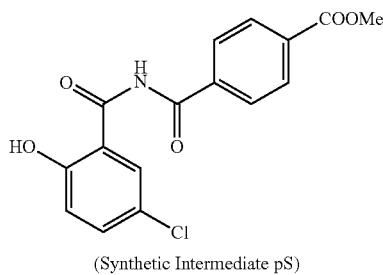 [SMILES: COC(=O)c1ccc(C(=O)NC(=O)c2cc(Cl)ccc2O)cc1]

(Synthetic Intermediate pS)

Acetonitrile (200 mL) and 9.0 g of sulfuric acid were added to 20.0 g of Synthetic Intermediate pS, and the mixture was stirred at 90° C. for 4 hours. To the resulting reaction solution, 80 mL of triethylamine was added, and the mixture was cooled to room temperature. The obtained solid was filtered and washed with water to obtain 18.3 g of Synthetic Intermediate pT (yield: 97%).

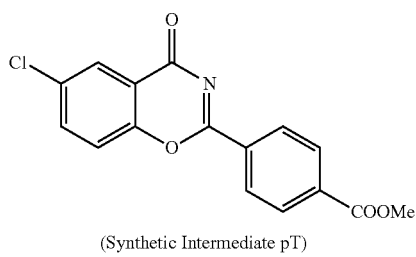 [SMILES: COC(=O)c1ccc(-c2nc(=O)c3cc(Cl)ccc3o2)cc1]

(Synthetic Intermediate pT)

Methanol (100 mL) and 3.3 g of a 28% sodium methoxide methanol solution were added to 5.5 g of Compound (X-4). To this solution, 5.0 g of Synthetic Intermediate pT was added, and the mixture was stirred at 60° C. for 3 hours. The resulting reaction solution was cooled to room temperature, and 0.2 mL of 35% hydrochloric acid was added thereto. The obtained solid was filtered and washed with water and methanol to obtain 6.1 g of Exemplified Compound (84) (yield: 92%). MS: m/z 434 (M+).

Synthesis Example p10

Preparation of Exemplified Compound (98)

Acetonitrile (80 mL) and 32.4 g of DBU were added to 20.0 g of 3-hydroxy-2-naphthamide and dissolved. To this solution, 21.2 g of methyl 4-(chloroformyl)benzoate was added, and the mixture was stirred at room temperature for 24 hours. To the resulting reaction solution, 100 mL of water and 20 mL of 35% hydrochloric acid were added, and the obtained solid was filtered and washed with water to obtain 35.1 g of Synthetic Intermediate pU (yield: 94%).

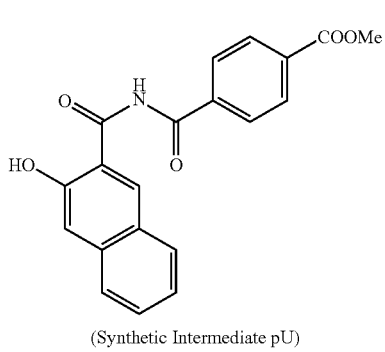 [SMILES: COC(=O)c1ccc(C(=O)NC(=O)c2cc3ccccc3cc2O)cc1]

(Synthetic Intermediate pU)

Acetonitrile (200 mL) and 9.1 g of sulfuric acid were added to 20.0 g of Synthetic Intermediate pU, and the mixture was stirred at 90° C. for 4 hours. To the resulting reaction solution, 80 mL of triethylamine was added, and the mixture was cooled to room temperature. The obtained solid was filtered and washed with water to obtain 17.9 g of Synthetic Intermediate pV (yield: 94%).

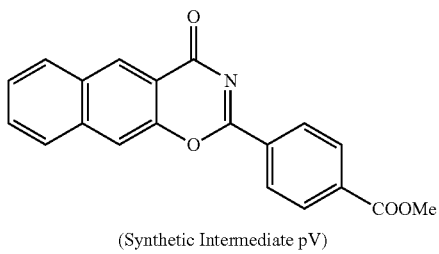 [SMILES: COC(=O)c1ccc(-c2nc(=O)c3cc4ccccc4cc3o2)cc1]

(Synthetic Intermediate pV)

Methanol (100 mL) and 3.0 g of a 28% sodium methoxide methanol solution were added to 5.5 g of Compound (X-4). To this solution, 5.0 g of Synthetic Intermediate pV was added, and the mixture was stirred at 60° C. for 3 hours. The resulting reaction solution was cooled to room temperature, and 0.2 mL of 35% hydrochloric acid was added thereto. The obtained solid was filtered and washed with water and methanol to obtain 6.1 g of Exemplified Compound (98) (yield: 94%). MS: m/z 449 (M+).

Synthesis Example p11

Preparation of Exemplified Compound (9)

Water (20 mL) was added to 2.0 g of Exemplified Compound (1) and thereto, 300 mL of an ethanol solution having dissolved therein 10.0 g of potassium hydroxide at room temperature was added dropwise at room temperature. The mixture was stirred at room temperature for 8 hours, and 35% hydrochloric acid was added until the pH became 2. The obtained solid was filtered and washed with water and methanol to obtain 1.9 g of Exemplified Compound (9) (yield: 97%). $^1$H NMR (deuterated DMSO): δ7.09-7.13 (4H), δ7.57-7.61 (2H), δ8.20-8.22 (2H), δ8.59-8.61 (2H), δ8.67-8.69 (2H), δ12.53 (2H). λmax=354 nm (EtOAc).

Synthesis Example p12

Preparation of Exemplified Compound (5)

Exemplified Compound (5) was synthesized by the same preparation method as Exemplified Compound (2) of Example 2 by changing the raw material 4-cyanobenzoyl chloride to 4-(chloroformyl)benzamide. $^1$H NMR (deuterated DMSO): δ7.07-7.11 (4H), δ7.56-7.62 (3H), δ8.13-8.15 (2H), δ8.23 (1H), δ8.59-8.65 (4H), δ12.55 (2H). λmax=353 nm (EtOAc).

Synthesis Example p13

Preparation of Exemplified Compound (19)

Exemplified Compound (19) was synthesized by the same preparation method as Exemplified Compound (21) of Example p5 by changing the raw material 2-ethylhexanol to 1-butanol. $^1$H NMR (CDCl$_3$): δ1.00-1.04 (3H), δ1.48-1.53 (2H), δ1.78-1.84 (2H), δ4.40 (2H), δ7.06-7.13 (4H), δ7.54-7.58 (2H), δ8.25-8.28 (2H), δ8.53-8.57 (4H), δ12.93 (2H). λmax=354 nm (EtOAc).

Synthesis Example p14

Preparation of Exemplified Compound (10)

Exemplified Compound (10) was synthesized by the same preparation method as Exemplified Compound (2) of Example p2 by changing the raw material 4-cyanobenzoyl chloride to 4-nitrobenzoyl chloride. $^1$H NMR (CDCl$_3$): δ7.07-7.15 (4H), δ7.56-7.61 (2H), δ8.45-8.48 (2H), δ8.53-8.55 (2H), δ8.65-8.68 (2H), δ12.75 (2H). λmax=356 nm (EtOAc).

Synthesis Example p15

Preparation of Exemplified Compound (121)

Exemplified Compound (121) was synthesized by the same preparation method as Exemplified Compound (21) of Example p5 by changing the raw material 2-ethylhexanol to 3,7-dimethyl-1-octanol. $^1$H NMR (CDCl$_3$): δ0.86-0.89 (6H), δ0.97-1.00 (3H), δ1.17-1.35 (6H), δ1.62-1.65 (3H), δ1.84-1.87 (1H), δ4.43 (2H), δ7.04-7.13 (4H), δ7.53-7.58 (2H), δ8.24-8.27 (2H), δ8.53-8.55 (4H), δ12.91 (2H). λmax=354 nm (EtOAc).

Synthesis Example p16

Preparation of Exemplified Compound (120)

Exemplified Compound (120) was synthesized by the same preparation method as Exemplified Compound (21) of Example p5 by changing the raw material 2-ethylhexanol to 3,5,5-trimethyl-1-hexanol. $^1$H NMR (CDCl$_3$): δ0.94 (9H), δ1.03-1.05 (3H), δ1.14-1.19 (1H), δ1.31-1.35 (1H), δ1.62-1.88 (3H), δ4.41-4.44 (2H), δ7.05-7.13 (4H), δ7.54-7.58 (2H), δ8.24-8.27 (2H), δ8.53-8.57 (4H), δ12.93 (2H) λmax=354 nm (EtOAc).

Synthesis Example m1

Preparation of Exemplified Compound (m-2)

Salicylic acid (300 g) was suspended in 600 mL of toluene and after adding 258 g of thionyl chloride and 7 mL of DMF thereto, the mixture was stirred at 50° C. for 2 hours (Solution A). To a solution obtained by adding and dissolving 900 mL of acetonitrile and 660 g of DBU (diazabicycloundecene (1,8-diazabicyclo[5.4.0]undec-7-ene)) in 299.0 g of salicylamide, Solution A prepared above was added dropwise under the condition of 5° C., and the mixture was stirred at room temperature for 24 hours. To the resulting reaction solution, 300 mL of 35% hydrochloric acid was added, and the mixture was stirred at room temperature for 2 hours. The obtained solid was filtered and washed with water to obtain 504 g of Synthetic Intermediate mA (yield: 90%).

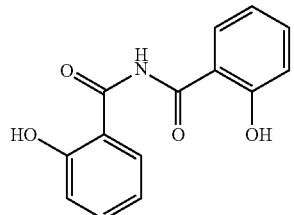

(Synthetic Intermediate mA)

Toluene (1,400 mL) and 10.5 g of p-toluenesulfonic acid monohydrate were added to 140 g of Synthetic Intermediate mA, and the mixture was stirred at 150° C. for 6 hours. After cooling to 60° C., 14 mL of triethylamine was added to the reaction solution, and the mixture was cooled to room temperature. The obtained solid was filtered and washed with water to obtain 122 g of Synthetic Intermediate mB (yield: 94%).

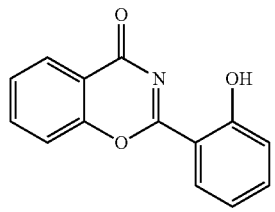

(Synthetic Intermediate mB)

Methanol (8,000 mL) and 309 g of a 28% sodium methoxide methanol solution were added to 401 g of isophthalonitrile, and the mixture was stirred at room temperature for 3 hours. To this reaction solution, 428 g of ammonium chloride was added, and the mixture was stirred at room temperature for 24 hours. The resulting reaction solution concentrated in a rotary evaporator, and the obtained solid was washed with methanol and ethyl acetate and recrystallized from water to obtain 310 g of Synthetic Intermediate mC (yield: 55%).

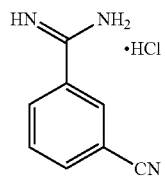

(Synthetic Intermediate mC)

Methanol (1,000 mL) and 44 g of a 28% sodium methoxide methanol solution were added to 42 g of Synthetic Intermediate mC. To the resulting suspension, 50 g of Synthetic Intermediate mB was added at room temperature, and the mixture was stirred at room temperature for 2 hours and at 60° C. for 2 hours. To this reaction solution, 2 mL of 35% hydrochloric acid was added, and the obtained solid was washed with methanol and water to obtain 74 g of Exemplified Compound (m-2) (yield: 96%). MS: m/z 367 (M+).

$^1$H NMR (CDCl$_3$): δ7.07-7.14 (4H), δ7.56-7.60 (2H), δ7.75-7.79 (1H), δ7.96-7.98 (1H), δ8.51-8.53 (2H), δ8.67-8.69 (1H), δ8.80 (1H), δ12.76 (1H). λmax=354 nm (EtOAc).

Synthesis Example m2

Preparation of Exemplified Compound (m-1)

Methanol (1,000 mL) was added to 100 g of Compound (m-2), and the mixture was stirred while bubbling hydrogen chloride gas at 60° C. for 24 hours. After cooling to room temperature, the obtained solid was washed with methanol and water to obtain 99 g of Exemplified Compound (m-1) (yield: 91%). MS: m/z 400 (M+)

$^1$H NMR (CDCl$_3$): δ4.03 (3H), δ7.05-7.13 (4H), δ7.53-7.58 (2H), δ7.69-7.73 (1H), δ8.34-8.36 (1H), δ8.54-8.56 (2H), δ8.62-8.64 (1H), δ9.12 (1H), δ12.93 (1H). λmax=353 nm (EtOAc).

Synthesis Example m3

Preparation of Exemplified Compound (m-3)

Acetonitrile (800 mL) and 444.0 g of DBU were added to 200.0 g of salicylamide and dissolved. To this solution, 303.9 g of 3-(trifluoromethyl)benzoyl chloride was added, and the mixture was stirred at room temperature for 24 hours. To the resulting reaction solution, 2,000 mL of water and 200 mL of hydrochloric acid were added, and the obtained solid was filtered and washed with water to obtain 428.3 g of Synthetic Intermediate mD (yield: 95%).

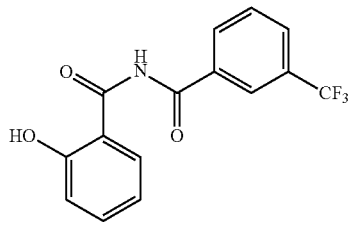

(Synthetic Intermediate mD)

Acetonitrile (240 mL) and 20.2 g of sulfuric acid were added to 34.0 g of Synthetic Intermediate mD, and the mixture was stirred at 90° C. for 4 hours. To the resulting reaction solution, 150 mL of triethylamine was added, and the mixture was cooled to room temperature. The obtained solid was filtered and washed with water to obtain 34.8 g of Synthetic Intermediate mE (yield: 94%).

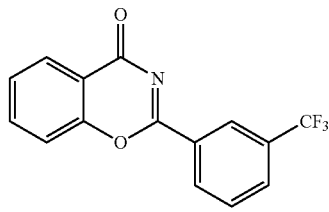

(Synthetic Intermediate mE)

Methanol (50 mL) and 4.6 g of a 28% sodium methoxide methanol solution were added to 6.8 g of Compound (X-4). To this solution, 5.0 g of Synthetic Intermediate mE was added, and the mixture was stirred at 60° C. for 3 hours. The resulting reaction solution was cooled to room temperature, and 0.2 mL of 35% hydrochloric acid was added thereto. The obtained solid was filtered and washed with water and methanol to obtain 6.7 g of Exemplified Compound (m-3) (yield: 95%). MS: m/z 409 (M+).

Synthesis Example m4

Preparation of Exemplified Compound (m-10)

Ethanol (2,500 mL), 2,000 mL of a 10% potassium hydroxide ethanol solution and 500 mL of water were added to 50 g of Exemplified Compound (m-1), and the mixture was stirred at room temperature for 24 hours. To the resulting solution, 300 mL of 35% hydrochloric acid was added, and the obtained solid was washed with methanol and water to obtain 46 g of Exemplified Compound (m-10) (yield: 95%). MS: m/z 386 (M+).
$^1$H NMR (deuterated DMSO): δ7.10-7.14 (4H), δ7.57-7.61 (2H), δ7.81-7.85 (1H), δ8.28-8.30 (1H), δ8.55-8.57 (2H), δ8.79-8.81 (1H), δ9.08 (1H), δ12.56 (2H). λmax=353 nm (EtOAc).

Synthesis Example m5

Preparation of Exemplified Compound (m-19)

1-Hexanol (200 g) and 13 g of sulfuric acid were added to 25 g of Exemplified Compound (m-2), and the mixture was stirred for 16 hours under reflux conditions. After cooling to room temperature, the obtained solid was washed with methanol and water to obtain 29 g of Exemplified Compound (m-19) (yield: 90%). MS: m/z 470 (M+). λmax=354 nm (EtOAc).

Synthesis Example m6

Preparation of Exemplified Compound (m-20)

2-Ethylhexanol (200 g) and 13 g of sulfuric acid were added to 25 g of Exemplified Compound (m-2), and the mixture was stirred for 16 hours under reflux conditions. After cooling to room temperature, the obtained solid was washed with methanol and water to obtain 31 g of Exemplified Compound (m-20) (yield: 92%). MS: m/z 498 (M+).
$^1$H NMR (CDCl$_3$): δ0.90-0.94 (3H), δ1.00-1.04 (3H), δ1.38-1.63 (8H), δ1.77-1.83 (1H), δ4.30-4.39 (2H), δ7.04-7.12 (4H), δ7.53-7.55 (2H), δ7.57-7.58 (1H), δ7.71-7.73 (1H), δ8.34-8.36 (2H), δ8.54-8.65 (1H), δ9.16 (1H), δ12.94 (2H). λmax=354 nm (EtOAc).

Synthesis Example m7

Preparation of Exemplified Compound (m-21)

3,5,5-Trimethyl-1-hexanol (200 g) and 13 g of sulfuric acid were added to 25 g of Exemplified Compound (m-2), and the mixture was stirred for 16 hours under reflux conditions. After cooling to room temperature, the obtained solid was washed with methanol and water to obtain 32 g of Exemplified Compound (m-21) (yield: 91%). MS: m/z 512 (M+). $^1$H NMR (CDCl$_3$): δ0.88-0.93 (9H), δ1.07-1.08 (3H), δ1.14-1.92 (1H), δ1.32-1.37 (1H), δ1.67-1.88 (3H), δ4.40-4.45 (2H), δ6.99-7.06 (4H), δ7.48-7.53 (2H), δ7.64-7.68 (1H), δ8.29-8.32 (1H), δ8.46-8.57 (3H), δ9.08 (1H), δ12.86 (2H). λmax=354 nm (EtOAc).

Synthesis Example m8

Preparation of Exemplified Compound (m-58)

Acetonitrile (80 mL) and 36.4 g of DBU were added to 20.0 g of 3-methoxysalicylamide and dissolved. To this solution, 23.8 g of methyl 3-(chloroformyl)benzoate was added, and the mixture was stirred at room temperature for 24 hours. To the resulting reaction solution, 100 mL of water and 20 mL of hydrochloric acid were added, and the obtained solid was filtered and washed with water to obtain 36.0 g of Synthetic Intermediate mH (yield: 91%).

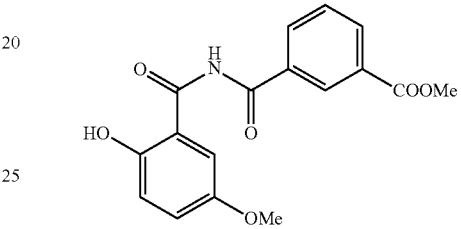

(Synthetic Intermediate mH)

Acetonitrile (200 mL) and 8.9 g of sulfuric acid were added to 20.0 g of Synthetic Intermediate mH, and the mixture was stirred at 90° C. for 4 hours. To the resulting reaction solution, 80 mL of triethylamine was added, and the mixture was cooled to room temperature. The obtained solid was filtered and washed with water to obtain 17.1 g of Synthetic Intermediate mI (yield: 90%).

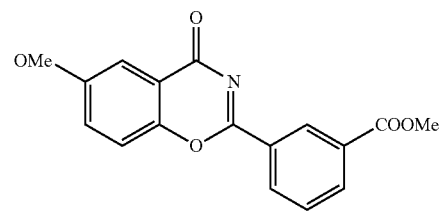

(Synthetic Intermediate mI)

Methanol (50 mL) and 3.4 g of a 28% sodium methoxide methanol solution were added to 5.5 g of Compound (X-4). To this solution, 5.0 g of Synthetic Intermediate mI was added, and the mixture was stirred at 60° C. for 3 hours. The resulting reaction solution was cooled to room temperature, and 0.2 mL of hydrochloric acid was added thereto. The obtained solid was filtered and washed with water and methanol to obtain 6.3 g of Exemplified Compound (m-58) (yield: 91%). MS: m/z 430 (M+).

Synthesis Example m9

Preparation of Exemplified Compound (m-61)

Acetonitrile (80 mL) and 29.7 g of DBU were added to 20.0 g of 2-hydroxy-3-(trifluoromethyl)benzamide and dissolved. To this solution, 19.4 g of methyl 4-(chloroformyl)benzoate was added, and the mixture was stirred at room temperature for 24 hours. To the resulting reaction solution, 100 mL of water and 20 mL of 35% hydrochloric acid were added, and the obtained solid was filtered and washed with water to obtain 34.1 g of Synthetic Intermediate mJ (yield: 95%).

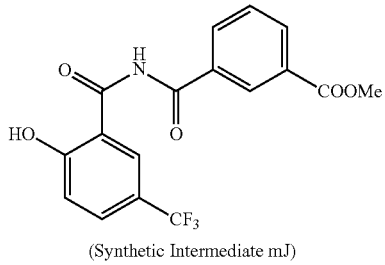 [SMILES: COC(=O)c1cccc(C(=O)NC(=O)c2cc(C(F)(F)F)ccc2O)c1]

(Synthetic Intermediate mJ)

Acetonitrile (200 mL) and 6.9 g of sulfuric acid were added to 20.0 g of Synthetic Intermediate mJ, and the mixture was stirred at 90° C. for 4 hours. To the resulting reaction solution, 80 mL of triethylamine was added, and the mixture was cooled to room temperature. The obtained solid was filtered and washed with water to obtain 18.4 g of Synthetic Intermediate mK (yield: 97%).

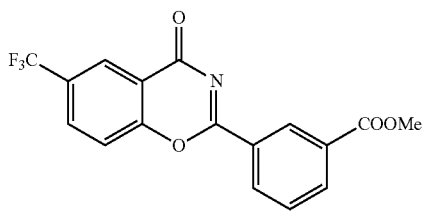

(Synthetic Intermediate mK)

Methanol (100 mL) and 3.4 g of a 28% sodium methoxide methanol solution were added to 5.5 g of Compound (X-4). To this solution, 5.0 g of Synthetic Intermediate mK was added, and the mixture was stirred at 60° C. for 3 hours. The resulting reaction solution was cooled to room temperature, and 0.2 mL of 35% hydrochloric acid was added thereto. The obtained solid was filtered and washed with water and methanol to obtain 5.9 g of Exemplified Compound (m-61) (yield: 91%). MS: m/z 468 (M+).

Synthesis Example m10

Preparation of Exemplified Compound (m-18)

Exemplified Compound (m-18) was synthesized by the same preparation method as Exemplified Compound (m-19) of Example m5 by changing the raw material 1-ethylhexanol to 1-butanol.
$^1$H NMR (CDCl$_3$): δ1.03-1.07 (3H), δ1.55-1.87 (4H), δ4.41-4.45 (2H), δ7.04-7.12 (4H), δ7.53-7.58 (2H), δ7.68-7.73 (1H), δ8.34-8.36 (1H), δ8.54-8.56 (2H), δ8.62-8.64 (1H), δ9.15 (1H), δ12.93 (2H). λmax=354 nm (EtOAc).

Synthesis Example m11

Preparation of Exemplified Compound (m-25)

Exemplified Compound (m-25) was synthesized by the same preparation method as Exemplified Compound (m-19) of Example m5 by changing the raw material 1-ethylhexanol to FINEOXOCOL 180N.

$^1$H NMR (CDCl$_3$): δ0.72-1.86 (35H), δ4.30-4.37 (2H), δ7.04-7.10 (4H), δ7.51-7.55 (2H), δ7.68-7.72 (1H), δ8.32-8.34 (1H), δ8.51-8.53 (2H), δ8.61-8.63 (1H), δ9.14 (1H), δ12.91 (2H). λmax=354 nm (EtOAc).

Synthesis Example m12

Preparation of Exemplified Compound (m-71)

Exemplified Compound (m-71) was synthesized by the same preparation method as Exemplified Compound (m-3) of Example m3 by changing the raw material salicylamide to 4-methoxysalicylamide.
$^1$H NMR (CDCl$_3$): δ3.92 (3H), δ6.58 (1H), δ6.64-6.66 (1H), δ7.05-7.12 (2H), δ7.54-7.57 (1H), δ7.74-7.79 (1H), δ7.92-7.94 (1H), δ8.43-8.52 (2H), δ8.61-8.63 (1H), δ8.73 (1H), δ12.98 (1H), δ13.14 (1H). λmax=354 nm (EtOAc).

Synthesis Example m13

Preparation of Exemplified Compound (m-72)

Exemplified Compound (m-72) was synthesized by the same preparation method as Exemplified Compound (m-3) of Example m3 by changing the raw material salicylamide to 4-methoxysalicylamide and changing 3-(trifluoromethyl) benzoyl chloride to 3,5-bis(trifluoromethyl)benzoyl chloride.
$^1$H NMR (CDCl$_3$): δ3.92 (3H), δ6.59 (1H), δ6.66-6.68 (1H), δ7.07-7.14 (2H), δ7.56-7.59 (1H), δ8.18 (1H), δ8.40-8.42 (1H), δ8.48 (1H), δ8.88 (2H), δ12.76 (1H), δ12.94 (1H). λmax=356 nm (EtOAc).

Synthesis Example m14

Preparation of Exemplified Compound (m-73)

Exemplified Compound (m-73) was synthesized by the same preparation method as Exemplified Compound (m-19) of Example m5 by changing the raw material 1-hexanol to 3,7-dimethyl-1-octanol.
$^1$H NMR (CDCl$_3$): δ0.84-0.86 (6H), δ1.01-1.03 (3H), δ1.16-1.39 (6H), δ1.49-1.74 (4H), δ1.86-1.91 (1H), δ4.45 (2H), δ7.01-7.09 (4H), δ7.51-7.55 (2H), δ7.66-7.70 (1H), δ8.31-8.33 (1H), δ8.50-8.52 (2H), δ8.59-8.61 (1H), δ9.11 (1H), δ12.89 (2H). λmax=354 nm (EtOAc).

<Measurement Method of pKa>

Exemplified Compound (1) was dissolved in acetonitrile to have an absorbance of 1, and to this solution, 70% perchloric acid (acetic acid solvent) was added dropwise, whereby the pH was changed. At this time, the solution absorption spectrum was measured, and the ratio between the triazine-free form and the proton adduct at each pH was computed from the absorbance at λmax. The value of pKa was determined from the point at which the values for the ratio became equal. Here, the triazine-free form indicates Exemplified Compound (1) itself, and the proton adduct indicates a compound resulting from addition of a proton to the nitrogen atom of the triazine ring of Exemplified Compound (1). The compounds of the present invention shown in Table 1 below and Comparative Compounds A and B were determined for the pKa value in the same manner. The absorption spectrum was measured using a spectrophotometer, UV-3600 (trade name), manufactured by Shimadzu Corporation, and the pH was measured using a pH meter, HM60G (trade name), manufactured by To a Denpa Kogyo.

<Production and Evaluation of Polymer Film>

A binder solution was prepared by dissolving 22 mass % of a PMMA resin ("DIANAL BR-80", trade name, produced by Mitsubishi Rayon Co., Ltd.) in methylene chloride. A coating solution was then prepared by dissolving 0.2 mass % of Exemplified Compound (1) in the binder solution above. The coating solution was applied on glass as a base material by means of a 200 μm blade and dried at 100° C. for 10 minutes to form a 50-μm thick coating, whereby a film was produced. Similarly, a film was produced using each of the compounds of the present invention shown in Table 1 below and Comparative Compounds A and B. The absorbance of the film produced was measured using a spectrophotometer, UV-3600 (trade name), produced by Shimadzu Corp. The film was irradiated with light of a metal halide lamp (where light at about 290 nm or less is cut) (Eye Super UV tester, trade name, manufactured by Iwasaki Electric Co., Ltd.) under the conditions of an illuminance of 90 mW/cm$^2$, a temperature of 63° C. and a humidity of 50%, and the residual amount of each compound after irradiation for 600 hours was measured. The residual amount was calculated according to the following formula:

Residual amount (%)=100×(absorbance after irradiation)/(absorbance before irradiation)

Incidentally, the absorbance is a value measured at the maximum absorption wavelength of each compound. The results are shown in Table 1.

TABLE 1

| Sample No. | Compound | Residual Amount (%) | pKa | |
|---|---|---|---|---|
| p1 | Exemplified Compound (1) | 98 | −5.0 | Invention |
| p2 | Exemplified Compound (2) | 99 | −5.4 | Invention |
| p3 | Exemplified Compound (3) | 98 | −5.3 | Invention |
| p4 | Exemplified Compound (5) | 97 | −5.0 | Invention |
| p5 | Exemplified Compound (9) | 98 | −5.0 | Invention |
| p6 | Exemplified Compound (10) | 99 | −5.6 | Invention |
| p7 | Exemplified Compound (19) | 98 | −5.0 | Invention |
| p8 | Exemplified Compound (21) | 98 | −5.0 | Invention |
| p9 | Exemplified Compound (24) | 98 | −5.0 | Invention |
| p10 | Exemplified Compound (72) | 99 | −5.2 | Invention |
| p11 | Exemplified Compound (81) | 98 | −5.0 | Invention |
| p12 | Exemplified Compound (84) | 98 | −5.1 | Invention |
| p13 | Exemplified Compound (98) | 97 | −5.0 | Invention |
| p14 | Exemplified Compound (104) | 89 | −5.0 | Invention |
| p15 | Exemplified Compound (120) | 98 | −5.0 | Invention |
| p16 | Exemplified Compound (121) | 98 | −5.0 | Invention |
| m1 | Exemplified Compound (m-1) | 98 | −5.1 | Invention |
| m2 | Exemplified Compound (m-2) | 99 | −5.5 | Invention |
| m3 | Exemplified Compound (m-3) | 98 | −5.4 | Invention |
| m4 | Exemplified Compound (m-10) | 98 | −5.1 | Invention |
| m5 | Exemplified Compound (m-18) | 98 | −5.1 | Invention |
| m6 | Exemplified Compound (m-19) | 98 | −5.1 | Invention |
| m7 | Exemplified Compound (m-20) | 98 | −5.1 | Invention |
| m8 | Exemplified Compound (m-21) | 98 | −5.1 | Invention |
| m9 | Exemplified Compound (m-25) | 98 | −5.1 | Invention |
| m10 | Exemplified Compound (m-58) | 96 | −5.0 | Invention |
| m11 | Exemplified Compound (m-61) | 98 | −5.1 | Invention |
| m12 | Exemplified Compound (m-71) | 97 | −5.0 | Invention |
| m13 | Exemplified Compound (m-72) | 99 | −5.6 | Invention |
| m14 | Exemplified Compound (m-73) | 98 | −5.1 | Invention |
| A | Comparative Compound A | 44 | −4.9 | Comparative Example |
| B | Comparative Compound B | 14 | −4.4 | Comparative Example |

TABLE 1-continued

| Sample No. | Compound | Residual Amount (%) | pKa |
|---|---|---|---|

TINUVIN1577FF
(Comparative Compound A)

CYASORB UV-1164
(Comparative Compound B)

The compounds above are commercially available, that is, Comparative Compound A is Tinuvin 1577FF produced by Ciba, and Comparative Compound B is CYASORB UV-1164 produced by CYTEC.

As apparent from the results of Tables 1 and 2, the compounds of the invention are high in the residual amount and are hardly decomposed by light irradiation at a high temperature, compared with comparative compounds (existing ultraviolet absorbers having absorption in the UV-A region).

Industrial Applicability

The compound of the present invention can be used as an ultraviolet absorber. Also, the compound exhibits high light fastness even in the long-wavelength ultraviolet region and when the compound of the present invention is incorporated into a resin composition for forming a polymer shape-formed article such as plastic and fiber, light stability of the polymer shape-formed article can be enhanced.

While the present invention has been described in detail and with reference to specific embodiments thereof, it will be apparent to one skilled in the art that various changes and modifications can be made therein without departing from the spirit and scope of the present invention.

This application is based on Japanese Patent Application (Patent Application No. 2009-176897) filed on Jul. 29, 2009, Japanese Patent Application (Patent Application No. 2009-206478) filed on Sep. 7, 2009, Japanese Patent Application (Patent Application No. 2009-221661) filed on Sep. 25, 2009, Japanese Patent Application (Patent Application No. 2010-9536) filed on Jan. 19, 2010, Japanese Patent Application (Patent Application No. 2010-152490) filed on Jul. 2, 2010, and Japanese Patent Application (Patent Application No. 2010-152491) filed on Jul. 2, 2010, the contents of which are incorporated herein by way of reference.

The invention claimed is:

1. A compound represented by the following formula (1):

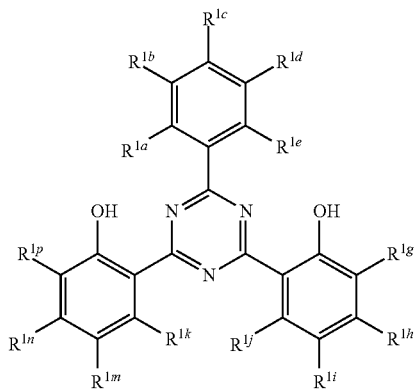

wherein each of $R^{1a}$, $R^{1b}$, $R^{1c}$, $R^{1d}$ and $R^{1e}$ independently represents a hydrogen atom or a monovalent substituent excluding OH, provided that at least one substituent represents $COOR^r$, wherein $R^r$ represents a hydrogen atom or a monovalent substituent, as a substituent having a Hammett's σp value of 0.3 or more, and substituents may combine with each other to form a ring, and each of $R^{1g}$, $R^{1h}$, $R^{1i}$, $R^{1j}$, $R^{1k}$, $R^{1m}$, $R^{1n}$ and $R^{1p}$ independently represents a hydrogen atom or a monovalent substituent, provided that $R^{1h}$ or $R^{1n}$ is a hydrogen atom and that substituents may combine with each other to form a ring;

wherein each monovalent substituent independently is a halogen atom, a substituted or unsubstituted alkyl group having a carbon number of 1 to 20, a cyano group, a carboxyl group, a substituted or unsubstituted alkoxycarbonyl group, a substituted or unsubstituted carbamoyl group, a substituted or unsubstituted alkylcarbonyl group, a nitro group, a substituted or unsubstituted amino group, an alkoxy group having a carbon number of 1 to 20, a substituted or unsubstituted aryloxy group, a substituted or unsubstituted sulfamoyl group, a thiocyanate group, or a substituted or unsubstituted alkylsulfonyl group and in the case of having a substituent, the substituent is a halogen atom, an alkyl group having a carbon number of 1 to 20, a cyano group, a carboxyl group, an alkoxycarbonyl group, a carbamoyl group, an alkylcarbonyl group, a nitro group, an amino group, a hydroxy group, an alkoxy group having a carbon number of 1 to 20, an aryloxy group, a sulfamoyl group, a thiocyanate group or an alkylsulfonyl group.

2. The compound as claimed in claim 1, wherein each of $R^{1a}$, $R^{1c}$ and $R^{1e}$ independently represents a hydrogen atom or a monovalent substituent excluding OH, provided that at least one substituent represents $COOR^r$, wherein $R^r$ represents a hydrogen atom or a monovalent substituent, as a substituent having a Hammett's σp value of 0.3 or more, and each of $R^{1b}$ and $R^{1d}$ independently represents a hydrogen atom or a monovalent substituent excluding OH, provided that substituents may combine with each other to form a ring.

3. The compound as claimed in claim 1, wherein each of $R^{1a}$, $R^{1c}$ and $R^{1e}$ represents a hydrogen atom, each of $R^{1b}$ and $R^{1d}$ independently represents a hydrogen atom or $COOR^r$, at least $R^{1b}$ or $R^{1d}$ represents $COOR^r$, and $R^r$ represents a hydrogen atom or a monovalent substituent, as a substituent having a Hammett's σp value of 0.3 or more.

4. The compound as claimed in claim 1, wherein $R^{1c}$ is a cyano group.

5. The compound as claimed in claim 1, wherein $R^{1g}$, $R_{1h}$, $R^{1i}$, $R^{1j}$, $R^{1k}$, $R^{1m}$, $R^{1n}$ and $R^{1p}$ are a hydrogen atom.

6. An ultraviolet absorber comprising the compound claimed in claim 1.

7. A resin composition containing the compound claimed in claim 1.

8. The compound as claimed in claim 1, wherein $R^r$ represents a monovalent substituent.

9. The compound as claimed in claim 8, wherein the monovalent substituent represents a linear or branched alkyl group having a carbon number of 1 to 20.

10. An ultraviolet absorber comprising the compound claimed in claim 8.

11. A resin composition containing the compound claimed in claim 8.

* * * * *